United States Patent
Sengupta et al.

(10) Patent No.: US 9,884,123 B2
(45) Date of Patent: Feb. 6, 2018

(54) LIGAND-TARGETED MOLECULES AND METHODS THEREOF

(71) Applicant: INVICTUS ONCOLOGY PVT. LTD., Delhi (IN)

(72) Inventors: Shiladitya Sengupta, Waltham, MA (US); Sazid Hussain, Delhi (IN); Dipankar Pramanik, Delhi (IN); Monideepa Roy, Delhi (IN); Seikh Samad Hossain, Delhi (IN)

(73) Assignee: INVICTUS ONCOLOGY PVT. LTD., Delhi (IN)

( * ) Notice: Subject to any disclaimer, the term of this patent is extended or adjusted under 35 U.S.C. 154(b) by 425 days.

(21) Appl. No.: 14/370,524

(22) PCT Filed: Jan. 3, 2013

(86) PCT No.: PCT/US2013/020130
§ 371 (c)(1),
(2) Date: Jul. 3, 2014

(87) PCT Pub. No.: WO2013/103707
PCT Pub. Date: Jul. 11, 2013

(65) Prior Publication Data
US 2015/0045428 A1    Feb. 12, 2015

(30) Foreign Application Priority Data
Jan. 3, 2012 (IN) .............. 18/DEL/2012

(51) Int. Cl.
*A61K 47/48* (2006.01)
*A61K 47/68* (2017.01)
(Continued)

(52) U.S. Cl.
CPC ...... *A61K 47/48215* (2013.01); *A61K 31/282* (2013.01); *A61K 47/00* (2013.01);
(Continued)

(58) Field of Classification Search
None
See application file for complete search history.

(56) References Cited

U.S. PATENT DOCUMENTS

| 4,952,676 A | 8/1990 | Heffernan et al. |
| 2004/0235712 A1 | 11/2004 | Lippard et al. |
| 2009/0004118 A1* | 1/2009 | Nie .................. A61K 47/48076 424/9.35 |

FOREIGN PATENT DOCUMENTS

| EP | 0169645 A1 | 1/1986 |
| WO | 2008/141111 A2 | 11/2008 |

OTHER PUBLICATIONS

Garmann et al. "Cellular accumulation and cytotoxicity of macromolecular platinum complexes in cisplatin-resistant tumor cells." J. of Controlled Release, Elsevier, Amsterdam, NL, vol. 131, No. 2, Oct. 21, 2008, pp. 100-106.
(Continued)

*Primary Examiner* — Bethany P Barham
*Assistant Examiner* — Dominic Lazaro
(74) *Attorney, Agent, or Firm* — Nixon Peabody LLP; David S. Resnick

(57) ABSTRACT

The present invention relates to ligand-targeted molecules and ligand drug conjugates (LDCs) comprising a ligand connected to a functional group, which is connected to a linker, which in turn is bonded to a drug. The LDCs of the present invention also comprise platinum coordination complex wherein the platinum is connected to the linker through monocarboxylato and O→Pt coordinate bonds. The present invention also relates to methods for preparing these ligand drug conjugates. The present invention further relates to methods for the treatment of tumours using the ligand drug conjugates of the present invention.

11 Claims, 42 Drawing Sheets

(51) Int. Cl.
  *A61K 47/00*  (2006.01)
  *A61K 31/282* (2006.01)
  *C07F 15/00*  (2006.01)
  *A61K 47/50*  (2017.01)
  *A61K 47/60*  (2017.01)

(52) U.S. Cl.
  CPC .. *A61K 47/48561* (2013.01); *A61K 47/48692* (2013.01); *A61K 47/50* (2017.08); *A61K 47/60* (2017.08); *A61K 47/68* (2017.08); *A61K 47/6803* (2017.08); *A61K 47/6849* (2017.08); *A61K 47/6883* (2017.08); *C07F 15/0086* (2013.01)

(56) References Cited

OTHER PUBLICATIONS

Aronov et al. "Folate-Targeted PEG as a Potential Carrier for Carboplatin Analogs. Synthesis and in Vitro Studies." Bioconjugate Chemistry, vol. 14, No. 3, May 2003, pp. 563-574.

Ndinguri et al. "Peptide Targeting of Platinum Anti-Cancer Drugs." Bioconjugate Chemistry, vol. 20, No. 10, Oct. 21, 2009, pp. 1869-1878.

Song et al. "Synthesis and hydrolytic properties of polyphosphazene/(diamine)platinum/saccharide conjugates." J. of Controlled Release, Elsevier, Amsterdam, NL, vol. 55, No. 2-3, Nov. 13, 1998, pp. 161-170.

Alley et al., "Antibody-drug conjugates: targeted drug delivery for cancer", Current Opinion in Chemical Biology 14:529-537 (2010).

Aronov et al., "Nuclear Localization Signal-Targeted Poly(ethylene glycol) Conjugates as Potential Carriers and Nuclear Localizing Agents for Carboplatin Analogues", Bioconjugate Chemistry 15(4):814-823 (2004).

Carter et al., "Antibody-Drug Conjugates for Cancer Therapy", The Cancer Journal 14(3):154-169 (2008).

Da Ros et al., "Morphine modulates doxorubicin uptake and improves efficacy of chemotherapy in an intracranial xenograft model of human glioblastoma", American Journal of Cancer Research 6(3):639-648 (2016).

Guillemard et al., "Taxane-Antibody Conjugates Afford Potent Cytotoxicity, Enhanced Solubility, and Tumor Target Selectivity", Cancer Research 61:694-699 (2001).

Gulley et al., "Immunotherapy for Prostate Cancer: Recent Advances, Lessons Learned, and Areas for Further Research", Clinical Cancer Research 17(12):3884-3891 (2011).

McIntosh et al., "Pharmacokinetics and Tissue Distribution of Cisplatin and Conjugates of Cisplatin with Carboxymethyldextran and A5B7 Monoclonal Antibody in CD1 Mice", Journal of Pharmaceutical Sciences 86 (12):1478-1483 (1997).

Ohya et al., "Design of Poly(ethylene glycol) Immobilizing Platinum Complex through Chelate-type Coordination Bond", Polymers for Advanced Technologies 11:635-641 (2000).

Trail et al., "Antigen-specific Activity of Carcinoma-reactive BR64-Doxorubicin Conjugates Evaluated in Vitro and in Human Tumor Xenograft Models", Cancer Research 52:5693-5700 (1992).

Noji M., "Development of the 3rd generation anticancer platinum complex, Oxaliplatin", The Bulletin of the Suzuka University of Medical Science 12 (2005). (14 pages).

\* cited by examiner

Pt(II) linker forms a dicarboxylato linkage and the complex is flanked on one side by a non-polar and the other side by a PEG spacer.

Pt(II) linker complex is flanked on both sides by a PEG spacer.

Pt(II) is linked to oxygen via a monocarboxylato and O→Pt coordinate bond, and flanked on both sides by a PEG spacer.

Scheme 6

7

Scheme 11

Scheme 12

US 9,884,123 B2

LIGAND-TARGETED MOLECULES AND METHODS THEREOF

CROSS REFERENCE TO RELATED APPLICATIONS

This application is a 35 U.S.C. §371 National Phase Entry Application of International Application No. PCT/US2013/020130 filed Jan. 3, 2013, which designates the U.S., and which claims benefit under one or more of 35 U.S.C. § 119(a)-119(d) of Indian Patent Application No. 18/DEL/2012, filed Jan. 3, 2012, the content of which is incorporated herein by reference in its entirety.

TECHNICAL FIELD

The present invention relates to ligand-targeted molecules and ligand drug conjugates. The present invention also relates to methods of preparing these ligand-targeted molecules and ligand drug conjugates, as well as methods of using these ligand drug conjugates for the treatment of tumours.

BACKGROUND

Despite recent improvements in cancer therapy due to the introduction of novel therapeutics, the incidence of cancer has been on the rise. Traditional chemotherapy is still one of the pillars for the treatment of cancer. Chemotherapy is often based on the use of drugs that are toxic to cancer cells. Several general classes of chemotherapeutic drugs have been developed. One such class of genotoxic drugs that have been shown to damage cellular DNA by producing cross-links therein are cisplatin [cis-diamminedichloroplatinum (II)] and carboplatin [diammine(1,1-cyclobutanedicarboxylato)-platinum(II)] (*Eur J Cancer* 1998; 34:1535-42; *Chem Rev.* 1999; 2467-98). Cisplatin is one of the most commonly used chemotherapeutic agents, and is a first line therapy for most malignancies. Cisplatin and other Pt(II) analogs, such as carboplatin and oxaliplatin, are currently used in the treatment of selected, diverse neoplasms of epithelial and mesenchymal origin.

However, traditional chemotherapeutic agents are not tumour specific; their selectivity largely relies on the premise that rapidly proliferating cells are more prone to the cytotoxic effect of these drugs. Therefore, increased toxicities against normal tissues characterized by an enhanced proliferation rate represent a major drawback of this approach. As consequence of this low efficacy and unspecific toxicity, chemotherapeutics are often given at suboptimal doses. For example, Cisplatin and related Pt (II) agents are characterised by nephrotoxicity, neurotoxcity and myelosupression. Thus, the unmet medical need is for innovative strategies that focus toxicity to tumor cells while sparing healthy tissues. The development of antibody-drug conjugates (ADCs) by empowering antibodies or a targeting-ligand with a cytotoxic drug directed against tumor-associated antigens represents a promising therapeutic strategy for site-specific drug delivery.

The antibody-drug conjugate (ADCs) concept is a promising strategy to deliver a cytotoxic drug selectively to a target. Such conjugates represent a broadly applicable approach to enhance the antitumor activity of antibodies, and improve the tumor-to-normal tissue selectivity of chemotherapy (*Cancer J* 2008; 14:154-169). A significant number of ADCs are currently in clinical development, and recently Brentuximab vedotin (SGN-35) has been approved by the FDA (*CCR Focus, Clin Can Res* 2011:17). Although immuno-conjugates of doxorubicin (*Cancer Res.* 1992; 15; 5693-700), cisplatin (*J Pharm Sci.* 1997; 86:1478-83) and taxanes (*Cancer Res* 2001; 61, 694-699) has been tried before, developing antibody-targeted chemotherapeutics has been a challenge. The major problem associated were loss of structural integrity of antibodies and drug potency. Significant progress in these areas has been made, with careful optimization of several parameters, including antibody specificity, drug potency, linker technology, and the stoichiometry and placement of conjugated drugs (*Curr Opin Chem Biol.* 2010; 14:529-37).

Site-specific delivery of platinum compounds to tumor cells has been attempted previously. This was achieved by directly complexing platinum to PEG and delivering the drug in the untargeted form or as ligand-targeted conjugate to tumor associated antigens. In one report, attempt was made to conjugate carboplatin with PEG (*Polym Adv Technol.* 2000; 11:635-41). In other examples of prior art, folate-targeted PEGylated carboplatin analogs (*Bioconj Chem.* 2003; 14:563-74) as well as peptide-targeted carboplatin were tested on tumor cells in vitro (*Bioconj Chem.* 2004; 4:814-23). The complexes were ineffective for practical usage in terms of cytotoxicity, antigen binding activity and in vivo stability. The limitations associated to previous versions of Pt-antibody conjugates could be attributed to the use of antibodies of murine origin, the choice of the cell surface receptor, method of synthesis resulting in the potential binding of Pt to the antibody disulfides, or inability of the Pt to aquate due to formation of stable linkages resulting in inefficient release kinetics.

SUMMARY

This invention relates to the generation and usage of novel platinum (II) coordination compounds linked to a targeting ligand where the platinum is co-ordinated to a leaving group via an unique O—Pt and a =O→Pt coordinate bond. The invention also provides complexes for the site-specific or disease-specific delivery of chemotherapeutic agents for anti-cancer therapy. The present invention contemplates the use of different Pt (II) compounds and other cytotoxins, different targeting moieties in the format of ligand-targeted therapeutics. In any form, the conjugates may contain one or more Pt (II) therapeutic agents, and one or more targeting ligands.

The present invention is directed to ligand-targeted molecules comprising a hydrocarbon- or PEG-containing linker connected to a platinum moiety through a monocarboxylato and/or coordinate bond. These ligand-targeted molecules comprise a suitable functional moiety connected to a linker, which is connected to a dicarbonyl moeity, which in turn in connected to a platinum chemotheraputic agent. The present invention also provides ligand-targeted molecules wherein the linker comprises a Pt (II) coordination complex which is turn is connected to a cytotoxic agent or drug.

The present invention further discloses methods of preparing ligand-targeted molecules of the present invention comprising: a) a reacting amino acid, amino acid conjugate or peptide with maleimide-PEG-HOOC to obtain an intermediate; b) coupling the intermediate with a carboxylic acid or its derivative to obtain a carboxylate adduct; c) reacting the carboxylate adduct with a platinum (II) chemotherapeutic agent to form the ligand-targeted molecule. The present invention is also directed to methods of preparing ligand drug conjugates of the present invention comprising conjugating the ligand-targeted molecule of the present invention with a ligand. The present invention is also directed to methods of treating tumours using the molecules and conjugates of the invention.

Still another aspect of the invention is directed to pharmaceutical compositions comprising a conjugate described herein and a pharmaceutically acceptable carrier.

Yet another aspect of the invention is directed to a method of treating cancer or metastasis. The method includes selecting a subject in need of treatment for cancer or metastasis and administering to the subject an effective amount of any of the compounds, conjugates or compositions described herein.

BRIEF DESCRIPTION OF THE DRAWINGS

In FIGS. 16A and 16B, the free amine of lysine can be coupled to a spacer with a chelating unit with platinum. In FIG. 16C, two thiol group of the reduced antibody can bind to platinum with stable (non-cleavable) bond.

DETAILED DESCRIPTION

Figure 1A:
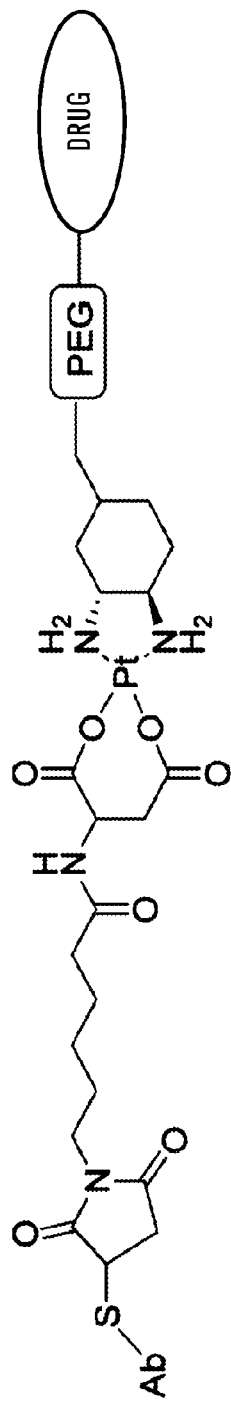
FIG. 1A shows a general structure of a ligand-drug conjugate where platinum act as a linker by forming dicarboxylato linkages. It is flanked by a non-polar spacer and to the drug by a PEG spacer.

The present invention is directed to ligand drug conjugates and their application as ligand-targeted therapeutics. The ligand-targeted molecules (LTM) of the present invention are conjugated to potent cytotoxic drugs to form ligand drug conjugates (LDC) which can be selectively delivered to a site of action of interest in an active form, and then cleaved to release the active drug.

The present invention provides a cytotoxic ligand-drug conjugate having the structure of Formula 1:

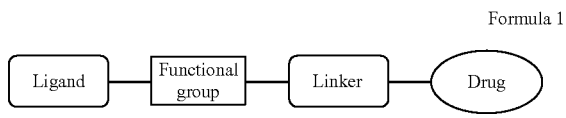

Formula 1

The formula above represents use of platinum as a drug per se or as a cleavable linker linking another cytotoxic agent/drug to the ligand.

In some embodiments, the drug is a Pt(II) agent conjugated to the linker by forming a Pt-coordination complex.

Another embodiment of the present invention also provides a novel ligand-drug conjugate wherein the linker includes the platinum coordination complex, and a drug, e.g., a cytotoxic drug is conjugated to the linker via the platinum. The platinum-coordination complex is bonded with cytotoxic drugs either through dicarbonyl linkages to the linker or through monocarbonyl linkages and O→Pt coordinate bond. Without limitations, the LDCs described herein can release the drug from the complex upon internalization into the cells. In these compounds, the platinum complex can act as a leaving group not as the drug. It serves as a linker that can be readily cleaved, thus providing an LDC that cleaves to release the cytotoxic agent/drug that is attached to the Pt moiety.

In another embodiment of the novel LDC, the linker coordination complex could have other metals such as Fe, Si to conjugate the cytotoxic agent.

In one aspect, the present disclosure provides a ligand-drug conjugate comprising a targeting moiety and a drug conjugated to each other via a linker, wherein the drug is a platinum compound. In some embodiments of this aspect, the ligand-drug conjugate is of formula A-B- C, wherein A is a ligand (e.g., a targeting moiety); B is a linker; and C is platinum compound.

In another aspect, the present disclosure provides a ligand-drug conjugate comprising a targeting moiety and a drug conjugated to each other via a linker, wherein the linker comprises a platinum compound/complex. In some embodiments of this aspect, the ligand-drug conjugate is of formula A-B-C- B'-D, wherein A is a ligand (e.g., a targeting moiety); B and B' are independently a linker, C is a coordination metal complex (e.g., a platinum complex); and D is therapeutic agent or drug. In embodiments of this aspect, the drug can be a second platinum compound or another cytotoxic agent/drug.

The disclosure also provides a conjugates of formula F-B-C, wherein F is a functional group, B is a linker, and C is a platinum compound.

The disclosure also provides a conjugate of formula F-B-C- B'-D, wherein F-B-C-B'-D, wherein F is functional group; B and B' are independently a linker; C is a coordination metal complex (e.g., a platinum complex); and D is drug. The functional group can be used to link the linker B with a targeting moiety or ligand.

In some embodiments, the platinum compound is linked to the linker via a dicarbonyl monomer present in the linker.

In some embodiments, the platinum compound is dissociably linked to the linker via at least one coordination bond. Without wishing to be bound by theory, the coordination bond is more liable and thus releases the platinum compound more easily relative to when the platinum compound is linked to the linker without the use of a coordination bond. In some embodiments, linking of the platinum compound to the linker further comprises a carboxylato bond. Accordingly, in some embodiments, the platinum compound is linked to the linker through a coordination bond and a carboxylato bond.

In some embodiments, the coordination bond is between platinum atom of the platinum compound and an oxygen of the dicarbonyl monomer of the linker. Preferably the coordination bond is between platinum and a carbonyl oxygen. In some embodiments, the coordination bond is between platinum atom of the platinum compound and an amide oxygen of the linker. In some embodiments, the coordination bond is between platinum atom of the platinum compound and an ester carbonyl oxygen linker.

In some embodiments, at least one (e.g., one, two, three, four, five, six, seven, eight, nine, ten or more) platinum compounds are linked to the linker. Without limitations, any platinum compound can be used in the conjugates described herein. In some embodiments, the platinum compound is a platinum(II) or platinum (IV) compound. In some embodiments, the platinum (II) compound is selected from the group consisting of cisplatin, oxaliplatin, carboplatin, paraplatin, sartraplatin, and combinations thereof.

In some embodiments, the platinum(II) compound is selected from the group consisting of Pt(NH$_3$)$_2$, Pt(NH$_3$)(2-methylpyridine), and

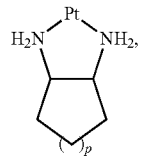

wherein p is 0, 1, 2, or 3. In one embodiment, the platinum (II) compound is Pt(NH$_3$)$_2$.

In some embodiments, the platinum (II) compound comprises at least two nitrogen atoms, where said nitrogen atoms are directly linked to platinum. In a further embodiment, the two nitrogen atoms are linked to each other via an optionally substituted linker, e.g. acyclic or cyclic linker. A cyclic linker means a linking moiety that comprises at least one ring structure. Cyclic linkers can be aryl, heteroaryl, cyclyl or heterocyclyl.

In some embodiments, the at least one nitrogen that is linked to platinum is a ring atom of a heteroaryl or a heterocyclyl. In one embodiment, heteroaryl is optionally substituted pyridine, e.g., 2-methylpyridine.

In some embodiments, the platinum compound is

wherein p is 2.

Without limitations any drug (e.g., therapeutic agent) can be conjugated in the targeting ligands drug conjugates described herein. As used herein, the term "therapeutic agent" refers to a substance used in the diagnosis, treatment, or prevention of a disease. Any therapeutic agent known to those of ordinary skill in the art to be of benefit in the diagnosis, treatment or prevention of a disease is contemplated as a therapeutic agent in the context of the present invention. Therapeutic agents include pharmaceutically active compounds, hormones, growth factors, enzymes, DNA, plasmid DNA, RNA, siRNA, antisense oligonucleotides, aptamers, ribozymes, viruses, proteins, lipids, pro-inflammatory molecules, antibodies, antibiotics, anti-inflammatory agents, anti-sense nucleotides and transforming nucleic acids or combinations thereof. Any of the therapeutic agents can be combined to the extent such combination is biologically compatible.

Exemplary therapeutic agents include, but are not limited to, those found in *Harrison's Principles of Internal Medicine*, 13th Edition, Eds. T. R. Harrison et al. McGraw-Hill N.Y., NY; Physicians Desk Reference, 50th Edition, 1997, Oradell New Jersey, Medical Economics Co.; Pharmacological Basis of Therapeutics, 8th Edition, Goodman and Gilman, 1990; United States Pharmacopeia, The National Formulary, USP XII NF XVII, 1990; current edition of Goodman and Oilman's *The Pharmacological Basis of Therapeutics*; and current edition of *The Merck Index*, the complete contents of all of which are incorporated herein by reference.

Examples of therapeutic agents which can be used, include but are not limited to, narcotic analgesic drugs; salts of gold; corticosteroids; hormones; antimalarial drugs; indole derivatives; pharmaceuticals for arthritis treatment;

antibiotics, including Tetracyclines, Penicillin, Streptomycin and Aureomycin; antihelmintic and canine distemper drugs, applied to domestic animals and large cattle, such, as, for example, phenothiazine; drugs based on sulfur, such, as sulfioxazole; antitumor drugs; pharmaceuticals supervising addictions, such as agents controlling alcohol addiction and agents controlling tobacco addiction; antagonists of drug addiction, such, as methadone; weightcontrolling drugs; thyroid gland controlling drugs; analgesics; drugs controlling fertilization or contraception hormones; amphetamines; antihypertensive drugs; antiinflammatories agents; antitussives; sedatives; neuromuscular relaxants; antiepileptic drugs; antidepressants; antidisrhythmic drugs; vasodilating drugs; antihypertensive diuretics; antidiabetic agents; anticoagulants; antituberculous agents; antipsyhotic agents; hormones and peptides. It is understood that above list is not full and simply represents the wide diversification of therapeutic agents that may be included in the compositions. In some embodiments, therapeutic agent is Mitoxantrone, protein (e.g. VEGF) or plasmid DNA.

In some embodiments, the therapeutic agent, e.g., the drug is an anti-cancer agent. As used herein, the term "anti-cancer agent" is refers to any compound (including its analogs, derivatives, prodrugs and pharmaceutically salts) or composition which can be used to treat cancer. Anti-cancer compounds for use in the present invention include, but are not limited to, inhibitors of topoisomerase I and II, alkylating agents, microtubule inhibitors (e.g., taxol), and angiogenesis inhibitors. Exemplary anti-cancer compounds include, but are not limited to, paclitaxel (taxol); docetaxel; gemicitabine; Aldesleukin; Alemtuzumab; alitretinoin; allopurinol; altretamine; amifostine; anastrozole; arsenic trioxide; Asparaginase; BCG Live; bexarotene capsules; bexarotene gel; bleomycin; busulfan intravenous; busulfanoral; calusterone; capecitabine; carboplatin; carmustine; carmustine with Polifeprosan Implant; celecoxib; chlorambucil; cisplatin; cladribine; cyclophosphamide; cytarabine; cytarabine liposomal; dacarbazine; dactinomycin; actinomycin D; Darbepoetin alfa; daunorubicin liposomal; daunorubicin, daunomycin; Denileukin diftitox, dexrazoxane; docetaxel; doxorubicin; doxorubicin liposomal; Dromostanolone propionate; Elliott's B Solution; epirubicin; Epoetin alfa estramustine; etoposide phosphate; etoposide (VP-16); exemestane; Filgrastim; floxuridine (intraarterial); fludarabine; fluorouracil (5-FU); fulvestrant; gemtuzumab ozogamicin; goserelin acetate; hydroxyurea; Ibritumomab Tiuxetan; idarubicin; ifosfamide; imatinib mesylate; Interferon alfa-2a; Interferon alfa-2b; irinotecan; letrozole; leucovorin; levamisole; lomustine (CCNU); mechlorethamine (nitrogenmustard); megestrol acetate; melphalan (L-PAM); mercaptopurine (6-MP); mesna; methotrexate; methoxsalen; mitomycin C; mitotane; mitoxantrone; nandrolone phenpropionate; Nofetumomab; LOddC; Oprelvekin; oxaliplatin; pamidronate; pegademase; Pegaspargase; Pegfilgrastim; pentostatin; pipobroman; plicamycin; mithramycin; porfimer sodium; procarbazine; quinacrine; Rasburicase; Rituximab; Sargramostim; streptozocin; talbuvidine (LDT); talc; tamoxifen; temozolomide; teniposide (VM-26); testolactone; thioguanine (6-TG); thiotepa; topotecan; toremifene; Tositumomab; Trastuzumab; tretinoin (ATRA); Uracil Mustard; valrubicin; valtorcitabine (monoval LDC); vinblastine; vinorelbine; zoledronate; and any mixtures thereof. In some embodiments, the anti-cancer agent is a paclitaxel-carbohydrate conjugate, e.g., a paclitaxel-glucose conjugate, as described in U.S. Pat. No. 6,218,367, content of which is herein incorporated by reference in its entirety.

In some embodiments, the drug is selected from the group of drugs shown in Table 1.

TABLE 1

Some exemplary drugs for conjugating with the targeting-ligand.

| Drug | Class | Mechanism | Source | IC50 | Remarks |
|---|---|---|---|---|---|
| Maytansinoid (DM1 and DM4) | Ansamycin | Microtubule disruptors | Ethiopian Shrub | nM to pM | |
| CC-1065 | | Binds to minor groove of DNA and alkylation | Bacteria | nM to pM | |
| Adozelesin (DC1) | Synthetic analogue of CC-1065 | | Synthetic | 0.02 nM | Poor solubility in aqueous system |
| DC4 | Water soluble analogue of DC1 | | Synthetic | | |
| Calicheamicins | Antibiotics | Binds to minor groove, strand breaks | | Picomolar | Poor pharmaceutic index |
| Dolastatins | Cyclic pentapeptides | Microtubule disruptors | Sea hare *Dolabella auricularia* | | Systemic cytotoxicity |
| Auristatins E and F | Synthetic analogues of dolastatins | Microtubule disruptors | Synthetic | nM to pM | |
| Meamycin | Analogue of FR901464 | Binds to splicing factor 3b | Synthetic; derived from *Pseudomonas* | picomolar | Active against MDR cells too |
| Doxorubicin | Antibiotic | | Natural | High nM | |
| Paclitaxel | Terpenoids | Microtubule stabilizer | Pacific yew tree | | |
| Docetaxel | | Microtubule stabilizer | | | |
| Laulimalide | Macrolide (Paclitaxel-like) | Microtubule stabilizer | sponge *Cacospongia mycofijiensis* | Low nM | Intrinsically unstable |

TABLE 1-continued

Some exemplary drugs for conjugating with the targeting-ligand.

| Drug | Class | Mechanism | Source | IC50 | Remarks |
|---|---|---|---|---|---|
| Epothilones A and B | Macrolide (Paclitaxel-like) | Microtubule stabilizer | *myxobacterium Sorangium cellulosum* | | Active against MDR cells too |
| Discodermolide | polyhydroxylated alkatetraene lactones (Paclitaxel-like) | Microtubule stabilizer | marine sponge *Discodermia dissoluta* | | |
| Eleutherobin | Terpenoids (Paclitaxel-like) | Microtubule stabilizer | soft coral *Eleutherobia sp.* | | |
| Peloruside A | Macrolide (Paclitaxel-like) | Microtubule stabilizer | marine sponge, *Mycale hentscheli* | Low nM | |
| cyclophosphamide, chlorambucil, uramustine, ifosfamide, melphalan, and bendamustine | Nitrogen mustards | Alkylating agent | Synthetic | | |
| Carmustine, lomustine, semustine | Nitrosoureas | Alkylating agents | Synthetic | | |
| Busulfan | Alkyl sulfonates | Alkylating agents | Synthetic | | |
| Thiotepa | | Alkylating agents | Synthetic | | |
| Dacarbazine | | Alkylating agents | Synthetic | | |
| Methotrexate | Antimetabolites | Folate antagonist | Synthetic | | |
| 6-mercaptopurine, 6-thioguanine, pentostatin, fludarabine | Antimetabolites | Purine antagonist | Synthetic | | |
| 5-fluorouracil, cytarabine, leukovorin | Antimetabolites | Pyrimidine antagonist | Synthetic | | |
| Dactinomycin | Antibiotics | | Natural | | |
| Bleomycin | Antibiotics | | Natural | | |
| Daunorubicin | Antibiotics | | Natural | | |
| Mitomycin | Antibiotics | | Natural | | |
| Idarubicin | Antibiotics | | Natural | | |
| Plicamycin | Antibiotics | | Natural | | |
| Vincristine | Plant alkaloids | Mitotic inhibitors | | | |
| Vinblastine | Plant alkaloids | Mitotic inhibitors | | | |
| Vinorelbine | Plant alkaloids | Mitotic inhibitors | | | |
| Etoposide | Plant alkaloids | inhibition of topoisomerase 1 | American Mayapple | High nM | |
| Teniposide | Plant alkaloids | inhibition of topoisomerase II | | Low nM | |
| Asparaginase | Enzyme | | | | |
| Maitotoxin | | activates Ca2+ permeable, non-selective cation channels | *Gambierdiscus toxicus* | | |
| Irinotecan (CPT-11) | Semi-synthetic alkaloid | inhibition of topoisomerase 1 | | | |
| Fumagillin Fumagalone Fumarranol O-(Chloroacetyl-carbamoyl)-Fumagillol (AGM-1470, TNP-470) | | angiogenesis inhibitor | *Aspergillus fumigatus* | | |
| 27-hydroxy-bullatacin | Acetogenins | | *A. glabra* | Low pM | |

In some embodiments, the drug is epothilone, auristatins, maytansine, dolastatins, laulimalide, meayamycin, 27-hydroxybullatacin, calicheamicin, or a derivative of any of the foregoing.

As used herein, the term "linker" means an organic moiety that connects two parts of a compound. Linkers typically comprise a direct bond or an atom such as oxygen or sulfur, a unit such as NH, C(O), C(O)NH, SO, SO$_2$, SO$_2$NH or a chain of atoms, such as substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, where one or more methylenes can be interrupted or terminated by O, S, S(O), SO$_2$, NH, C(O). The terms linker and spacer are used interchangeably herein.

In some embodiments, the linker comprises at least one (e.g., one, two, three, four, five, six, seven, eight, nine, ten or more) monomer for linking the platinum compound with the linker.

In some embodiments, the monomer for linking the platinum compound with the linker is a dicarbonyl compound. In some embodiments, the dicarbonyl monomer is

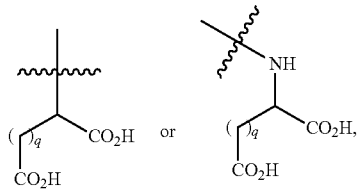

wherein q is 0, 1, 2, 3, 4, or 5. In some embodiments, q is 2.

In some embodiments, the dicarbonyl monomer is aspartic acid, wherein the aspartic acid is linked with the linker via the amino group of the aspartic acid, i.e., the dicarbonyl compound is

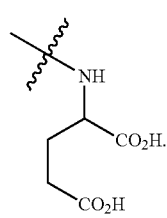

In some embodiments, the dicarbonyl monomer is —C(O)—R—CO$_2$H, wherein R is a bond, an optionally substituted C$_1$-C$_6$ alkylene, where the alkylene can comprise one or more double or triple bonds. In some embodiments, R is —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, or —CH$_2$CH$_2$CH$_2$CH$_2$CH$_2$CH$_2$—.

In some embodiments, the dicarbonyl monomer is a succinate monomer, wherein the succinic acid is linked to the linker via one of the carboxylic groups, i.e., the dicarbonyl monomer is

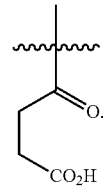

In some embodiments, for linking the platinum compound with the linker, the linker comprises a monomer of formula

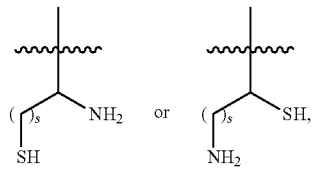

wherein s is 0, 1, 2, 3, 4, or 5. These monomers are also referred to as amino-thiol monomers herein.

In some embodiments, for linking the platinum compound with the linker, the linker comprises a monomer of formula

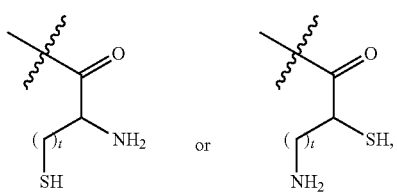

wherein t is 0, 1, 2, 3, 4, or 5. These monomers are also referred to as amino-thiol-carbonyl monomers herein.

In some embodiments, for linking the platinum compound with the linker, the linker comprises a monomer of formula

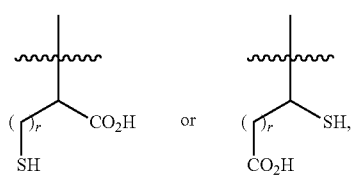

wherein r is 0, 1, 2, 3, 4, or 5.

In some embodiments, for linking the platinum compound with the linker, the linker comprises a monomer of formula

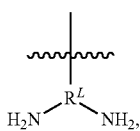

wherein $R^L$ is an optionally substituted linker, e.g. acyclic or cyclic linker. These monomers are also referred to as diamino monomers herein. A cyclic linker means a linking moiety that comprises at least one ring structure. Cyclic linkers can be aryl, heteroaryl, cyclyl or heterocyclyl. In some further embodiments of this, the monomer of formula

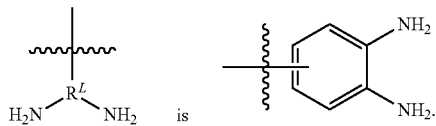

In still some further embodiments of this, the monomer of formula

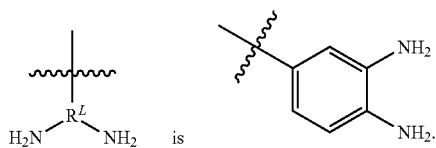

In some embodiments, the linker comprises at least one cleavable linking group. A cleavable linking group is one which is sufficiently stable outside the cell, but which upon entry into a target cell is cleaved to release the two parts the linker is holding together. In a preferred embodiment, the cleavable linking group is cleaved at least 10 times or more, preferably at least 100 times faster in the target cell or under a first reference condition (which can, e.g., be selected to mimic or represent intracellular conditions) than in the blood or serum of a subject, or under a second reference condition (which can, e.g., be selected to mimic or represent conditions found in the blood or serum).

Cleavable linking groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; amidases; endosomes or agents that can create an acidic environment, e.g., those that result in a pH of five or lower; enzymes that can hydrolyze or degrade an acid cleavable linking group by acting as a general acid, peptidases (which can be substrate specific) and proteases, and phosphatases.

A linker can include a cleavable linking group that is cleavable by a particular enzyme. The type of cleavable linking group incorporated into a linker can depend on the cell to be targeted. In some embodiments, cleavable linking group is cleaved at least 1.25, 1.5, 1.75, 2, 3, 4, 5, 10, 25, 50, or 100 times faster in the cell (or under in vitro conditions selected to mimic intracellular conditions) as compared to blood or serum (or under in vitro conditions selected to mimic extracellular conditions). In some embodiments, the cleavable linking group is cleaved by less than 90%, 80%, 70%, 60%, 50%, 40%, 30%, 20%, 10%, 5%, or 1% in the blood (or in vitro conditions selected to mimic extracellular conditions) as compared to in the cell (or under in vitro conditions selected to mimic intracellular conditions).

Exemplary cleavable linking groups include, but are not limited to, redox cleavable linking groups (e.g., —S—S— and —C(R)$_2$—S—S—, wherein R is H or $C_1$-$C_6$ alkyl and at least one R is $C_1$-$C_6$ alkyl such as $CH_3$ or $CH_2CH_3$); phosphate-based cleavable linking groups (e.g., —O—P(O)(OR)—O—, —O—P(S)(OR)—O—, —O—P(S)(SR)—O—, —S—P(O)(OR)—O—, —O—P(O)(OR)—S—, —S—P(O)(OR)—S—, —O—P(S)(ORk)-S—, —S—P(S)(OR)—O—, —O—P(O)(R)—O—, —O—P(S)(R)—O—, —S—P(O)(R)—O—, —S—P(S)(R)—O—, —S—P(O)(R)—S—, —O—P(S)(R)—S—, —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O—, —S—P(S)(H)—O—, —S—P(O)(H)—S—, and —O—P(S)(H)—S—, wherein R is optionally substituted linear or branched $C_1$-$C_{10}$ alkyl); acid celavable linking groups (e.g., hydrazones, esters, and esters of amino acids, —C=NN— and —OC(O)—); ester-based cleavable linking groups (e.g., —C(O)O—); peptide-based cleavable linking groups, (e.g., linking groups that are cleaved by enzymes such as peptidases and proteases in cells, e.g., —NHCHR$^A$C(O)NHCHR$^B$C(O)—, where $R^A$ and $R^B$ are the R groups of the two adjacent amino acids). A peptide based cleavable linking group comprises two or more amino acids. In some embodiments, the peptide-based cleavage linkage comprises the amino acid sequence that is the substrate for a peptidase or a protease found in cells.

In some embodiments, an acid cleavable linking group is cleaveable in an acidic environment with a pH of about 6.5 or lower (e.g., about 6.-, 5.5, 5.0, or lower), or by agents such as enzymes that acan act as a general acid.

In some embodiments, the linker comprises is an acid labile group, e.g., hydrazide or acetylphenoxy-butaonic. In some embodiments, the linker comprises an enzyme labile group e.g., maleimidecaproyl-valyl-citrullinyl-p-aminobenzylcarbamate.

In some embodiments, the linker comprises non-cleavable group e.g., a thio-ether linkage.

In some embodiments, the linker comprises a peptide, e.g., a dipeptide or a tripeptide.

In some embodiments, the linker comprises a disulfide linkage.

In some embodiments the linker comprises a self-immolative disulfide linkage.

In some embodiments, the linker is a bond.

It is to be understood that the linker can be modified to comprise functional groups for linking with the targeting moiety. Thus, in some embodiments, the linker comprises a functional group at one end (terminus) of the linker for linking the linker with the targeting moiety. When the linker comprises a functional group, the linker can be consider as F—B, wherein F is the functional group and B is linker without the functional group. Thus, the disclosure also provides targeting moiety (or ligand) drug conjugates described herein wherein the targeting moiety is absent, e.g., the bond linking the linker with the targeting moiety is replaced with a hydrogen.

As used herein, the functional group comprises at least two reactive moieties, one for connecting to the targeting moiety or ligand and the other for connecting to the linker. In some embodiments the functional group is thiol reactive, amine reactive or azide reactive. An example of a functional group is a group containing a thiol-reacting moiety and an amine-reacting moiety. Other examples of functional groups include aldehydes or ketones forming hydrazide linkages. In some embodiments, the functional group is maleimide group.

In some embodiments, the linker is a hydrocarbon, polyethylene glycol (PEG), an amino acid, a peptide, or a combination thereof. The hydrocarbon or PEG can be substituted or unsubstituted.

In some embodiments, the linker is a polyethylene glycol of a molecular weight of about 200 Da to about 50 kDa.

In some embodiments, the linker is comprises an optionally modified PEG and at least one amino acid, (e.g., one, two, three, four, five, six, seven, eight, nine, ten or more amino acids).

In some embodiments, the linker is comprises an optionally modified PEG and two amino acids, e.g., a dipeptide.

In some embodiments, the linker is comprises an optionally modified PEG and three amino acids, e.g., a tripeptide.

In some embodiments, the linker comprises at least one lysine residue.

In some embodiments, the linker is

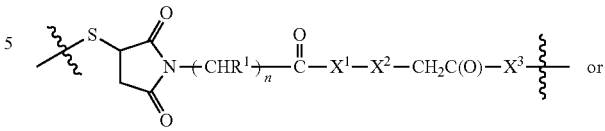

or

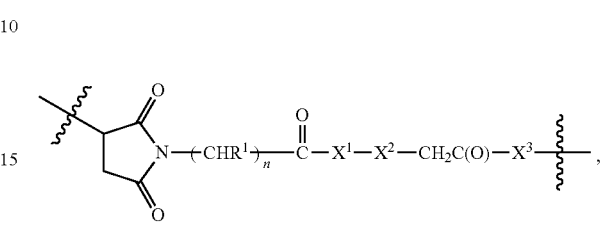

wherein each $R^1$ is independently H, alkyl (e.g., $C_1$-$C_6$ alkyl), or aryl; $X^1$ is NH, O, or S; $X^2$ is a polyethylene glycol; and $X^3$ is an amino acid or a peptide comprising from two to ten amino acids. Without limitations, $X^3$ can comprise natural and/or unnatural amino acids.

In some embodiments, $X^1$ is NH.

In some embodiments, $X^2$ is —$(CH_2CH_2O)_a$—, wherein a is from 3 to 100.

In some embodiments, $X^3$ is an amino acid, a dipeptide, or a tripeptide. In some embodiments, $X^3$ is -Lys-Z—, -Lys-Lys-Z—, -Lys-Lys-Lys-Z—, -Lys-Ala-Lys-Z—, wherein Z is succinic acid, aspartic acid, serine, threonine, a dicarbonyl monomer described herein, an amino-thiol monomer described herein, an amino-thiol-carbonyl monomer described herein, or a diamino monomer described herein.

In some embodiments, the linker is

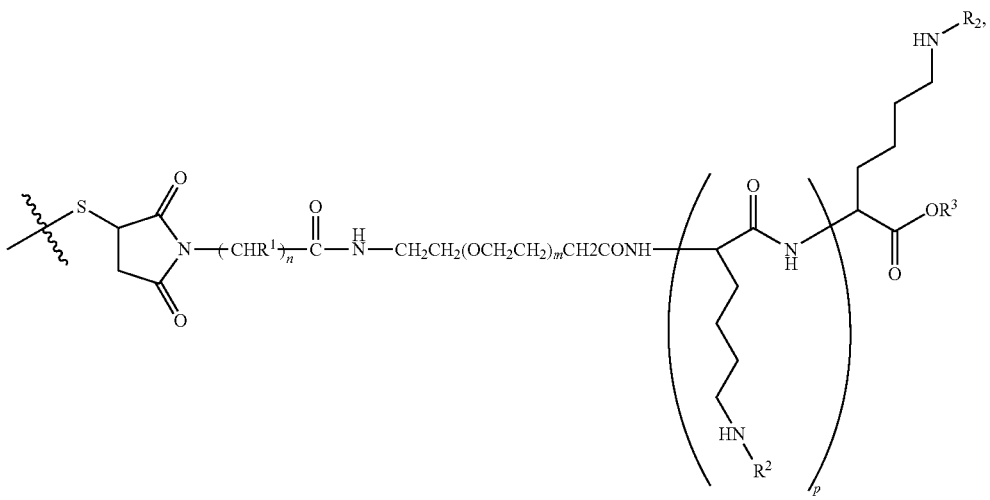

-continued
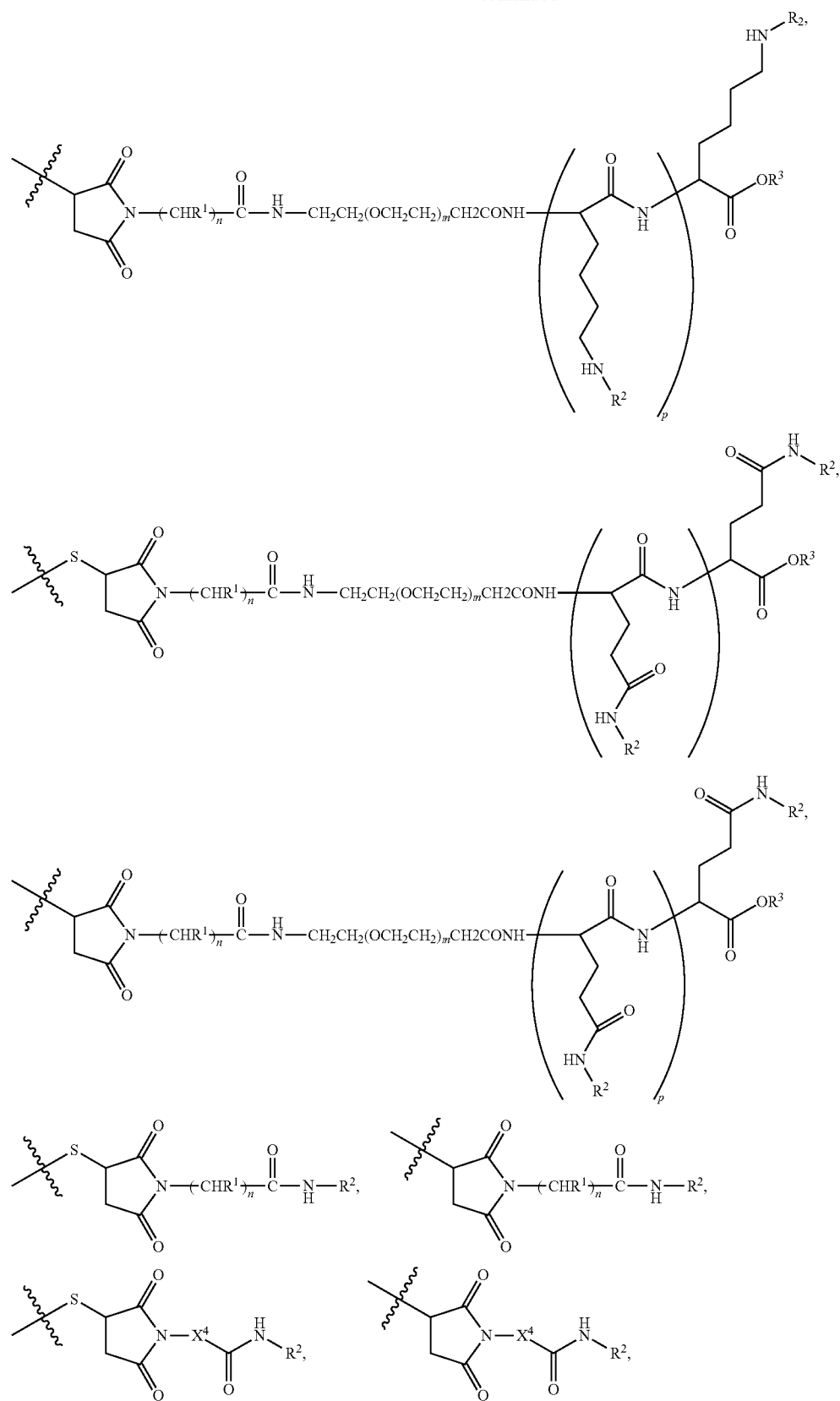

-continued

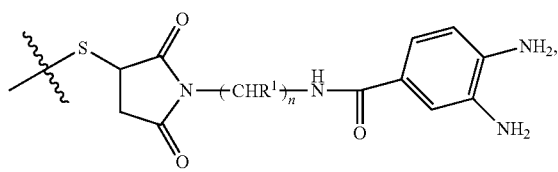

wherein each $R^1$ is independently H, alkyl (e.g., $C_1$-$C_6$ alkyl), or aryl; $R^2$ is a mono or dicarboxylic acid, a dicarbonyl monomer described herein, an amino-thiol monomer described herein, an amino-thiol-carbonyl monomer described herein, or a diamino monomer described herein; $R^3$ is H, alkyl, or aryl; n is 0, 1, 2, 3, 4, or 5; $X^4$ is polyethylene glycol; p is 1, 2, or 3; and m is 2-100.

In some embodiments, $R^1$ is H.

In some embodiments, $R^2$ is succinic acid, aspartic acid, serine, or threonine.

In some embodiments, $R^2$ is

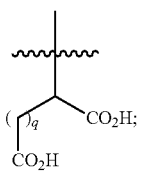

—C(O)—R—$CO_2H$, wherein R is a bond, an optionally substituted $C_1$-$C_6$ alkylene, where the alkylene can comprise one or more double or triple bonds;

wherein s is 0, 1, 2, 3, 4, or 5;

wherein t is 0, 1, 2, 3, 4, or 5;

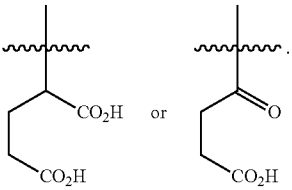

wherein r is 0, 1, 2, 3, 4, or 5; or

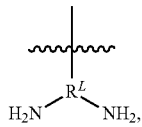

wherein $R^L$ is an optionally substituted linker, e.g. acyclic or cyclic linker. A cyclic linker means a linking moiety that comprises at least one ring structure. Cyclic linkers can be aryl, heteroaryl, cyclyl or heterocyclyl. In some further embodiments of this, the monomer of formula

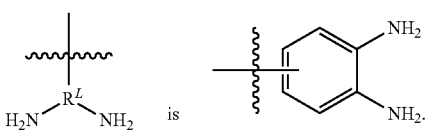

In still some further embodiments of this, the monomer of formula

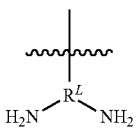

is

In some embodiments, $R^2$ is

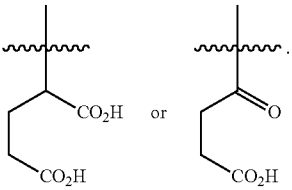 [SMILES: *C(CCC(=O)O)C(=O)O ; *C(=O)CCC(=O)O]

In some embodiments, $R^3$ is H or methyl.
In some embodiments, n is 2.
In some embodiments, p is 1.

In some embodiments, the linker is
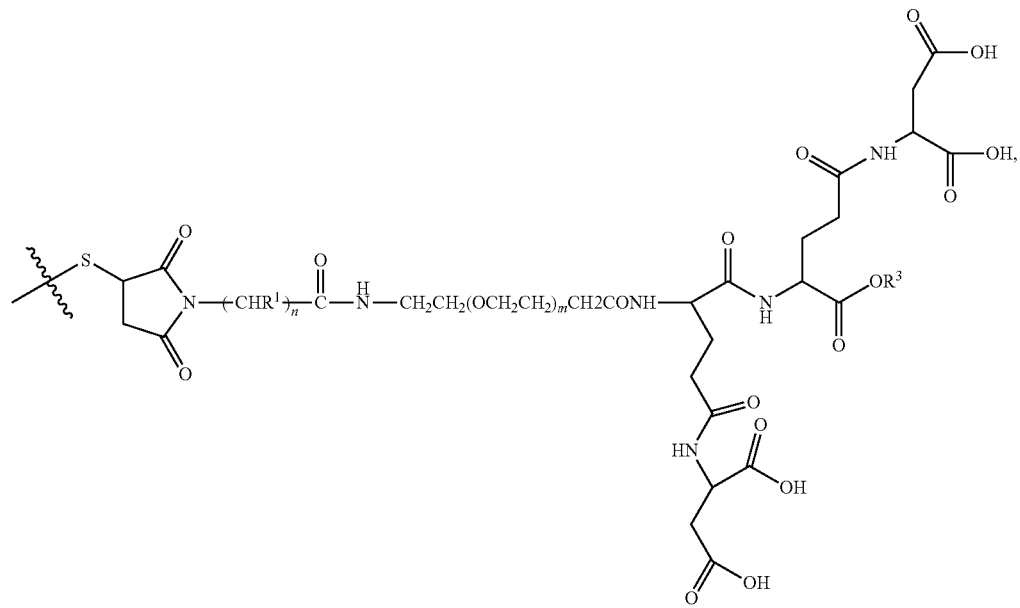
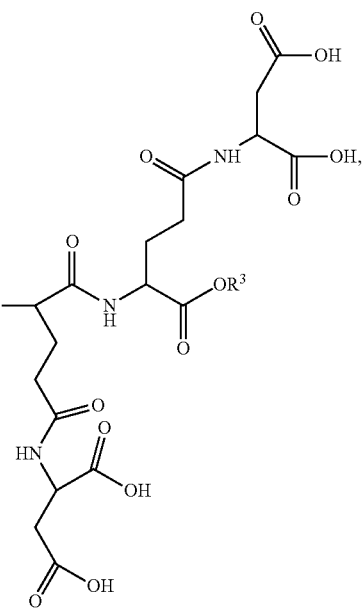

-continued
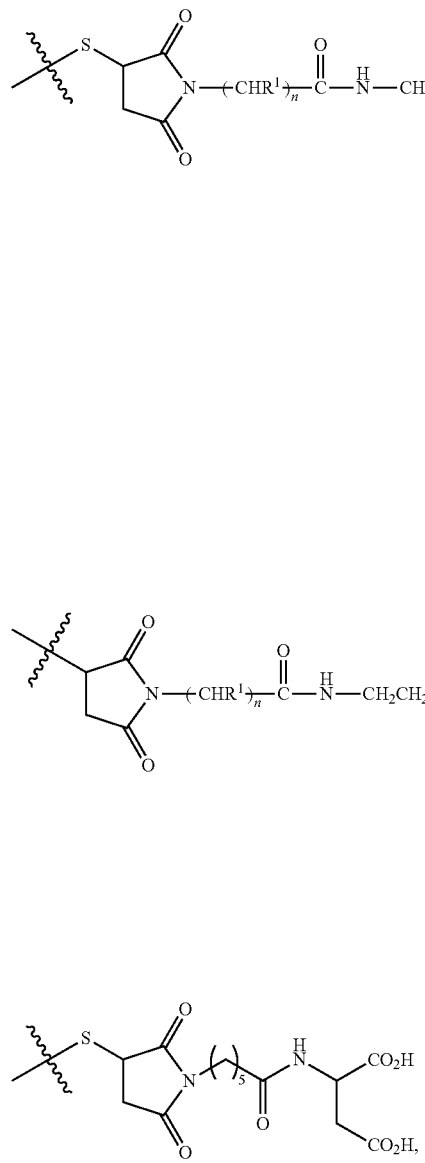
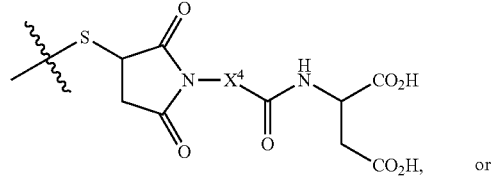 or 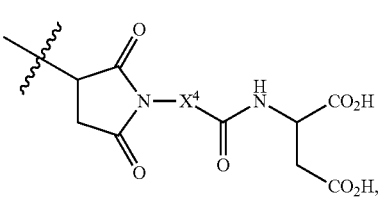
wherein variables are as defined above.

In some embodiments, the linker is

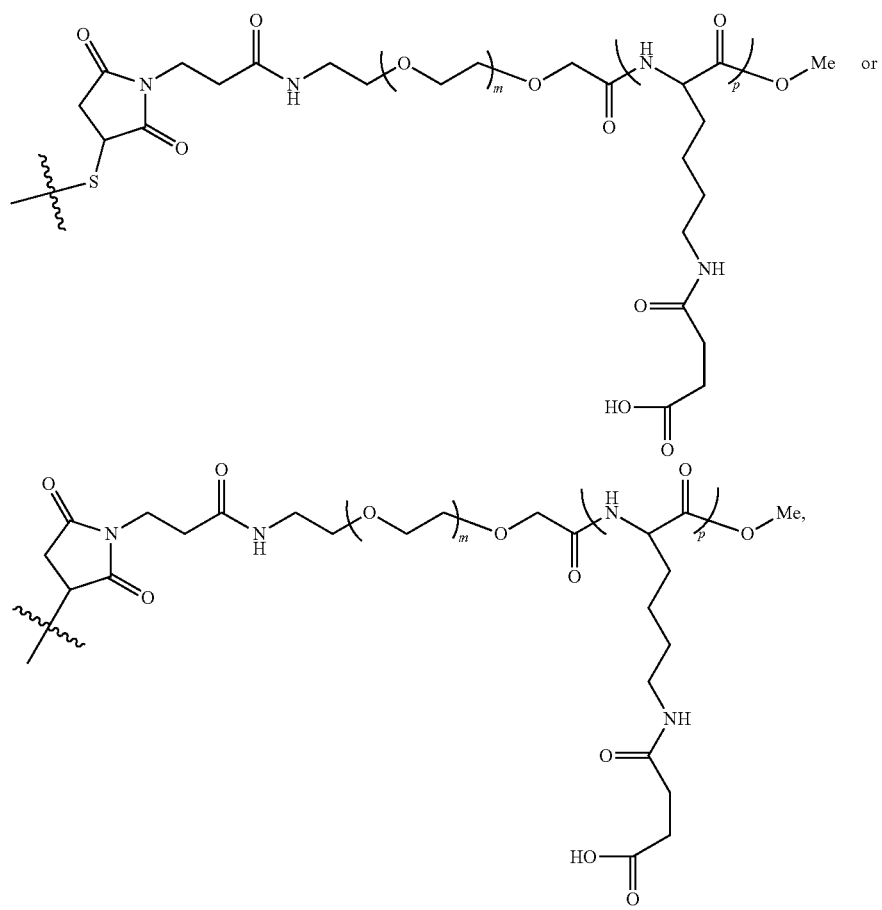

wherein p is 1, 2, or 3; and m is 2-100.

In the above shown structures, the moieties

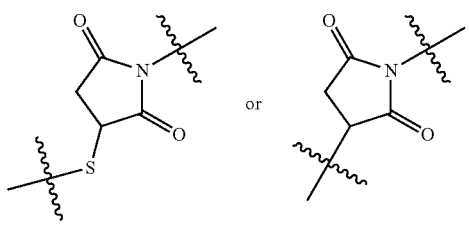 [SMILES: *SC1CC(=O)N(*)C1=O ; *C1CC(=O)N(*)C1=O]

can be replaced by a maleimide (e.g.,

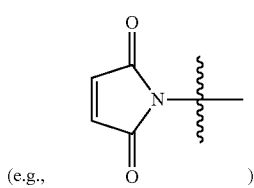 [SMILES: *N1C(=O)C=CC1=O]

)

group to form a linker having a functional group at one end, e.g., conjugates of formula F—B, F—B—C, or F—B—C—B'-D, wherein F is functional group, B is a linker, C is platinum compound, and D is a drug.

In some embodiments, the linker comprises a co-ordination metal complex, e.g., the linker is —B—C—B'-, wherein are B and B' are independently a linker and C is coordination metal complex. The coordination metal complex can either form part of the linker backbone or be present as a sidechain to the linker backbone. Exemplary co-ordination metal complexes include complexes of Pt, Fe, Si and the like. For example the co-ordination complex can comprise tetraamminecopper(II) sulphate, iron, or silicon. Thus, as used herein, the linker can also include a Pt(II) coordination complex capable of being covalently bonded to a drug or cytotoxic agent. The drug can be attached to the platinum coordination complex via an amide, ester, amine, ether, hydrazide, disulfides or imine linkages.

In some embodiments, the co-ordination metal complex is a platinum complex. In some embodiments, the complex comprises at least one coordination bond.

In some embodiments, the platinum complex is

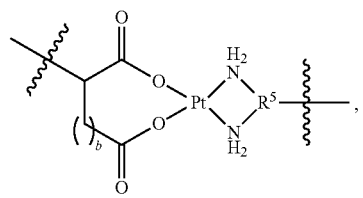

wherein b is 0, 1, 2, 3, 4, or 5 and $R^5$ is a cyclic or acyclic linker joining the two amino groups to rest of the linker. In some embodiments, b is 1.

In some embodiments, $R^5$ is

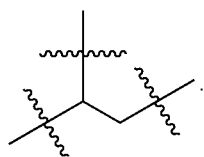 [SMILES: *CC(*)*]

In some embodiments, $R^5$ is a cyclic linker selected from aryl, heteroaryl, cyclyl or heterocyclyl. In some embodiments, the platinum complex is

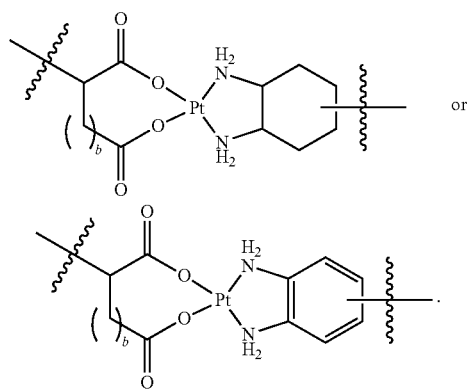

or

In one embodiment, the platinum complex is

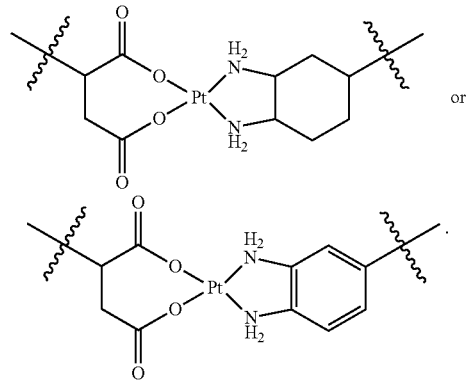

In one embodiment, the platinum complex is

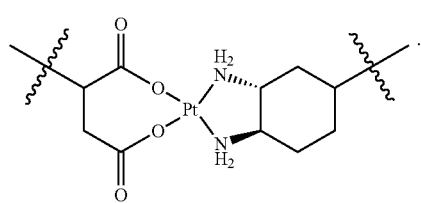

In some embodiments, the platinum complex is

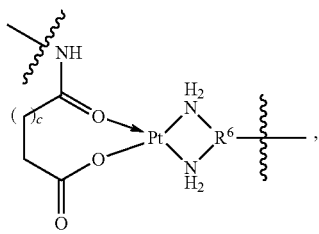

wherein c is 0, 1, 2, 3, 4, or 5 and $R^6$ is a cyclic or acyclic linker joining the two amino groups to rest of the linker. In some embodiments, c is 1.

In some embodiments, $R^6$ is

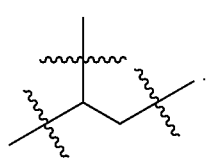

In some embodiments, $R^6$ is a cyclic linker selected from aryl, heteroaryl, cyclyl or heterocyclyl. In some embodiments, the platinum complex is

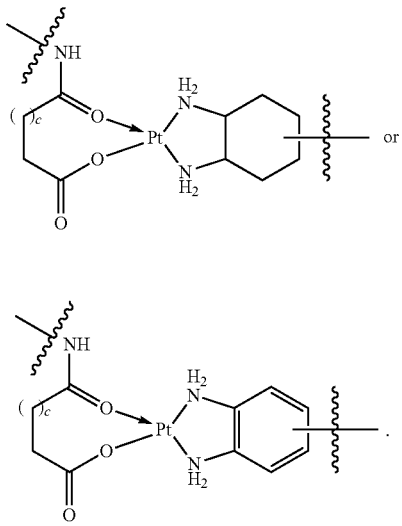

In one embodiment, the platinum complex is

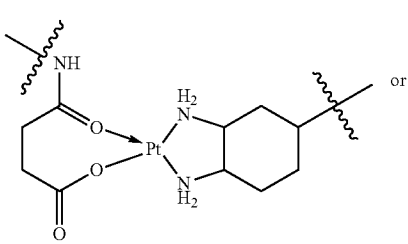

-continued

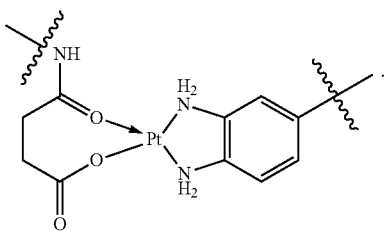

In some embodiments, the platinum complex is

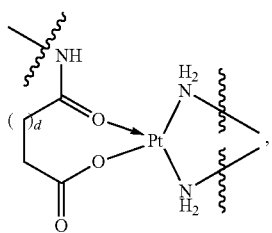

wherein d is 0, 1, 2, 3, 4, or 5. In some embodiments, d is 1.

In some embodiments, the platinum complex is

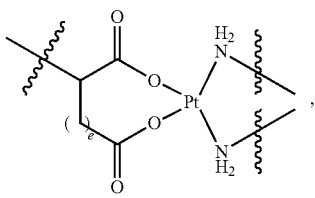

wherein e is 0, 1, 2, 3, 4, or 5. In some embodiments, e is 1.

In some embodiments, the platinum complex is

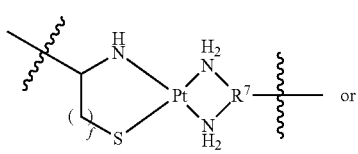

or

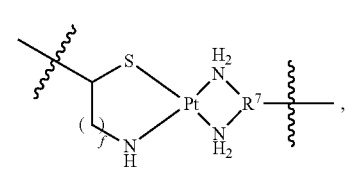

wherein f is 0, 1, 2, 3, 4, or 5 and $R^7$ is a cyclic or acyclic linker joining the two amino groups to rest of the linker.

In one embodiment, f is 1.

In some embodiments, $R^7$ is

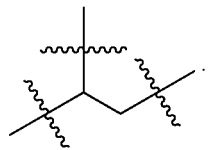 [SMILES: *CC(*)*]

In some embodiments, $R^7$ is a cyclic linker selected from aryl, heteroaryl, cyclyl or heterocyclyl.

In some embodiments, the platinum complex is

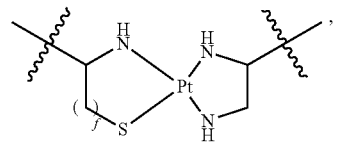

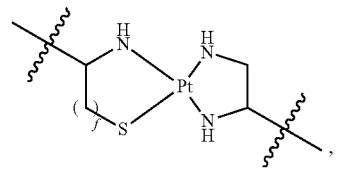

, or

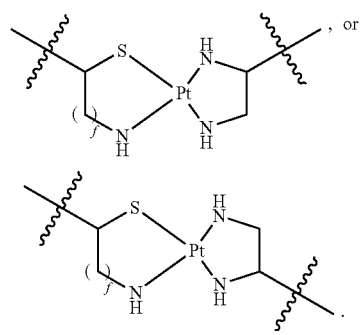

In some embodiments, the platinum complex is

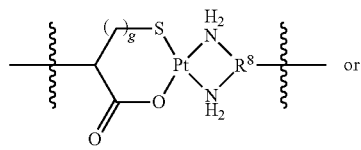

or

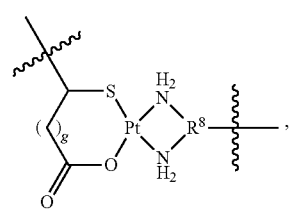

wherein g is 0, 1, 2, 3, 4, or 5 and $R^8$ is a cyclic or acyclic linker joining the two amino groups to rest of the linker. In one embodiment g is 1

In some embodiments, $R^8$ is

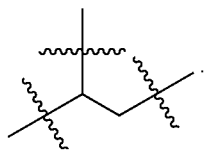 [SMILES: *CC(*)*]

In some embodiments, $R^8$ is a cyclic linker selected from aryl, heteroaryl, cyclyl or heterocyclyl.

In some embodiments, the platinum complex is

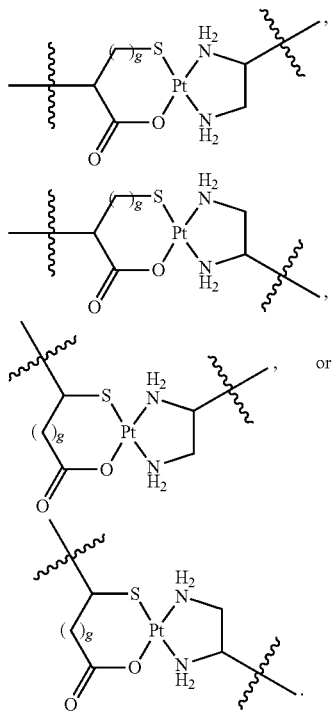

In some embodiments, the platinum complex is

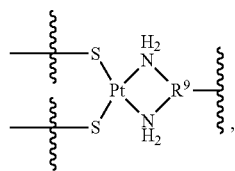

wherein $R^9$ is a cyclic or acyclic linker joining the two amino groups to rest of the linker. In some embodiments, $R^9$ is

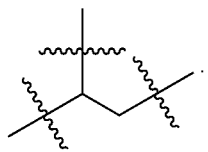 [SMILES: *CC(*)*]

In some embodiments, $R^9$ is a cyclic linker selected from aryl, heteroaryl, cyclyl or heterocyclyl. In one embodiments, the platinum complex is

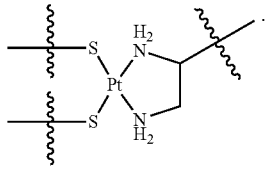

As used herein the term "targeting moiety" or "targeting ligand" refers to any molecule that provides an enhanced affinity for a selected target, e.g., a cell, cell type, tissue, organ, region of the body, or a compartment, e.g., a cellular, tissue or organ compartment. The targeting moiety or ligand can comprise a wide variety of entities. Such ligands can include naturally occurring molecules, or recombinant or synthetic molecules.

Exemplary targeting ligands include, but are not limited to, antibodies, fragments of anitbodiesantigens, folates, receptor ligands, carbohydrates, aptamers, integrin receptor ligands, chemokine receptor ligands, transferrin, biotin, serotonin receptor ligands, PSMA, endothelin, GCPII, somatostatin, LDL and HDL ligands. Additional exemplary ligands include, but are not limited to, polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG, e.g., PEG-2K, PEG-5K, PEG-10K, PEG-12K, PEG-15K, PEG-20K, PEG-40K), MPEG, [MPEG]$_2$, polyvinyl alcohol (PVA), polyurethane, poly(2-ethylacryllic acid), N-isopropylacrylamide polymers, polyphosphazine, polyethylenimine, cationic groups, spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, thyrotropin, melanotropin, lectin, glycoprotein, surfactant protein A, mucin, glycosylated polyaminoacids, transferrin, bisphosphonate, polyglutamate, polyaspartate, aptamer, asialofetuin, hyaluronan, procollagen, immunoglobulins (e.g., antibodies), insulin, transferrin, albumin, sugar-albumin conjugates, intercalating agents (e.g., acridines), cross-linkers (e.g. psoralen, mitomycin C), porphyrins (e.g., TPPC4, texaphyrin, Sapphyrin), polycyclic aromatic hydrocarbons (e.g., phenazine, dihydrophenazine), artificial endonucleases (e.g., EDTA), lipophilic molecules (e.g, steroids, bile acids, cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid,O3-(oleoyl)lithocholic acid, O3-(oleoyl)cholenic acid, dimethoxytrityl, or phenoxazine), peptides (e.g., an alpha helical peptide, amphipathic peptide, RGD peptide, cell permeation peptide, endosomolytic/fusogenic peptide), alkylating agents, phosphate, amino, mercapto, polyamino, alkyl, substituted alkyl, radiolabeled markers, enzymes, haptens (e.g. biotin), transport/absorption facilitators (e.g., naproxen, aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, AP, antibodies, hormones and hormone receptors, lectins, carbohydrates, multivalent carbohydrates, vitamins (e.g., vitamin A, vitamin E, vitamin K, vitamin B, e.g., folic acid, B12, riboflavin, biotin and pyridoxal), vitamin cofactors, lipopolysaccharide, an activator of p38 MAP kinase, an activator of NF-κB, taxon, vincristine, vinblastine, cytochalasin, nocodazole, japlakinolide, latrunculin A, phalloidin, swinholide A, indanocine, myoservin, tumor necrosis factor alpha (TNFalpha), interleukin-1 beta, gamma interferon, natural or recombinant low density lipoprotein (LDL), natural or recombinant high-density lipoprotein (HDL), and a cell-permeation agent (e.g., a.helical cell-permeation agent).

Peptide and peptidomimetic ligands include those having naturally occurring or modified peptides, e.g., D or L peptides; α, β, or γ peptides; N-methyl peptides; azapeptides; peptides having one or more amide, i.e., peptide, linkages replaced with one or more urea, thiourea, carbamate, or sulfonyl urea linkages; or cyclic peptides. A peptidomimetic (also referred to herein as an oligopeptidomimetic) is a molecule capable of folding into a defined three-dimensional structure similar to a natural peptide. The peptide or peptidomimetic ligand can be about 5-50 amino acids long, e.g., about 5, 10, 15, 20, 25, 30, 35, 40, 45, or 50 amino acids long.

Carbohydrate based targeting ligands include, but are not limited to, D-galactose, multivalent galactose, N-acetyl-D-galactose (GalNAc), multivalent GalNAc, e.g. GalNAc2 and GalNAc3; D-mannose, multivalent mannose, multivalent lactose, N-acetyl-galactosamine, N-acetyl-gulucosamine, multivalent fucose, glycosylated polyaminoacids and lectins. The term multivalent indicates that more than one monosaccharide unit is present. Such monosaccharide subunits can be linked to each other through glycosidic linkages or linked to a scaffold molecule.

A number of folate and folate analogs amenable to the present invention as ligands are described in U.S. Pat. Nos. 2,816,110; 5,552,545; 6,335,434 and 7,128,893, contents of all of which are herein incorporated in their entireties by reference.

In some embodiments, the targeting ligand binds a protein, receptor, or marker expressed on the surface of a cancer cell.

In some embodiments, the targeting ligand binds EGFR.

In some embodiments, the targeting ligand is a polyclonal or monoclonal antibody or a fragment thereof retaining epitope binding activity or an antibody-based binding moiety.

In some embodiments, the targeting ligand is a polyclonal or monoclonal antibody, antibody fragments, a peptide, or a molecule that is capable of binding protein receptors expressed on the surface of cancer cells.

As used herein, the term "antibody-based binding moiety" or "antibody" can include immunoglobulin molecules and immunologically active determinants of immunoglobulin molecules, e.g., molecules that contain an antigen binding site which specifically binds to the fusion protein. The term "antibody-based binding moiety" is intended to include whole antibodies, e.g., of any isotype (IgG, IgA, IgM, IgE, etc), and includes fragments thereof which are also specifically bind with the fusion protein or a fragment thereof. Antibodies can be fragmented using conventional techniques. Thus, the term includes segments of proteolytically-cleaved or recombinantly-prepared portions of an antibody molecule that are capable of selectively reacting with a certain protein. Non-limiting examples of such proteolytic and/or recombinant fragments include Fab, F(ab')2, Fab', Fv, dAbs and single chain antibodies (scFv) containing a VL and VH domain joined by a peptide linker. The scFv's can be covalently or non-covalently linked to form antibodies having two or more binding sites. Thus, "antibody-based binding moiety" includes polyclonal, monoclonal, or other purified preparations of antibodies and recombinant antibodies. The term "antibody-based binding moiety" is further intended to include humanized antibodies, bispecific antibodies, and chimeric molecules having at least one antigen binding determinant derived from an antibody molecule.

In some embodiments, the targeting ligand is an antibody selected from the group consisting of C242 antibody (CanAg), Rituximab, Trastuzumab (Her2), Cetuximab, Bevacizumab (VEGF), Panitumumab, Alemtuzumab, Ofatumumab, Gemtuzumab (CD33), Inotuzumab (CD22), Lorvotuzumab (CD56), Brentuximab (CD30), Glembatumumab (GPNMB), epitope bind fragments thereof and any combinations thereof.

In some embodiments, the ligand drug conjugate is an antibody-drug conjugate (ADC) wherein the ligand is an antibody having specificity for a tumor-associated antigen (TAA) and the drug is a Pt(II) chemotherapeutic agent. The linker is cleavable inside the cell upon internalization. Treatment with the ADC leads to inhibition of tumor growth. The invention also relates to groups useful for stabilizing chemotherapeutic agents and markers. Stabilizing groups, such as, for example, PEG, limit clearance and metabolism of the chemotherapeutic agent or marker by enzymes that may be present in blood or non-target tissue. Stabilizing groups may serve to block degradation of the chemotherapeutic agent or marker and may also provide other physical characteristics of the agent or marker, for example, increasing the solubility of the ligand drug conjugate or decreasing the aggregation properties of the ligand drug conjugate. The stabilizing group may also improve the stability of the chemotherapeutic agent or marker during storage in either a formulated or non-formulated form.

Figure 1B:
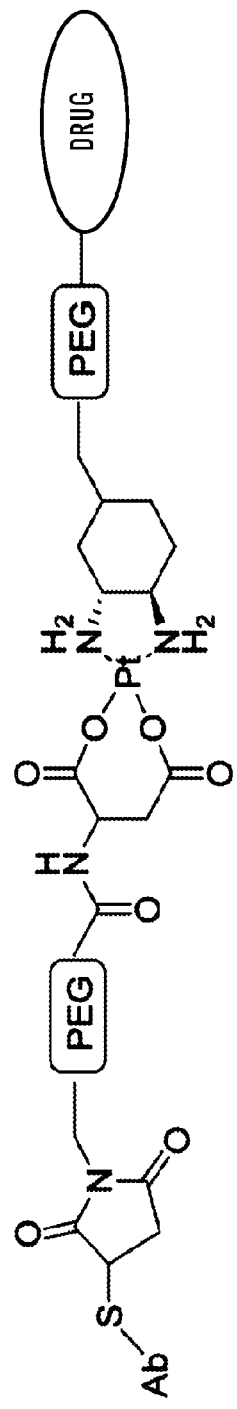
FIG. 1B shows a general structure of a ligand-drug conjugate where platinum acts as a linker by forming dicarboxylato linkages. It is flanked on either side by a PEG spacer.
Figure 1C:
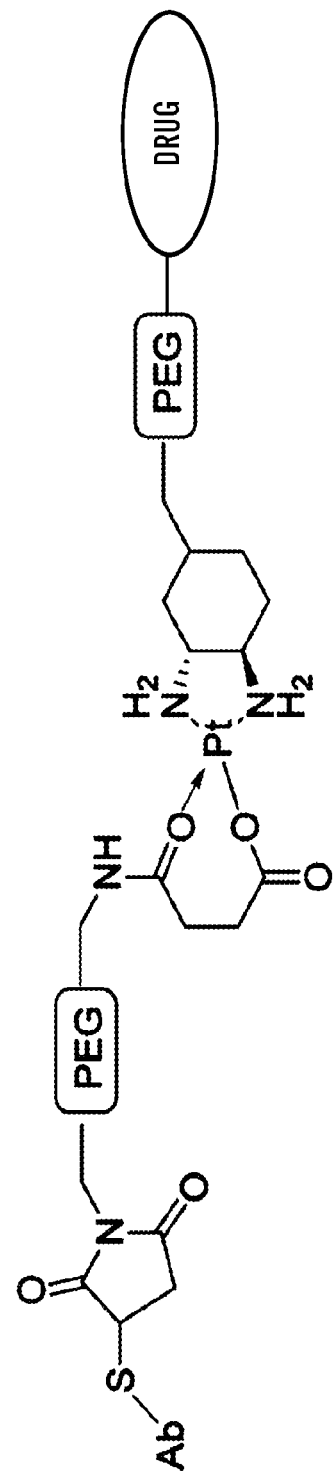
FIG. 1C shows a general structure of a ligand-drug conjugate where platinum acts as a linker by forming a monocarboxylato and O→Pt coordinate bond. It is flanked on either side by a PEG spacer.
Figure 1D:
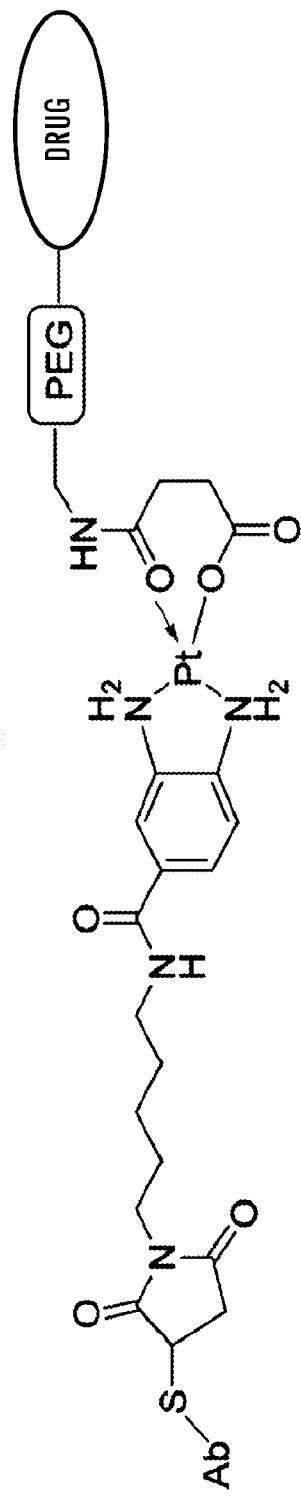
FIGS. 1D-1F show general structures of some exemplary ligand-drug conjugates.
Figure 1E:
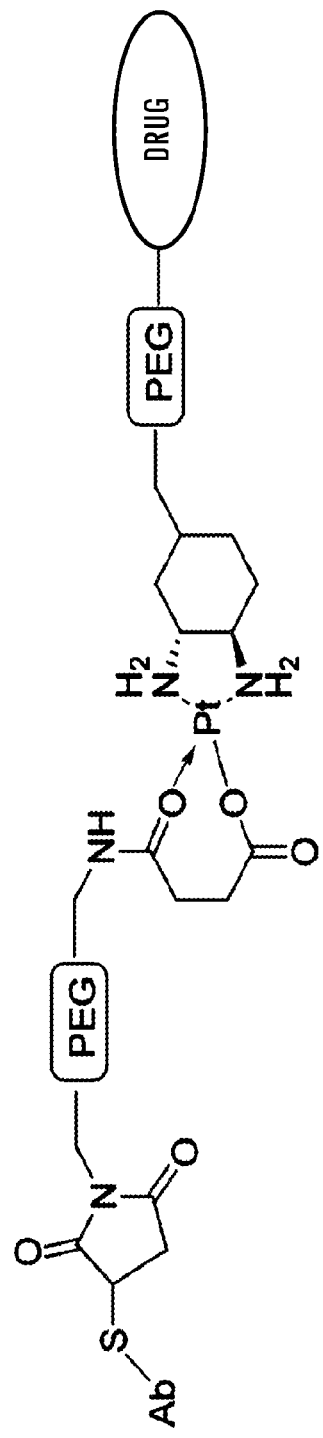
Figure 1F:
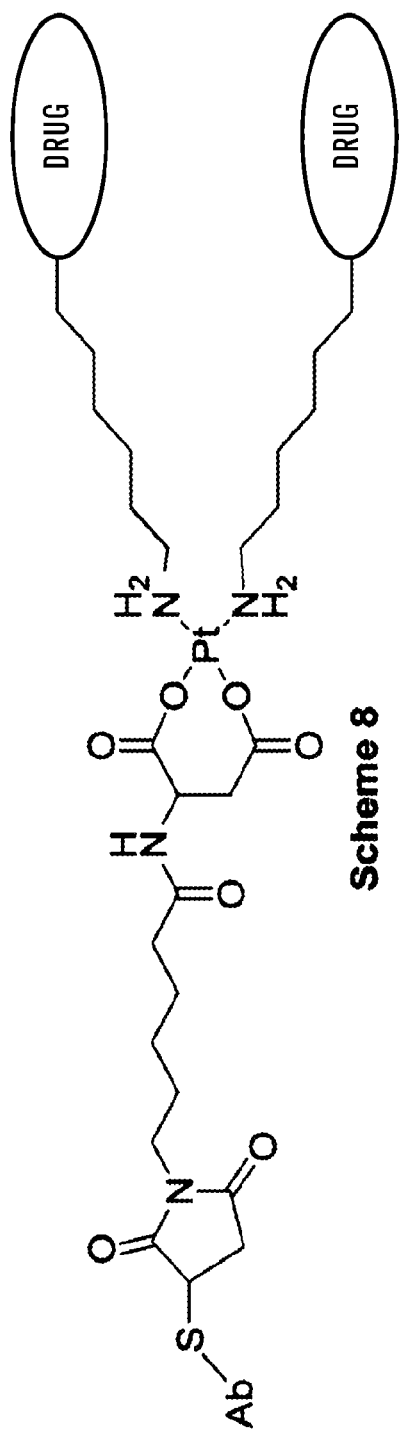

An example of the LDC where the drug is linked via Pt coordination complex is shown in FIGS. 1A-1C.

In one embodiment of the present invention, the functional group is a maleimide group which is bonded with the ligand through a thioether linkage and is bonded to the linker via the nitrogen atom of the maleimide group. This embodiment is shown in Formula 2:

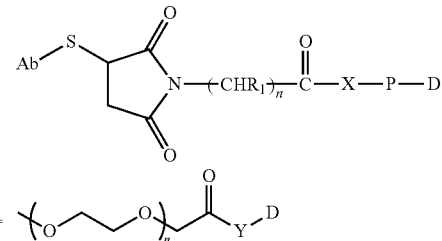

Formula 2

Y = Lys-Z, Lys-Lys-Z, Lys-Ala-Lys-Z
Z = Succinic acid, Aspartic acid
Serine, threonine etc
Ab = Antibody wherein:
(CHR$_1$)n-C(=O)—X—P represents the linker, X is N or O, P is a PEG-containing peptide of natural or unnatural amino acids (Y), wherein PEG may be linear or branched PEG (n=2-100). One end of the linker contains a functional group capable of bonding with thiols or amines, while the other end is a reactive carboxylic acid or amine capable of forming a covalent linkage with the drug.
D represents the drug that is coupled to the linker through ester, amide, disulfide, hydrazide or thioether linkage.
Y can be a single amino acid, di- or tri-peptide of lysine or other natural or unnatural amino acids, which could be connected with a chelating group (R2) for platinum as shown in Compound 1

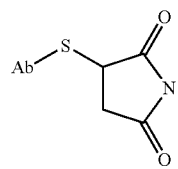
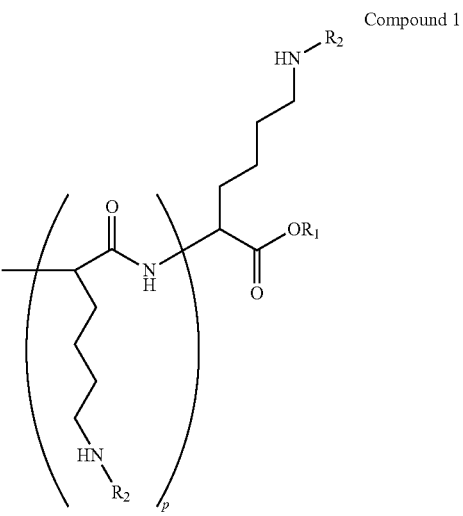

Compound 1

$R_1$ = H, alkyl, aryl group
$R_2$ = mono or dicarboxylic acid
$p$ = 1-3
$m$ = 2-100
Ab = Antibody In another embodiment, R2 is an entity with dicarboxylate groups such as aspartic acid or any other dicarboxylic acid (Compound 2).

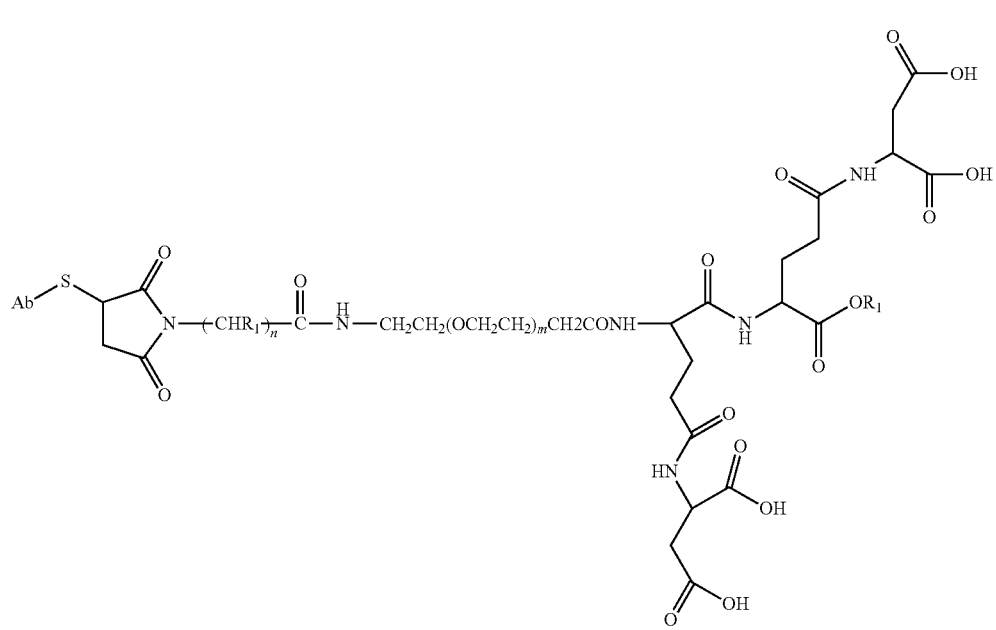

Compound 2

$R_1$ = H, alkyl, aryl group
$n$ = 1-3
$m$ = 2-100
Ab = Antibody

In yet another embodiment, R2 as depicted in compound 1 could also be an entity with a monocarbonyl group, such as an amide group and succinic acid, or any combinations thereof, as shown in Compound 3.

Figure 3:
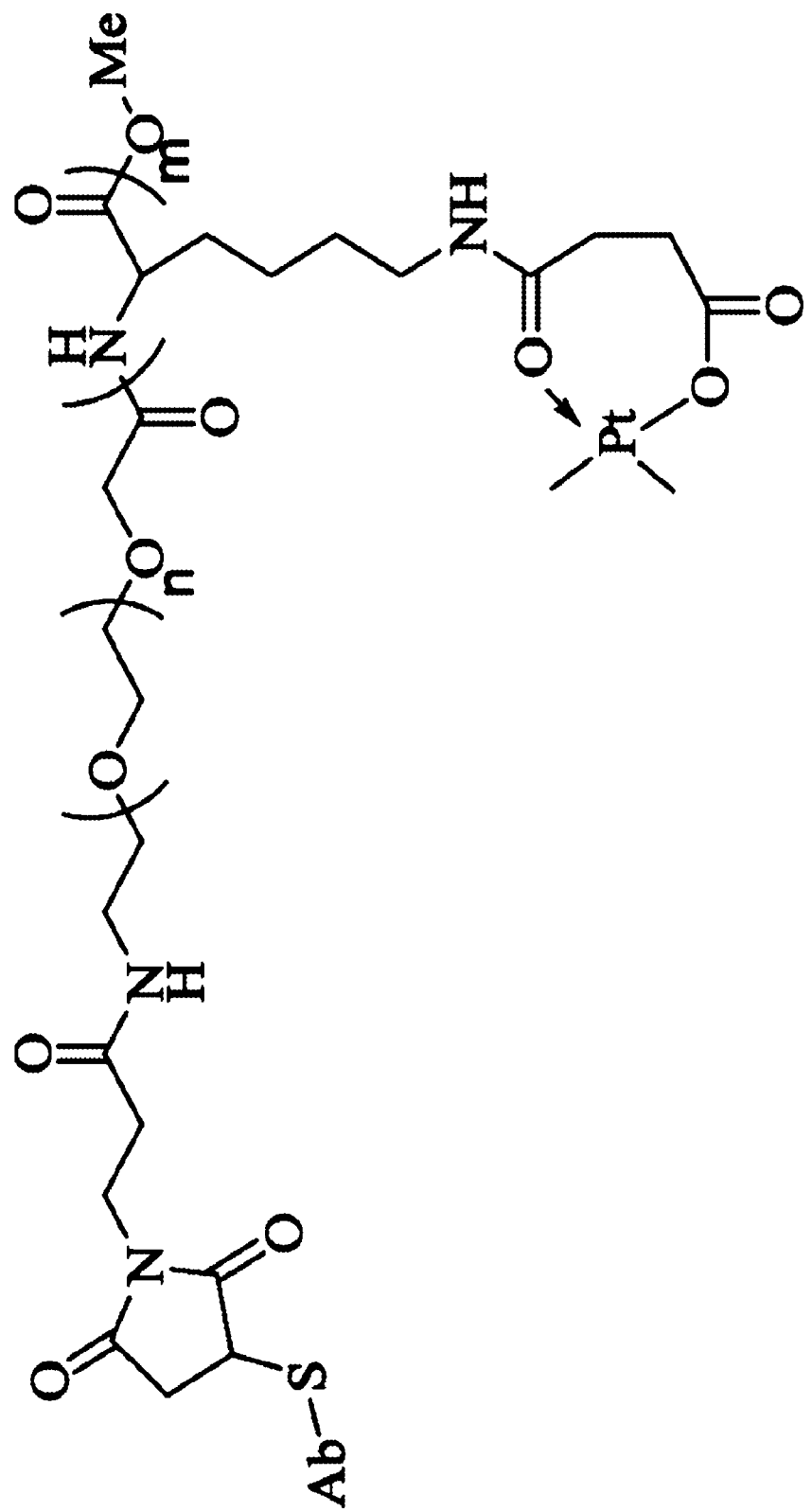
FIG. 3 shows a general structure of a cisplatin/oxaliplatin based antibody-drug conjugates (ADC) where linker lysine is conjugated to PEG with α-amine.

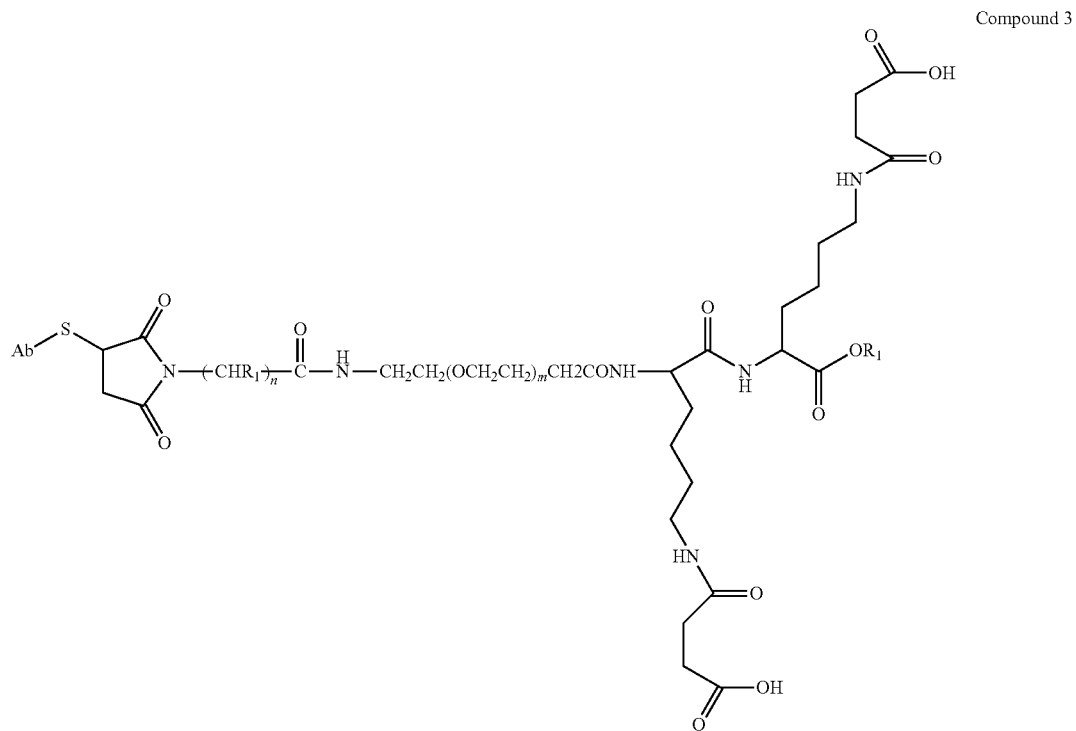
Compound 3
$R_1$ = H, alkyl, aryl group
$n$ = 1-3
$m$ = 2-100
Ab = Antibody
In a further embodiment, the platinum (II) drug can be coupled to the dicarboxylate group through two oxygen atoms as shown in Compound 4.
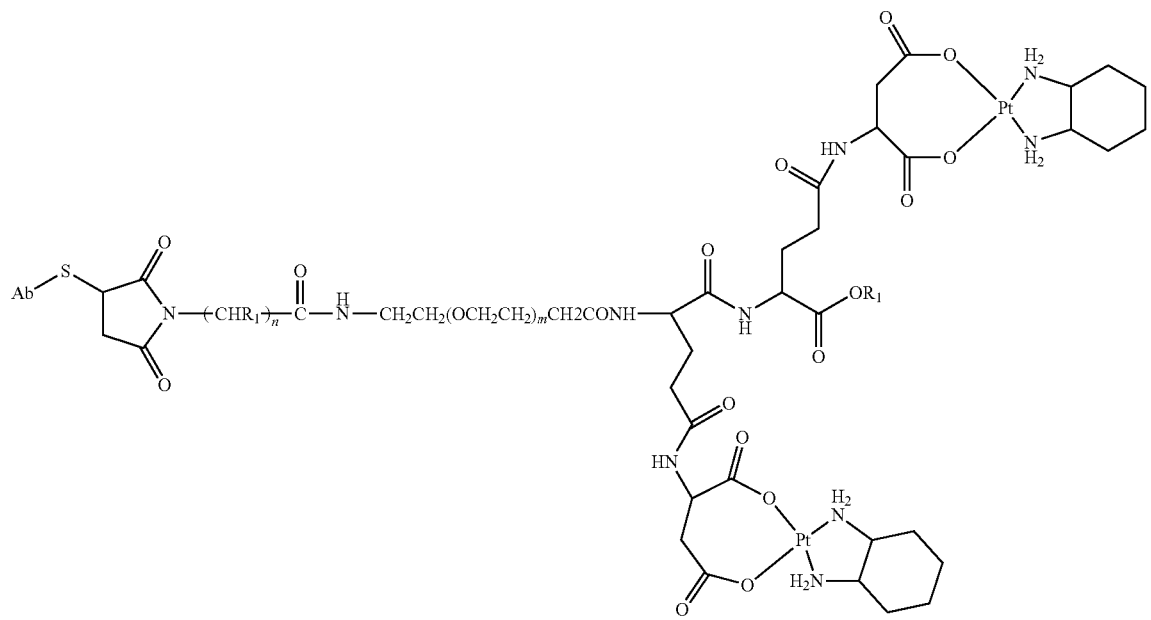
Compound 4
$R_1$ = H, alkyl, aryl group
$n$ = 1-3
$m$ = 2-100
Ab = Antibody Further, the ligand-targeted molecule is complexed to platinum by the succinate through monocarboxylato and O→Pt coordinate bond. The Pt (II)-agent in the conjugate is covalently attached to a bifunctional lysine linker and the number of bifunctional lysines is p (p=1-3), as shown below in Compound 5.

in FIG. 3, wherein linker lysine is conjugated to PEG with α-amine; m=1-3; and n=2-100.

Figure 2:
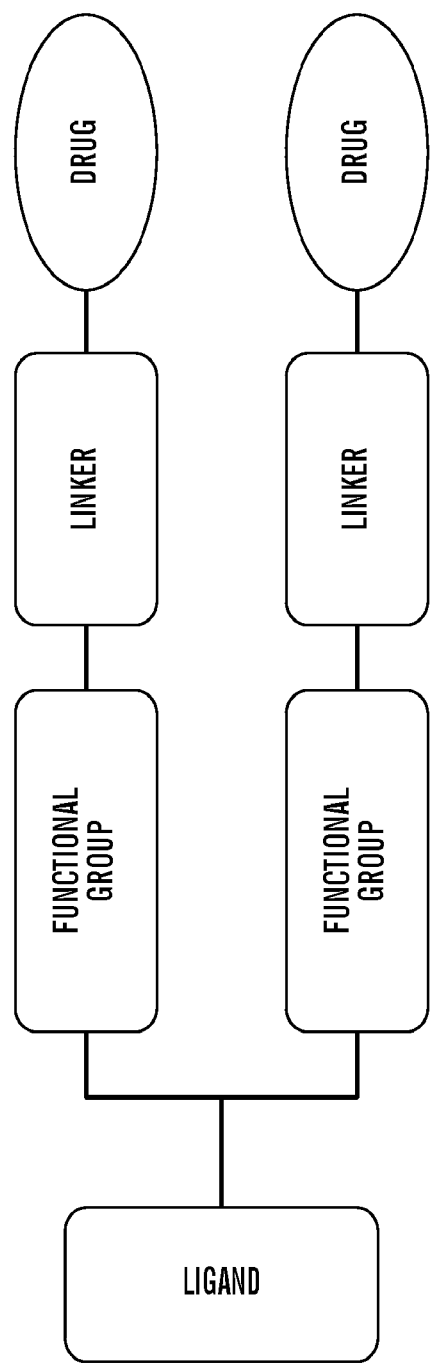
FIG. 2 shows a general structure of a ligand-drug conjugate containing two linker-drug complex.
Figure 4:
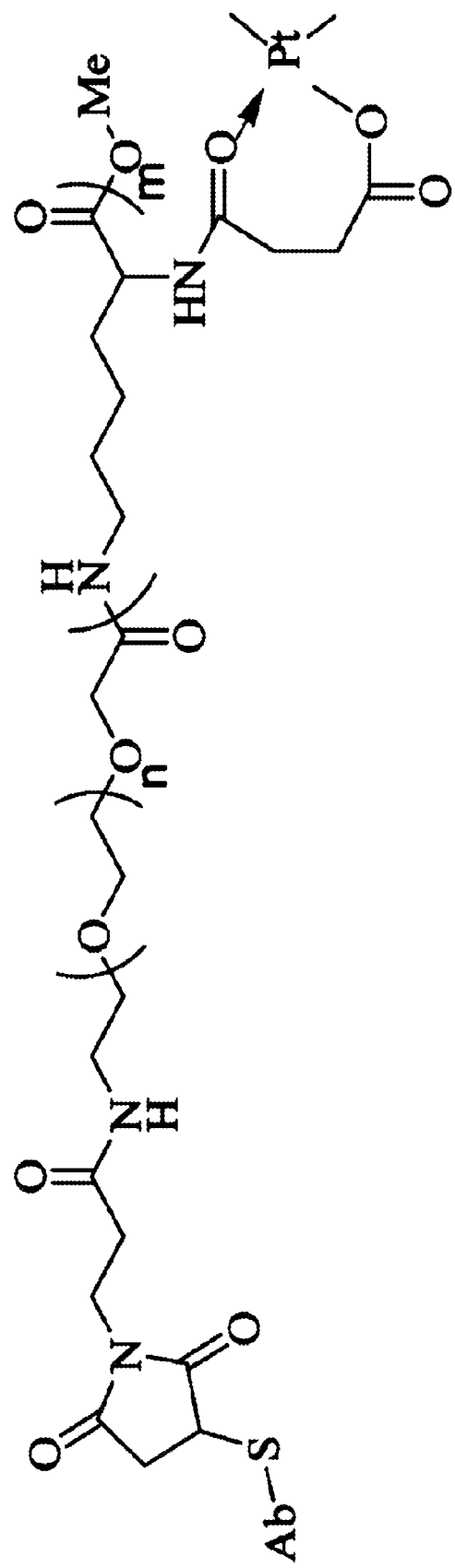
FIG. 4 shows a general structure of a cisplatin/oxaliplatin based ADC where linker lysine is conjugated to PEG with ε-amine.

In some embodiments, a LDC of FIG. 2 is a cisplatin/oxaliplatin based antibody-drug conjugate (ADC) as shown in FIG. 4, wherein linker lysine is conjugated to PEG with ε-amine; m=1-3; and n=2-100.

Compound 5

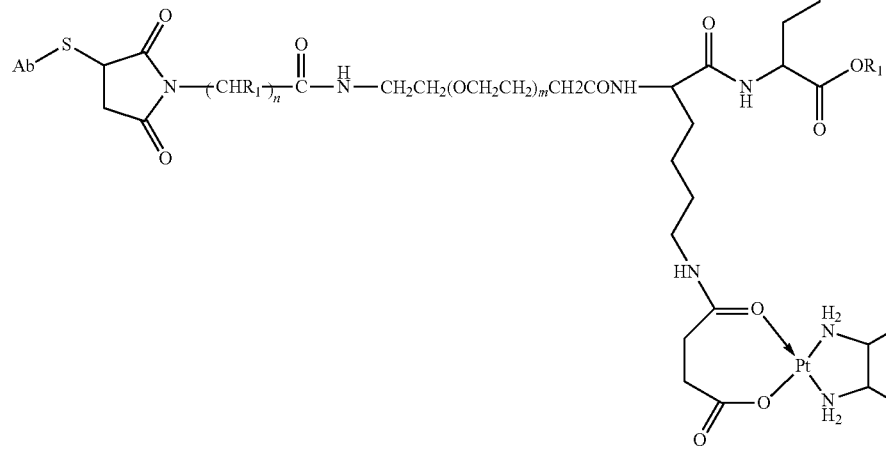

$R_1$ = H, alkyl, aryl group
$n$ = 1-3
$m$ = 2-100
Ab = Antibody

In another embodiment, taking advantage of the significant advances made in antibody engineering and other conjugation technologies, and synthesizing new platinum-analogs with improved toxicity and release kinetics (*PNAS* 2010; 107:12435-12440), it is an object of the present invention to generate ligand-targeted conjugates of Pt (II) analogs, such as antibody-drug conjugates which are chemically linkable to monoclonal antibodies or other targeting ligands, in such a way that the desired cytotoxicity and in vivo stability is obtained.

In another embodiment, the linker-drug conjugate is complexed to the ligand through a thioether or other covalent linkage. In another embodiment of the present disclosure, the lysine-Pt (II) complex is capable of attaching 1-3 Pt (II) analogs, resulting in 3-12-fold increase in drug loading per targeting ligand. The Pt is additionally complexed with a diaminocyclohexane or diamine moieties, i.e., activated forms of oxaliplatin or carboplatin and cisplatin post-aquation.

The present invention further provides the ligand drug conjugates (LDCs) shown in FIG. 2. As shown in FIG. 2, these LDCs comprise at least two linkers attached to the ligand, each linker being further bonded to a drug or cytotoxic agent.

Figure 5:
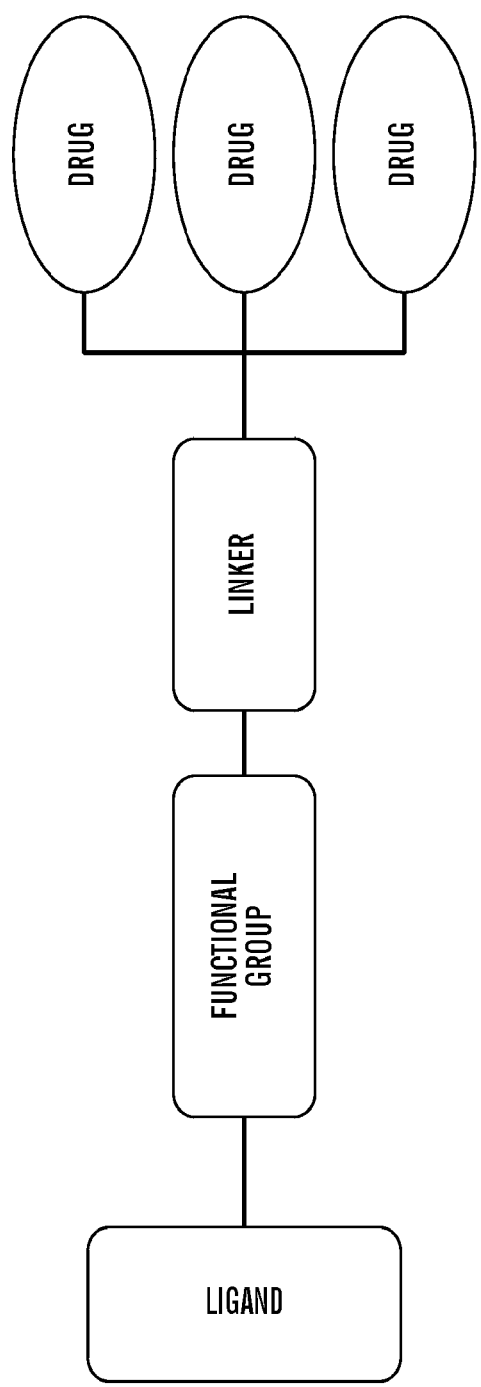
FIG. 5 is a schematic representation of Ligand-Drug Conjugate (LDC) comprising a linker coupled with multiple cytotoxic drugs.

In some embodiments, a LDC of FIG. 2 is a cisplatin/oxaliplatin based antibody-drug conjugate (ADC) as shown The present invention also provides ligand drug conjugates (LDCs) as shown in FIG. 5. These LDCs comprise at least two drugs or cytotoxins attached to the linker.

Figure 6:
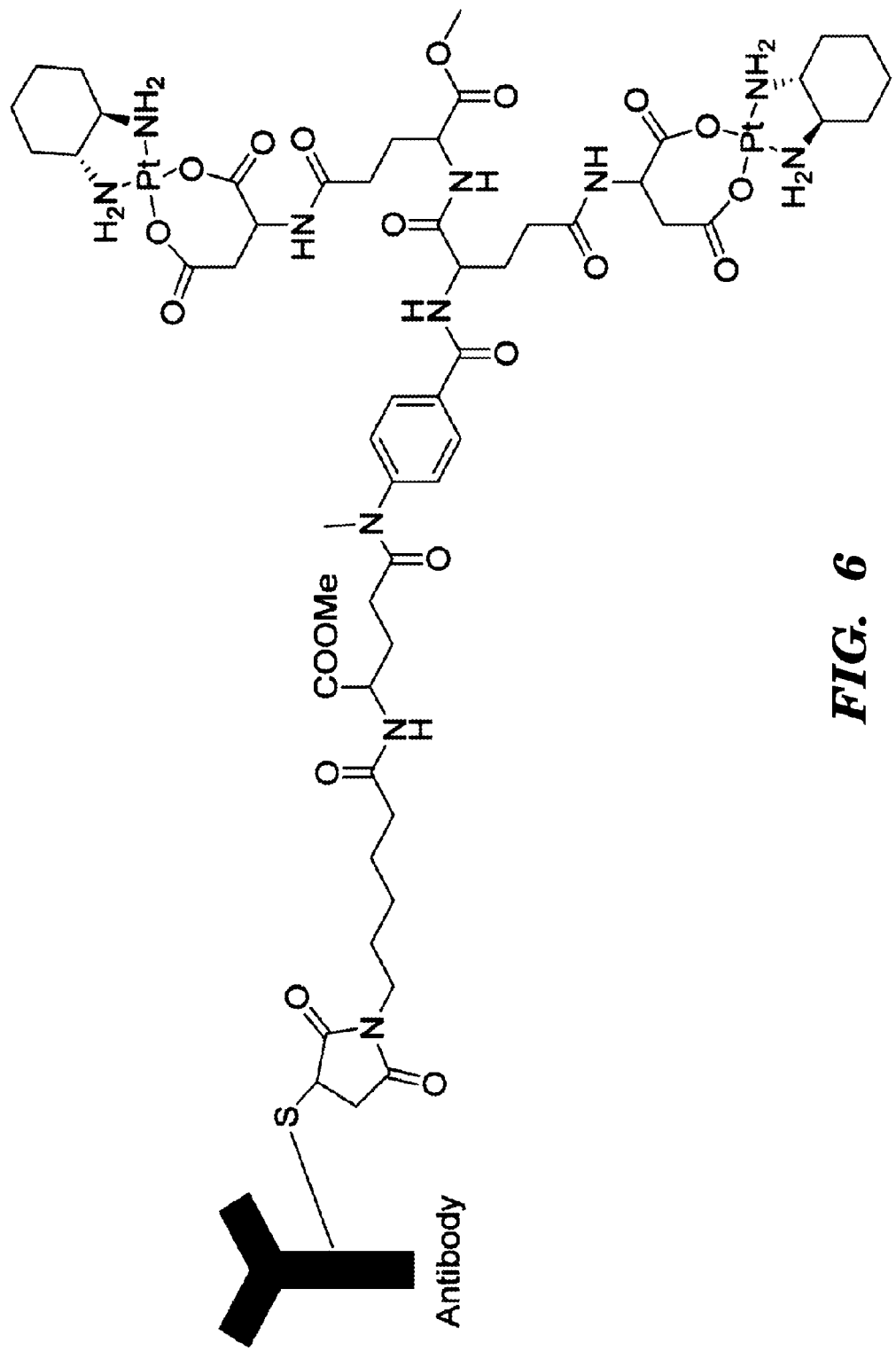
FIG. 6 shows a general structure of a oxaliplatin based LDC where linker is conjugated to multiple platinum drugs.
Figure 7:
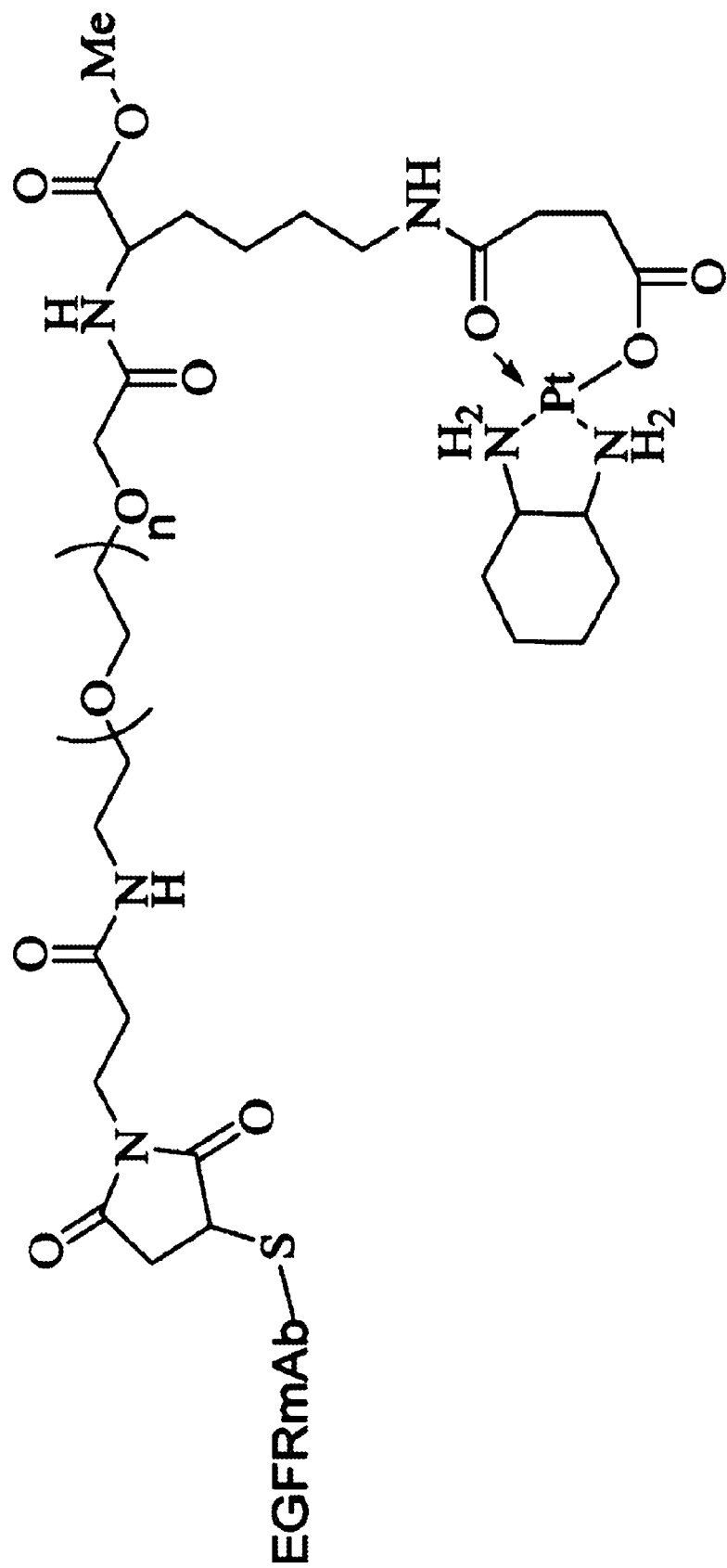
FIG. 7 shows the structure of an epithelial growth factor receptor (EGFR)-targeted monoclonal antibody Oxaliplatin-linked monolysinated linker based ADC.
Figure 8:
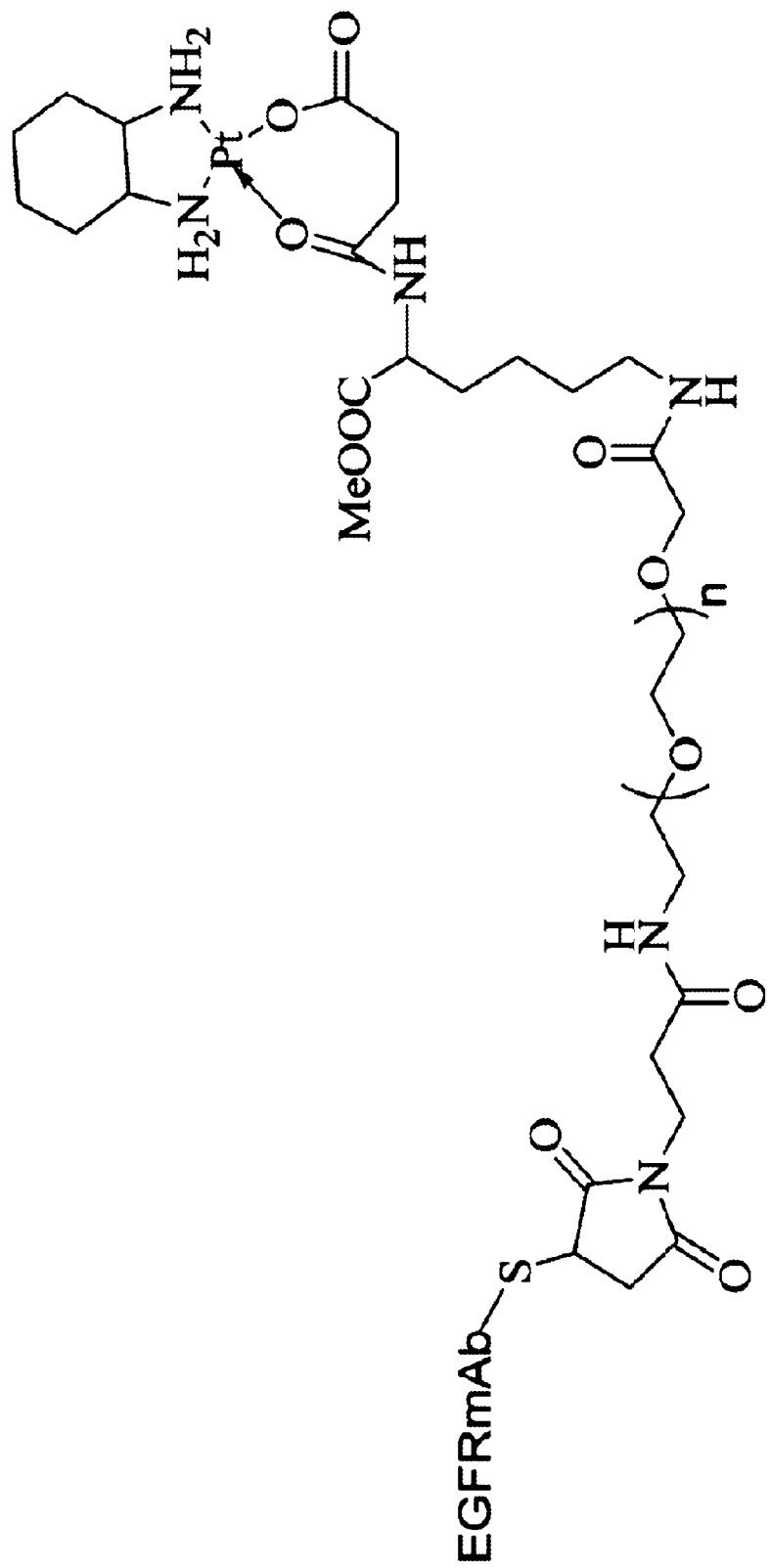
FIG. 8 shows the structure of an EGFR-targeted monoclonal antibody Oxaliplatin linked monolysinated linker based ADC. The succinate Pt(II) complex linked via the α-NH$_2$ group of lysine.
Figure 9:
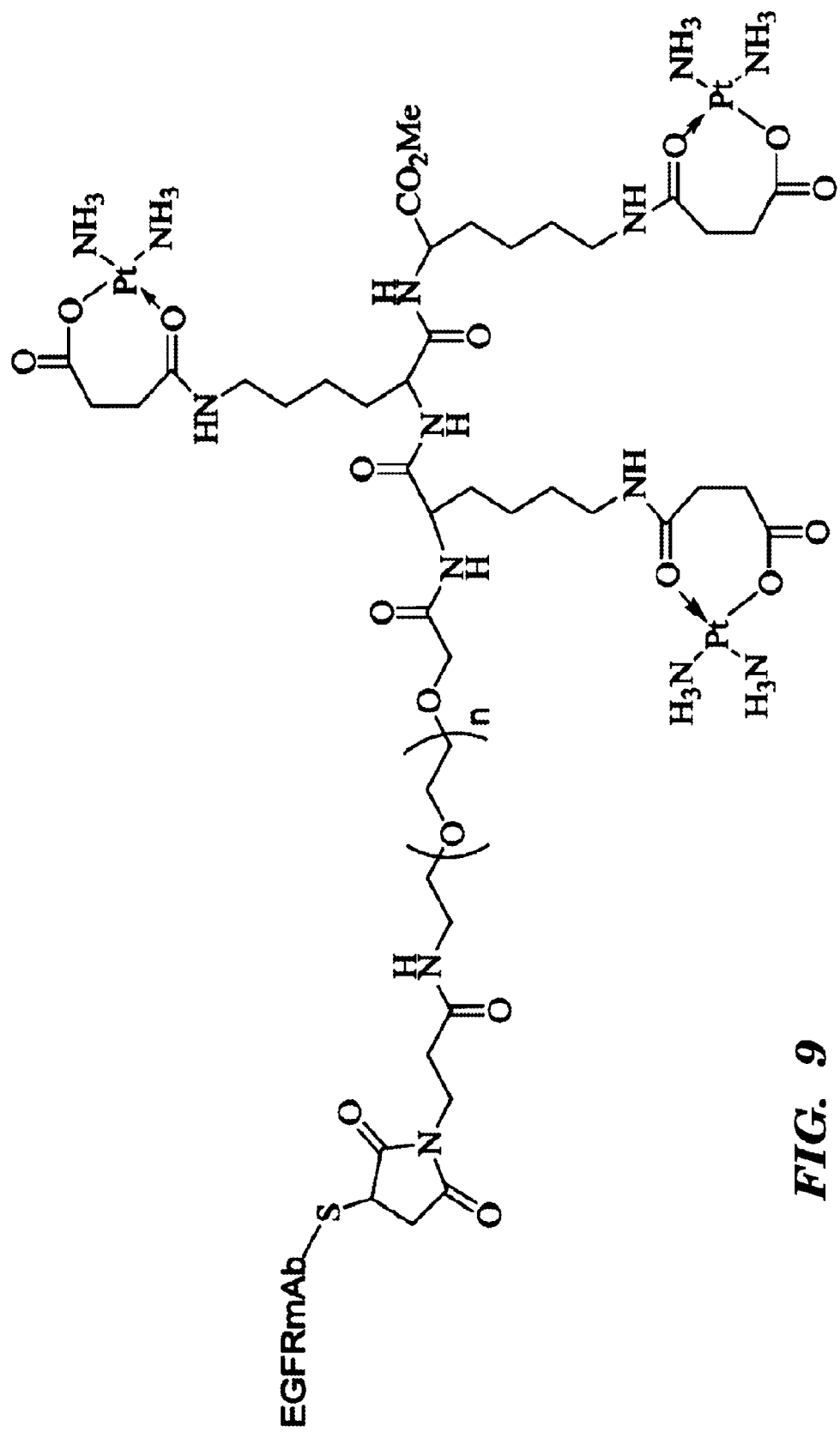
FIG. 9 shows the structure of an EGFR-targeted monoclonal antibody Oxaliplatin linked tri-lysinated linker based antibody-drug conjugate (ADC).

Exemplary LDCs of FIG. 5 are shown in FIGS. 6 and 9. FIG. 6 depicts a general structure of oxaliplatin based LDC where linker is conjugated to a non-polar spacer and multiple Pt(II) drugs. FIG. 7 shows a specific structure of a Epithelial Growth Factor Receptor (EGFR)-targeted monoclonal antibody Oxaliplatin-linked monolysinated linker based ADC. The succinate Pt(II) complex linked to the linker via the ε-$NH_2$ group of lysine; n=2-100. FIG. 8 shows a specific structure of a Epithelial Growth Factor Receptor (EGFR)-targeted monoclonal antibody Oxaliplatin linked monolysinated linker based ADC. The succinate Pt(II) complex linked to the linker via the α-$NH_2$ group of lysine; n=2-100. FIG. 9 shows a specific structure of a Epithelial Growth Factor Receptor (EGFR)-targeted monoclonal antibody Oxaliplatin linked tri-lysinated linker based antibody-drug conjugate (ADC). The succinate Pt(II) complex linked to the linker via the ε-$NH_2$ group of lysine; n=2-100.

The present invention also provides ligand-drug conjugates (LDCs) where the Pt (II) is part of the linker and the cytotoxic drug is conjugated to the co-ordination metal complex. The platinum metal acts as the leaving group to release the drug at the site of action. The following structures depict some examples of ligand-drug conjugates of FIGS. 1A and 1B as discussed in foregoing section.

Figure 10:
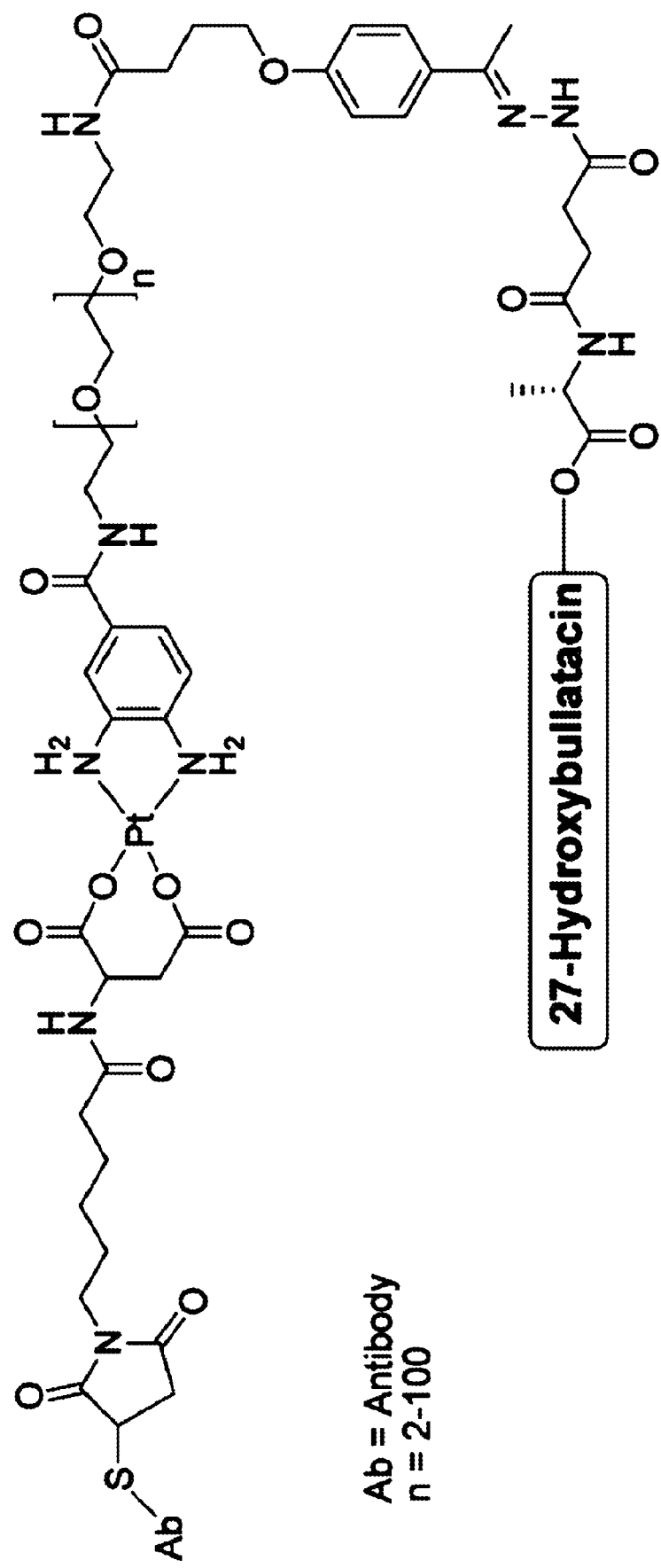
FIG. 10 shows the structure of an antibody-targeted Pt(II) coordination complex conjugated to the cytotoxic drug 27-hydroxybullatacin via an ester-linkage.
Figure 11:
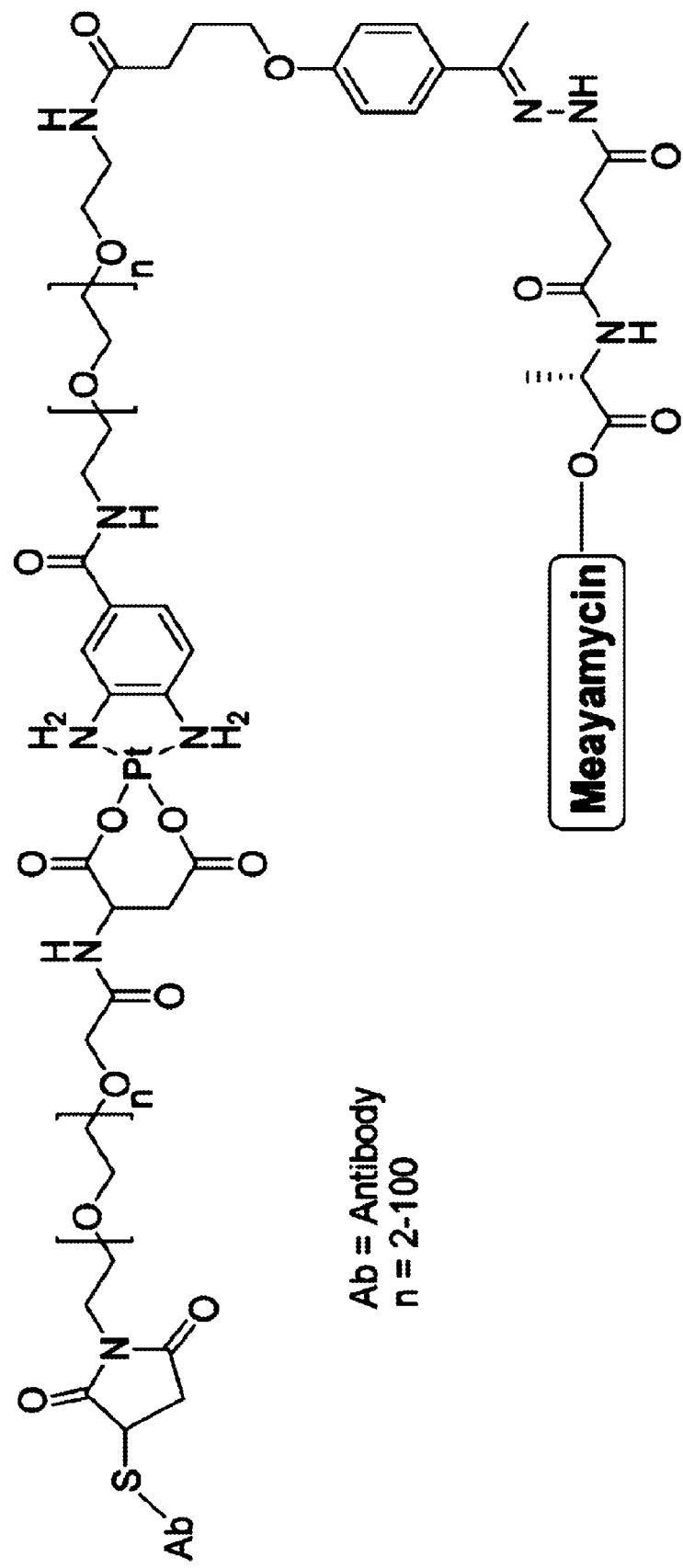
FIG. 11 shows the structure of an antibody-targeted Pt(II) coordination complex conjugated to the cytotoxic drug meayamycin via an ester-linkage.

Accordingly, in some embodiments, the ligand drug conjugate of formula A-B-C-B'-D is selected from the compounds shown in FIGS. 10 and 11. FIG. 10 shows structure of an antibody-targeted Pt(II) coordination complex conjugated to the cytotoxic drug 27-hydroxybullatacin via an ester-linkage. The Pt(II) linker complex is flanked on one side by a non-polar and other side by a PEG spacer. FIG. 11 shows structure of an antibody-targeted Pt(II) coordination complex conjugated to the cytotoxic drug meayamycin via an ester-linkage. The Pt(II) linker complex is flanked on both sides by a PEG spacer.

Yet another aspect of the invention is directed to a method of treating cancer or metastasis. The method includes administering to a subject in need thereof an effective amount of any of the conjugates, compounds, or compositions described herein.

For administration to a subject, the conjugates described herein can be provided in pharmaceutically acceptable compositions. These pharmaceutically acceptable compositions comprise a therapeutically-effective amount of one or more of the conjugates described herein, formulated together with one or more pharmaceutically acceptable carriers (additives) and/or diluents. As described in detail below, the pharmaceutical compositions of the present invention can be specially formulated for administration in solid or liquid form, including those adapted for the following: (1) oral administration, for example, drenches (aqueous or non-aqueous solutions or suspensions), lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; or (9) nasally. Additionally, compounds can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and 35 3,270, 960.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment. For example, an amount of a compound administered to a subject that is sufficient to produce a statistically significant, measurable change in at least one symptom of cancer or metastasis.

Determination of a therapeutically effective amount is well within the capability of those skilled in the art. Generally, a therapeutically effective amount can vary with the subject's history, age, condition, sex, as well as the severity and type of the medical condition in the subject, and administration of other pharmaceutically active agents.

As used herein, the term "administer" refers to the placement of a composition into a subject by a method or route which results in at least partial localization of the composition at a desired site such that desired effect is produced. A compound or composition described herein can be administered by any appropriate route known in the art including, but not limited to, oral or parenteral routes, including intravenous, intramuscular, subcutaneous, transdermal, airway (aerosol), pulmonary, nasal, rectal, and topical (including buccal and sublingual) administration.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In preferred embodiments, the compositions are administered by intravenous infusion or injection.

By "treatment", "prevention" or "amelioration" of a disease or disorder is meant delaying or preventing the onset of such a disease or disorder, reversing, alleviating, ameliorating, inhibiting, slowing down or stopping the progression, aggravation or deterioration the progression or severity of a condition associated with such a disease or disorder. In one embodiment, at least one symptom of a disease or disorder is alleviated by at least 5%, at least 10%, at least 20%, at least 30%, at least 40%, or at least 50%.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments, the subject is a mammal, e.g., a primate, e.g., a human. The terms, "patient" and "subject" are used interchangeably herein. The terms, "patient" and "subject" are used interchangeably herein.

Preferably, the subject is a mammal. The mammal can be a human, non-human primate, mouse, rat, dog, cat, horse, or cow, but are not limited to these examples. Mammals other than humans can be advantageously used as subjects that represent animal models of disorders associated with inflammation.

In addition, the methods described herein can be used to treat domesticated animals and/or pets. A subject can be male or female. A subject can be one who has been previously diagnosed with or identified as suffering from or having a disorder a cancer or metastasis, but need not have already undergone treatment.

The conjugates of the invention are also useful in combination with known anti-cancer treatments, including radiation. The methods of the invention are especially useful in combination with anti-cancer treatments that involve administering a second drug that acts in a different phase of the cell cycle.

Some Selected Definitions

For convenience, certain terms employed herein, in the specification, examples and appended claims are collected herein. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

Other than in the operating examples, or where otherwise indicated, all numbers expressing quantities of ingredients or reaction conditions used herein should be understood as modified in all instances by the term "about." The term "about" when used to described the present invention, in connection with percentages means±1%, ±1.5%, ±2%, ±2.5%, ±3%, ±3.5%, ±4%, ±4.5%, or ±5%. The term "about" when used in connection with percentages may mean±1%, ±1.5%, ±2%, ±2.5%, ±3%, ±3.5%, ±4%, ±4.5%, or ±5% of the value being referred to.

The singular terms "a," "an," and "the" include plural referents unless context clearly indicates otherwise. Similarly, the word "or" is intended to include "and" unless the context clearly indicates otherwise.

As used herein the terms "comprising" or "comprises" means "including" or "includes" and are used in reference to compositions, methods, systems, and respective component(s) thereof, that are useful to the invention, yet open to the inclusion of unspecified elements, whether useful or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, systems, and respective components thereof as described herein, which are exclusive of any element not recited in that description of the embodiment.

The abbreviation, "e.g." is derived from the Latin exempli gratia, and is used herein to indicate a non-limiting example. Thus, the abbreviation "e.g." is synonymous with the term "for example."

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means at least two standard deviation (2SD) away from a reference level. The term refers to statistical evidence that there is a difference. It is defined as the probability of making a decision to reject the null hypothesis when the null hypothesis is actually true.

The term "derivative" as used herein refers to a chemical substance related structurally to another, i.e., an "original" substance, which can be referred to as a "parent" compound. A "derivative" can be made from the structurally-related parent compound in one or more steps. In some embodiments, the general physical and chemical properties of a derivative can be similar to or different from the parent compound.

The term "alkyl" refers to saturated non-aromatic hydrocarbon chains that may be a straight chain or branched chain, containing the indicated number of carbon atoms (these include without limitation methyl, ethyl, propyl, iso-propyl, butyl, 2-methyl-ethyl, t-butyl, allyl, or propargyl), which may be optionally inserted with N, O, or S. For example, $C_1$-$C_6$ indicates that the group may have from 1 to 6 (inclusive) carbon atoms in it.

The term "alkenyl" refers to an alkyl that comprises at least one double bond. Exemplary alkenyl groups include, but are not limited to, for example, ethenyl, propenyl, butenyl, 1-methyl-2-buten-1-yl and the like.

The term "alkynyl" refers to an alkyl that comprises at least one triple bond.

The term "aryl" refers to monocyclic, bicyclic, or tricyclic aromatic ring system wherein 0, 1, 2, 3, or 4 atoms of each ring may be substituted by a substituent. Exemplary aryl groups include, but are not limited to, benzyl, phenyl, naphthyl, anthracenyl, azulenyl, fluorenyl, indanyl, indenyl, naphthyl, phenyl, tetrahydronaphthyl, and the like.

The term "cyclyl" or "cycloalkyl" refers to saturated and partially unsaturated cyclic hydrocarbon groups having 3 to 12 carbons, for example, 3 to 8 carbons, and, for example, 3 to 6 carbons, wherein the cycloalkyl group additionally may be optionally substituted. Exemplary cycloalkyl groups include, but are not limited to, cyclopropyl, cyclobutyl, cyclopentyl, cyclopentenyl, cyclohexyl, cyclohexenyl, cycloheptyl, cyclooctyl, and the like.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent. Exemplary heteroaryl groups include, but are not limited to, pyridyl, furyl or furanyl, imidazolyl, benzimidazolyl, pyrimidinyl, thiophenyl or thienyl, pyridazinyl, pyrazinyl, quinolinyl, indolyl, thiazolyl, naphthyridinyl, and the like.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Exemplary heterocyclyl groups include, but are not limited to piperazinyl, pyrrolidinyl, dioxanyl, morpholinyl, tetrahydrofuranyl, and the like.

The term "optionally substituted" means that the specified group or moiety, such as an alkyl group, alkenyl group, and the like, is unsubstituted or is substituted with one or more (typically 1-4 substituents) independently selected from the group of substituents listed below in the definition for "substituents" or otherwise specified.

The term "substituents" refers to a group "substituted" on the substituted entity (e.g., an alkyl, alkenyl, alkynyl, cycloalkyl, aryl, heterocyclyl, or heteroaryl group) at any atom of that entity. Suitable substituents include, without limitation, halogen, hydroxy, oxo, nitro, haloalkyl, alkyl, alkenyl, alkynyl, alkaryl, aryl, aralkyl, alkoxy, aryloxy, amino, acylamino, alkylcarbanoyl, arylcarbanoyl, aminoalkyl, alkoxycarbonyl, carboxy, hydroxyalkyl, alkanesulfonyl, arenesulfonyl, alkanesulfonamido, arenesulfonamido, aralkylsulfonamido, alkylcarbonyl, acyloxy, cyano or ureido. In some cases, two substituents, together with the carbons to which they are attached to can form a ring.

In some embodiments, the substituent group is selected from alkyl, ester, amide, monocarbonyl, dicarbonyl, ketones, aldehydes, and the like.

As used herein, the term "epitope" means that portion of protein that is recognized by a particular antibody. As such, the term "epitope" designates a specific amino acid sequence, modified amino acid sequence, or protein secondary or tertiary structure which is recognized by an antibody.

As used herein, the term "anti-cancer activity" or "anticancer properties" refers to the inhibition (in part or in whole) or prevention of unregulated cell growth and/or the inhibition (in part or in whole) or prevention of a cancer as defined herein. Anticancer activity includes, e.g., the ability to reduce, prevent, or repair genetic damage, modulate undesired cell proliferation, modulate misregulated cell death, or modulate mechanisms of metastasis (e.g., ability to migrate).

As used herein, the term "cancer" refers to an uncontrolled growth of cells that may interfere with the normal functioning of the bodily organs and systems. Cancers that migrate from their original location and seed vital organs can eventually lead to the death of the subject through the functional deterioration of the affected organs. A metastasis a cancer cell or group of cancer cells, distinct from the primary tumor location resulting from the dissemination of cancer cells from the primary tumor to other parts of the body. At the time of diagnosis of the primary tumor mass, the subject may be monitored for the presence of in transit metastases, e.g., cancer cells in the process of dissemination. As used herein, the term cancer, includes, but is not limited to the following types of cancer, breast cancer, biliary tract cancer, bladder cancer, brain cancer including Glioblastomas and medulloblastomas; cervical cancer; choriocarcinoma; colon cancer; endometrial cancer; esophageal cancer, gastric cancer; hematological neoplasms including acute lymphocytic and myelogenous leukemia; T-cell acute lymphoblastic leukemia/lymphoma; hairy cell leukemia; chronic myelogenous leukemia, multiple myeloma; AIDS-associated leukemias and adult T-cell leukemia lymphoma; intraepithelial neoplasms including Bowen's disease and Paget's disease; liver cancer; lung cancer; lymphomas including Hodgkin's disease and lymphocytic lymphomas; neuroblastomas; oral cancer including squamous cell carcinoma; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, and osteosarcoma; skin cancer including melanoma, Merkel cell carcinoma, Kaposi's sarcoma, basal cell carcinoma, and squamous cell cancer; testicular cancer including germinal tumors such as seminoma, non-seminoma (teratomas, choriocarcinomas), stromal tumors, and germ cell tumors; thyroid cancer including thyroid adenocarcinoma and medullar carcinoma; and renal cancer including adenocarcinoma, Wilms tumor. Examples of cancer include but are not limited to, carcinoma, including adenocarcinoma, lymphoma, blastoma, melanoma, sarcoma, and leukemia. More particular examples of such cancers include squamous cell cancer, small-cell lung cancer, non-small cell lung cancer, gastrointestinal cancer, Hodgkin's and non-Hodgkin's lymphoma, pancreatic cancer, Glioblastoma, cervical cancer, ovarian cancer, liver cancer such as hepatic carcinoma and hepatoma, bladder cancer, breast cancer, colon cancer, colorectal cancer, endometrial carcinoma, salivary gland carcinoma, kidney cancer such as renal cell carcinoma and Wilms' tumors, basal cell carcinoma, melanoma, prostate cancer, vulval cancer, thyroid cancer, testicular cancer, esophageal cancer, and various types of head and neck cancer. Other cancers will be known to the artisan.

As used herein, the term "cancer" includes, but is not limited to, solid tumors and blood born tumors. The term cancer refers to disease of skin, tissues, organs, bone, cartilage, blood and vessels. The term "cancer" further encompasses primary and metastatic cancers. Examples of cancers that can be treated with the compounds of the invention include, but are not limited to, carcinoma, including that of the bladder, breast, colon, kidney, lung, ovary, pancreas, stomach, cervix, thyroid, and skin, including squamous cell carcinoma; hematopoietic tumors of lymphoid lineage, including, but not limited to, leukemia, acute lymphocytic leukemia, acute lymphoblastic leukemia, B-cell lymphoma, T-cell lymphoma, Hodgkins lymphoma, non-Hodgkins lymphoma, hairy cell lymphoma, and Burketts lymphoma; hematopoietic tumors of myeloid lineage including, but not limited to, acute and chronic myelogenous leukemias and promyelocytic leukemia; tumors of mesenchymal origin including, but not limited to, fibrosarcoma, rhabdomyosarcoma, and osteosarcoma; other tumors including melanoma, seminoma, tetratocarcinoma, neuroblastoma, and glioma; tumors of the central and peripheral nervous system including, but not limited to, astrocytoma, neuroblastoma, glioma, and schwannomas; and other tumors including, but not limited to, xenoderma, pigmentosum, keratoactanthoma, thyroid follicular cancer, and teratocarcinoma. The compounds of the invention are useful for treating patients who have been previously treated for cancer, as well as those who have not previously been treated for cancer. Indeed, the methods and compositions of this invention can be used in first-line and second-line cancer treatments.

In some embodiments, the cancer or metastasis is selected from the group consisting of platinum susceptible or resistant tumors including breast, head and neck, ovarian, testicular, pancreatic, oral-esophageal, gastrointestinal, liver, gall bladder, lung, melanoma, skin cancer, sarcomas, blood cancers, brain tumors including glioblastomas, and tumors of neuroectodermal origin.

As used herein, the term "precancerous condition" has its ordinary meaning, i.e., an unregulated growth without metastasis, and includes various forms of hyperplasia and benign hypertrophy. Accordingly, a "precancerous condition" is a disease, syndrome, or finding that, if left untreated, can lead to cancer. It is a generalized state associated with a significantly increased risk of cancer. Premalignant lesion is a morphologically altered tissue in which cancer is more likely to occur than its apparently normal counterpart. Examples of pre-malignant conditions include, but are not limited to, oral leukoplakia, actinic keratosis (solar keratosis), Barrett's esophagus, atrophic gastritis, benign hyperplasia of the prostate, precancerous polyps of the colon or rectum, gastric epithelial dysplasia, adenomatous dysplasia, hereditary nonpolyposis colon cancer syndrome (HNPCC), Barrett's esophagus, bladder dysplasia, precancerous cervical conditions, and cervical dysplasia.

As used herein, amino acids include natural or unnatural amino acids. Thus, as used herein, the term "amino acid" includes compounds which depart from the structure of the naturally occurring amino acids, but which have substantially the structure of an amino acid, such that they can be substituted within a peptide which retains is activity, e.g., biological activity. Thus, for example, in some embodiments amino acids can also include amino acids having side chain modifications or substitutions, and also include related organic acids, amides or the like. Without limitation, an amino acid can be a proteogenic or non-proteogenic amino acid. As used herein, the term "proteogenic" indicates that the amino acid can be incorporated into a protein in a cell through well-known metabolic pathways. Exemplary amino acids amenable to the present invention include, but are not limited to, alanine; argnine; asparagine; aspartic acid; cysteine; glutamic acid; glutamine; glycine; histadine; isoleucine; leucine; lysine; methionine; phenylalanine; proline; serine; threonine; tryptophan; tyrosine; valine; homocysteine; phosphoserine; phosphothreonine; phosphotyrosine; hydroxyproline; γ-carboxyglutamate; hippuric acid; octahydroindole-2-carboxylic acid; statine; 1,2,3,4,-tetrahydroisoquinoline-3-carboxylic acid; penicillamine (3-mercapto-D-valine); ornithine (Orn); citruline; alpha-methyl-alanine; para-benzoylphenylalanine; para-aminophenylalanine; p-fluorophenylalanine; phenylglycine; propargylglycine; N-methylglycins (sarcosine, Sar); and tert-butylglycine; diaminobutyric acid; 7-hydroxy-tetrahydroisoquinoline carboxylic acid; naphthylalanine; biphenylalanine; cyclohexylalanine; amino-isobutyric acid (Aib); norvaline; norleucine (Nle); tert-leucine; tetrahydroisoquinoline carboxylic acid; pipecolic acid; phenylglycine; homophenylalanine; cyclohexylglycine; dehydroleucine; 2,2-diethylglycine; 1-amino-1-cyclopentanecarboxylic acid; 1-amino-1-cyclohexanecarboxylic acid; amino-benzoic acid; amino-naphthoic acid; gamma-aminobutyric acid; difluorophenylalanine; nipecotic acid; N-α-imidazole acetic acid (IMA); thienyl-alanine; t-butylglycine; desamino-Tyr; aminovaleric acid (Ava); pyroglutaminic acid (<Glu); α-aminoisobutyric acid (aAib); γ-aminobutyric acid (yAbu); α-aminobutyric acid (aAbu); αγ-aminobutyric acid (αγAbu); 3-pyridylalanine (Pal); Isopropyl-α-$N^\epsilon$-lysine (ILys); Napthyalanine (Nal); α-napthyalanine (α-Nal); β-napthyalanine (β-Nal); Acetyl-β-napthyalanine (Ac-β-Napthyalanine); napthyalanine; $N^\epsilon$-picoloyl-lysine (PicLys); 4-halo-Phenyl; 4-pyrolidylalanine; isonipecotic carboxylic acid (inip); beta-amino acids; and isomers, analogs and derivatives thereof. One of skill in the art would know that this definition includes, D- and L-amino acids, alpha- and beta-amino acids, chemically modified amino acids, naturally occurring non-proteogenic amino acids, rare amino acids, and chemically synthesized compounds that have properties known in the art to be characteristic of an amino acid.

Peptide modifications are well known in the art. Thus, a peptide described herein, e.g., a linker peptide, can comprise one or more peptide modifications known in the art. Exemplary peptide modifications for modifying the fusion protein described herein include, but are not limited to, D amino acids, α amino acids, β amino acids, non-amide or modified amide linkages, chemically modified amino acids, naturally occurring non-proteogenic amino acids, rare amino acids, chemically synthesized compounds that have properties known in the art to be characteristic of an amino acid, and the like. Thus, as used herein, peptide includes natural or unnatural amino acids, or a combination thereof.

As used herein, the term "PEG" means an ethylene glycol polymer that contains about 20 to about 2000000 linked monomers, typically about 50-1000 linked monomers, usually about 100-300. Polyethylene glycols include PEGs containing various numbers of linked monomers, e.g., PEG20, PEG30, PEG40, PEG60, PEG80, PEG100, PEG115, PEG200, PEG 300, PEG400, PEG500, PEG600, PEG1000, PEG1500, PEG2000, PEG3350, PEG4000, PEG4600, PEG5000, PEG6000, PEG8000, PEG11000, PEG12000, PEG2000000 and any mixtures thereof.

Embodiments of the various aspects described herein can also be described by any one of the following paragraphs.

1. A ligand-targeted molecule comprising:
   (i) a functional moiety;
   (ii) a linker connected to said functional moiety;
   (iii) a dicarbonyl moiety connected to said linker; and
   (iv) a drug connected to said dicarbonyl moiety;
   wherein said drug is a platinum chemotherapeutic agent.
2. The ligand-targeted molecule of paragraph 1 wherein said platinum chemotherapeutic agent are Pt(II) chemotherapeutic agents.
3. The ligand-targeted molecule of any of paragraphs 1-2, wherein said platinum chemotherapeutic agent is cisplatin, oxaliplatin, carboplatin or other Pt(II) agents.
4. The ligand-targeted molecule of any of paragraphs 1-3, wherein said functional moiety is thiol reactive, amine reactive or azide reactive.
5. The ligand-targeted molecule of any of paragraphs 1-4, wherein said functional moiety is maleimide.
6. The ligand-targeted molecule of any of paragraphs 1-5, wherein said linker is a hydrocarbon, polyethylene glycol (PEG), an amino acid, a peptide, or a combination thereof, said hydrocarbon or PEG being substituted or unsubstituted.
7. The ligand-targeted molecule of paragraph 6, wherein said linker is a hydrocarbon.
8. The ligand-targeted molecule of paragraph 6, wherein said linker is PEG.
9. The ligand-targeted molecule of paragraph 8, wherein said PEG has a molecular weight of between from about 200 Da to about 50 kDa.
10. The ligand-targeted molecule of any of paragraphs 1-9, wherein said linker comprises a combination of at least one amino acid and substituted or unsubstituted PEG.
11. The ligand-targeted molecule of paragraph 10 wherein said amino acid is lysine.
12. The ligand-targeted molecule of any of paragraphs 1-11, wherein said linker comprises a combination of two amino acids and substituted or unsubstituted PEG.
13. The ligand-targeted molecule of any of paragraphs 1-11, wherein said linker comprises a combination of three amino acids and substituted or unsubstituted PEG.
14. The ligand-targeted molecule of any of paragraphs 1-13, wherein said dicarboxyl moiety is succinate
15. The ligand-targeted molecule of paragraph 14 wherein said dicarbonyl moiety is succinate.
16. A ligand drug conjugate comprising a ligand connected to a ligand-targeted molecule, wherein said ligand-targeted molecule comprises a functional moiety, at least one linker connected to said functional moiety, a dicarbonyl moiety connected to said linker, and a drug connected to said dicarbonyl moiety, said drug being a platinum chemotherapeutic agent, and said ligand being connected to said functional moiety.
17. The ligand drug conjugate of paragraph 16 wherein said ligand is an antibody, antibody fragment, peptide, agonist, antagonist or aptamer.
18. The ligand drug conjugate of any of paragraphs 16-17, wherein said ligand is an antibody.
19. The ligand drug conjugate of paragraph 18 wherein said antibody is targeted to the Epidermal Growth Factor Receptor.
20. The ligand drug conjugate of paragraph 19 wherein said antibody is connected to said functional moiety through a thioether bond.
21. A ligand drug conjugate comprising a ligand connected to a ligand-targeted molecule, wherein said ligand-targeted molecule comprises a functional moiety, at least one linker connected to said functional moiety, a first drug connected to said linker, a dicarbonyl moiety connected to said linker, and a second drug connected to said dicarbonyl moiety, said second drug being a platinum compound, and said ligand being connected to said functional moiety.
22. The conjugate of paragraph 21, wherein said first drug is an anti-cancer agent.
23. The conjugate of paragraph 22, wherein said anti-cancer agent is selected from the group consisting of Maytansinoid (DM1 and DM4); CC-1065; Adozelesin (DC1); DC4; Calicheamicins; Dolastatins; Auristatins E and F; Meamycin; Doxorubucin; Paclitaxel; Docetaxel; Laulimalide; Epothilones A and B; Discodermolide; Eleutherobin; Peloruside A; cyclophosphamide, chlorambucil, uramustine, ifosfamide, melphalan, and bendamustine; Carmustine, lomustine, semustine; Busulfan; Thiotepa; Dacarbazine; Methotrexate; 6-mercaptopurine, 6-thioguanine, pentostatin, fludarabine; 5-fluorouracil, cytarabine, leukovorin; Dactinomycin; Bleomycin; Daunorubicin; Mitomycin; Idarubicin; Plicamycin; Vincristine; Vinblastine; Vinorelbine; Etoposide; Teniposide; Asparaginase; Maitotoxin; Irinotecan (CPT-11); Fumagillin; Fumagalone; Fumarranol; O-(Chloroacetylcarbamoyl)-Fumagillol (AGM-1470, TNP-470); 27-hydroxybullatacin, derivatives and analogues thereof, and any combinations thereof.
24. The conjugate of any of paragraphs 21-23, wherein said platinum compound is a platinum (II) compound.
25. The conjugate of paragraph 24, wherein said platinum (II) compound is selected from the group consisting of cisplatin, oxaliplatin, carboplatin, paraplatin, sartraplatin, and combinations thereof.
26. The conjugate of any of paragraphs 21-25, wherein said ligand binds a protein, receptor, or cell marker on a surface of a cancer cell.
27. The conjugate of any of paragraphs 21-26, wherein said ligand binds Epidermal Growth Factor Receptor.
28. The conjugate of any of paragraphs 21-27, wherein said ligand is an antibody, antibody fragment, peptide, agonist, antagonist or aptamer.
29. The conjugate of paragraph 28, wherein said antibody is selected from the group consisting of C242 antibody (CanAg), Rituximab, Trastuzumab (Her2), Cetuximab, Bevacizumab (VEGF), Panitumumab, Alemtuzumab, Ofatumumab, Gemtuzumab (CD33), Inotuzumab (CD22), Lorvotuzumab (CD56), Brentuximab (CD30), Glembatumumab (GPNMB), epitope bind fragments thereof and any combinations thereof.
30. The conjugate of any of paragraphs 21-29, wherein said linker is a hydrocarbon, polyethylene glycol (PEG), an amino acid, a peptide, or a combination thereof, said hydrocarbon or PEG being substituted or unsubstituted.
31. The conjugate of paragraph 30, wherein said linker is a hydrocarbon.
32. The conjugate of paragraph 30, wherein said linker is PEG.
33. The conjugate of paragraph 32, wherein said PEG has a molecular weight of between from about 200 Da to about 50 kDa.
34. The conjugate of any of paragraphs 21-33, wherein said linker comprises a combination of at least one amino acid and substituted or unsubstituted PEG.
35. The conjugate of paragraph 34, wherein said linker comprises two or three amino acids.

36. The conjugate of paragraph 34, wherein said amino acid is lysine.
37. The conjugate of any of paragraphs 21-36, wherein said dicarbonyl moiety is succinate
38. The conjugate of paragraph 37, wherein said dicarbonyl moiety is succinate.
39. A ligand drug conjugate comprising a ligand connected to a ligand-targeted molecule, wherein said ligand-targeted molecule comprises a functional moiety, at least one first linker connected to said functional moiety, a coordination metal complex connected to said first linker, at least one second linker connected to said coordination metal complex, a drug connected to said second linker, and said ligand connected to said functional moiety.
40. The conjugate of paragraph 39, wherein said coordination metal complex comprises a O->metal coordination bond.
41. The conjugate of any of paragraphs 39-40, wherein said O->metal coordination bond is with amide carbonyl oxygen or ester carbonyl oxygen.
42. The conjugate of any of paragraphs 39-41, wherein said coordination metal complex is a platinum, iron, or silicon complex.
43. The conjugate of any of paragraphs 39-42, wherein said coordination metal complex is a platinum (II) complex.
44. The conjugate of paragraph 43, wherein said platinum (II) complex is

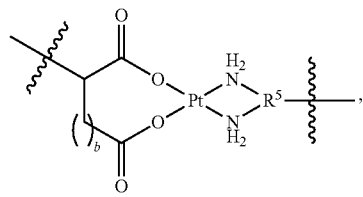

wherein b is 0, 1, 2, 3, 4, or 5 and $R^5$ is a cyclic or acyclic linker joining the two amino groups to the first or the second linker;

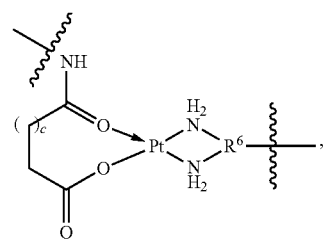

wherein c is 0, 1, 2, 3, 4, or 5 and $R^6$ is a cyclic or acyclic linker joining the two amino groups to first or the second linker;

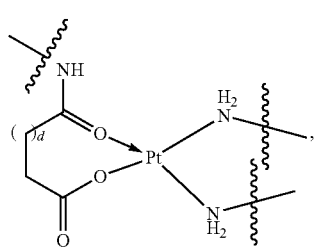

wherein d is 0, 1, 2, 3, 4, or 5 and the two amines are linked to different first or second linkers;

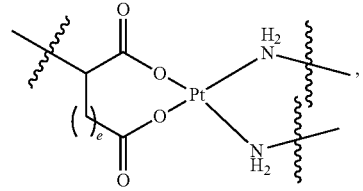

wherein e is 0, 1, 2, 3, 4, or 5, and the two amines are linked to different first or second linkers;

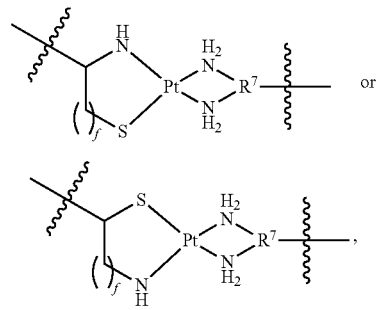

wherein f is 0, 1, 2, 3, 4, or 5 and $R^7$ is a cyclic or acyclic linker joining the two amino groups to the first or the second linker;

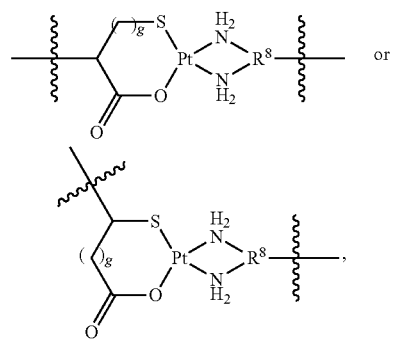

wherein g is 0, 1, 2, 3, 4, or 5 and $R^8$ is a cyclic or acyclic linker joining the two amino groups to the first or the second linker; or

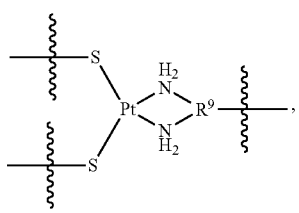

wherein $R^9$ is a cyclic or acyclic linker joining the two amino groups to the first or the second linker.

45. The conjugate of paragraph 44, wherein said platinum (II) complex is
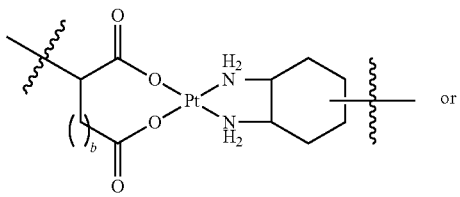 or
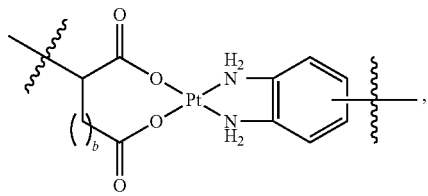,
wherein b is 0, 1, 2, 3, 4, or 5;
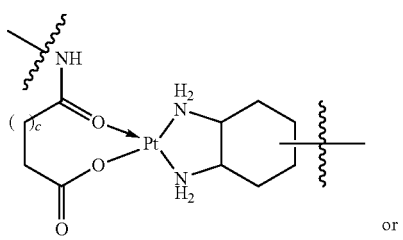
or
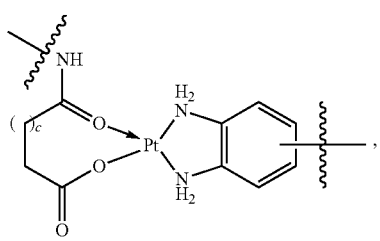,
wherein c is 0, 1, 2, 3, 4, or
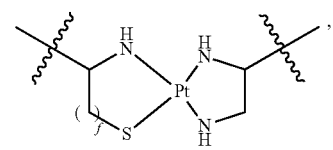,
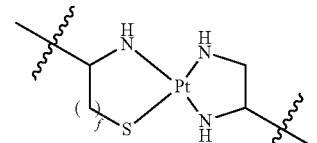,
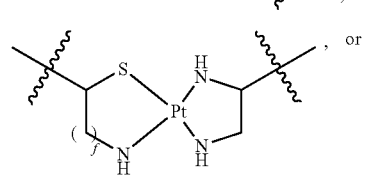, or
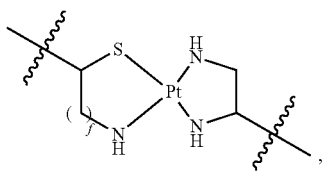,
wherein f is 0, 1, 2, 3, 4, or 5; or
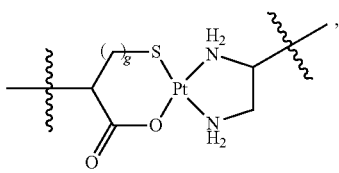,
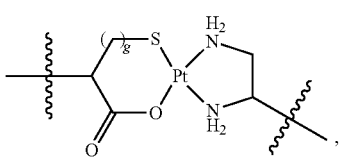,
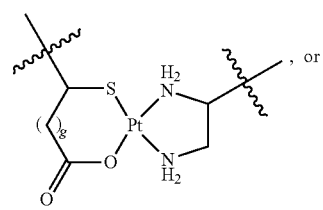, or
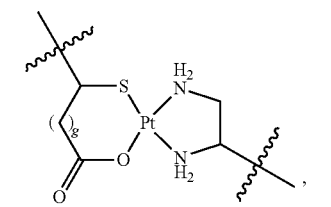,
wherein g is 0, 1, 2, 3, 4, or 5.
46. The conjugate of paragraph 44, wherein said platinum (II) complex is
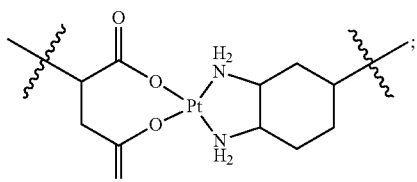
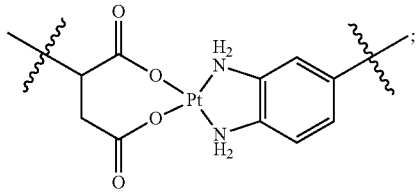;

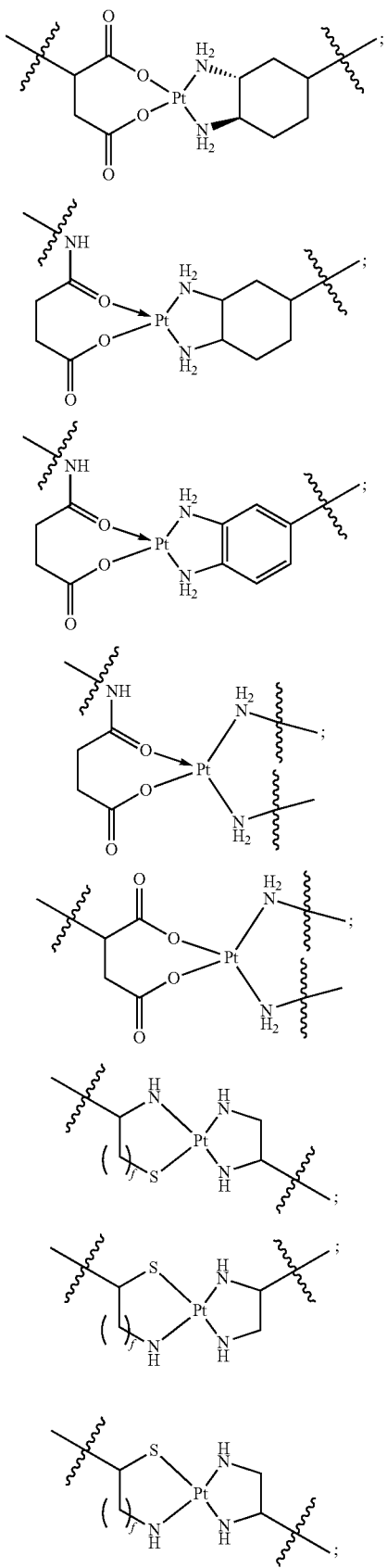

47. The conjugate of any of paragraphs 39-46, wherein said drug is an anti-cancer agent.
48. The conjugate of paragraph 47, wherein said anti-cancer agent is selected from the group consisting of Maytansinoid (DM1 and DM4); CC-1065; Adozelesin (DC1); DC4; Calicheamicins; Dolastatins; Auristatins E and F; Meamycin; Doxorubucin; Paclitaxel; Docetaxel; Laulimalide; Epothilones A and B; Discodermolide; Eleutherobin; Peloruside A; cyclophosphamide, chlorambucil, uramustine, ifosfamide, melphalan, and bendamustine; Carmustine, lomustine, semustine; Busulfan; Thiotepa; Dacarbazine; Methotrexate; 6-mercaptopurine, 6-thioguanine, pentostatin, fludarabine; 5-fluorouracil, cytarabine, leukovorin; Dactinomycin; Bleomycin; Daunorubicin; Mitomycin; Idarubicin; Plicamycin; Vincristine; Vinblastine; Vinorelbine; Etoposide; Teniposide; Asparaginase; Maitotoxin; Irinotecan (CPT-11); Fumagillin; Fumagalone; Fumarranol; O-(Chloroacetylcarbamoyl)-Fumagillol (AGM-1470, TNP-470); 27-hydroxybullatacin, derivatives and analogues thereof, and any combinations thereof.
49. The conjugate of any of paragraphs 39-48, wherein said ligand binds a protein, receptor, or cell marker on a surface of a cancer cell.
50. The conjugate of any of paragraphs 39-49, wherein said ligand binds Epidermal Growth Factor Receptor.
51. The conjugate of any of paragraphs 39-50, wherein said ligand is an antibody, antibody fragment, peptide, agonist, antagonist or aptamer.

52. The conjugate of paragraph 51, wherein said antibody is selected from the group consisting of C242 antibody (CanAg), Rituximab, Trastuzumab (Her2), Cetuximab, Bevacizumab (VEGF), Panitumumab, Alemtuzumab, Ofatumumab, Gemtuzumab (CD33), Inotuzumab (CD22), Lorvotuzumab (CD56), Brentuximab (CD30), Glembatumumab (GPNMB), epitope bind fragments thereof and any combinations thereof.

53. The conjugate of any of paragraphs 39-52, wherein said first or second linker is a hydrocarbon, polyethylene glycol (PEG), an amino acid, a peptide, or a combination thereof, said hydrocarbon or PEG being substituted or unsubstituted.

54. The conjugate of paragraph 53, wherein said first or second linker is a hydrocarbon.

55. The conjugate of paragraph 53, wherein said first or second linker is PEG.

56. The conjugate of paragraph 55, wherein said PEG has a molecular weight of between from about 200 Da to about 50 kDa.

57. The conjugate of any of paragraphs 39-56, wherein said first or second linker comprises a combination of at least one amino acid and substituted or unsubstituted PEG.

58. The conjugate of paragraph 57, wherein said first or second linker comprises two or three amino acids.

59. The conjugate of paragraph 58, wherein said amino acid is lysine.

60. A pharmaceutical composition comprising a conjugate of paragraph 1 and a pharmaceutically acceptable carrier.

61. A pharmaceutical composition comprising a conjugate of paragraph 16 and a pharmaceutically acceptable carrier.

62. A pharmaceutical composition comprising a conjugate of paragraph 21 and a pharmaceutically acceptable carrier.

63. A pharmaceutical composition comprising a conjugate of paragraph 39 and a pharmaceutically acceptable carrier.

64. A method of treating a cancer in a subject in need thereof, the method comprising administering an effective amount of a conjugate of paragraph 1.

65. A method of treating a cancer in a subject in need thereof, the method comprising administering an effective amount of a conjugate of paragraph 16.

66. A method of treating a cancer in a subject in need thereof, the method comprising administering an effective amount of a conjugate of paragraph 21.

67. A method of treating a cancer in a subject in need thereof, the method comprising administering an effective amount of a conjugate of paragraph 39.

The disclosure is further illustrated by the following examples which should not be construed as limiting. The examples are illustrative only, and are not intended to limit, in any manner, any of the aspects described herein. The following examples do not in any way limit the invention.

EXAMPLES

Example 1

Synthesis of a Hydrocarbon-linker Pt(II) Conjugate

Synthesis of a Maleimide-hydrocarbon with Blocked Lysine Intermediate (2):

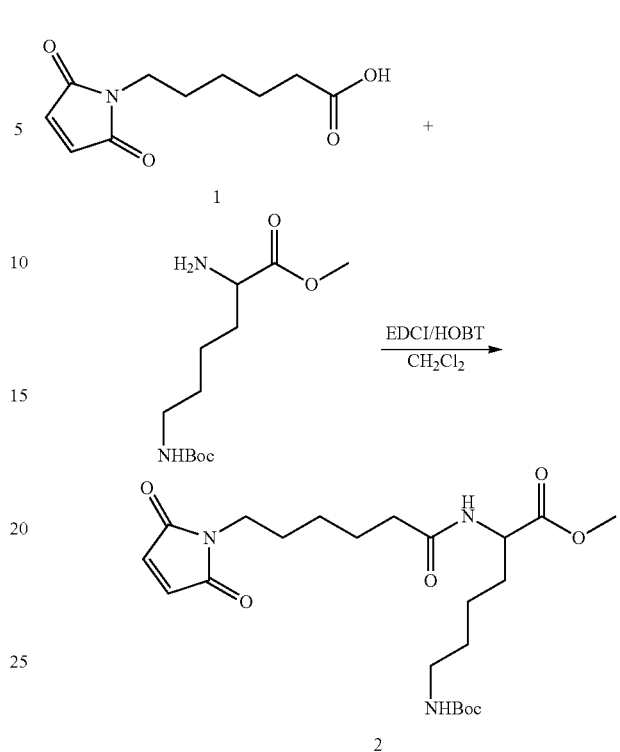

To an ice cooled solution of 6-maleimidocaproic acid (1) in $CH_2Cl_2$ (5 mL) under nitrogen atmosphere, EDCI (544.5 mg, 2.8407 mmol) and HOBT (383.7 mg, 2.8407 mmol) was added successively and stirred for 1 h. To this activated acid solution, protected lysine (630 mg, 2.1305 mmol) was added. The reaction mixture was basified with DIPEA and stirred for 12 h at room temperature, and analysed by TLC. After completion, the reaction mixture was quenched with $H_2O$ (10 mL) and twice with 0.1N HCl (25 mL), the intermediate compound 2 was extracted with twice with $CHCl_3$ (15 mL each). The combined organic layer was dried over anhydrous $Na_2SO_4$, concentrated under reduced pressure and purified by silica gel chromatography to obtain coupling product 2 with 93% yield (602 mg).

$^1$H NMR (500 MHz, $CDCl_3$) δ: 6.71 (s, 2H), 6.07 (d, J=7.1 Hz, 1H), 4.61 (dt, J=12.8, 6.5 Hz, 1H), 3.76 (s, 3H), 3.53 (dd, J=14.1, 6.9 Hz, 2H), 3.12 (s, 2H), 2.33-2.15 (m, 2H), 1.92-1.80 (m, 2H), 1.78-1.57 (m, 4H), 1.56-1.48 (m, 2H), 1.48-1.41 (m, 11H), 1.41-1.24 (m, 2H). ESIMS m/z=476 [M+Na]$^+$ for $C_{22}H_{35}N_3O_7Na$.

Synthesis of Maleimide-hydrocarbon with Activated Lysine Intermediate (3):

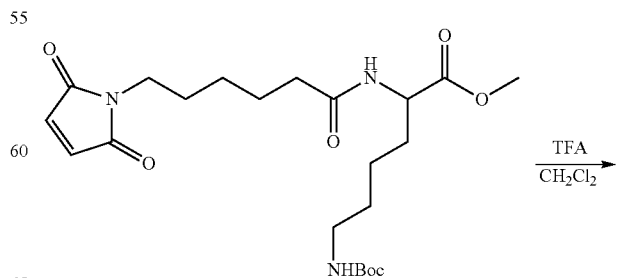

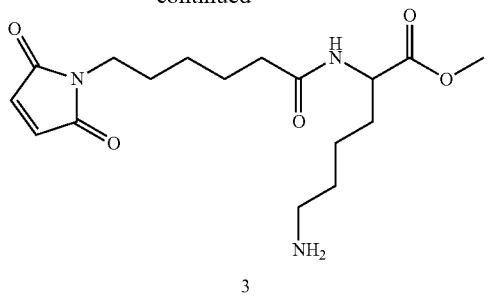

3

Next, to an ice cooled solution of intermediate 2 (450 mg, 0.9922 mmol) in CH₂Cl₂ (4 mL), 1 ml TFA was added, stirred on ice for 3 h, and analysed by TLC. Upon completion of the reaction, the mixture was concentrated under reduced pressure to obtain intermediate 3 with a quantitative yield. This intermediate was directly used for the next coupling reaction without further purification Synthesis of hydrocarbon-lysine-succinate Intermediate (4):

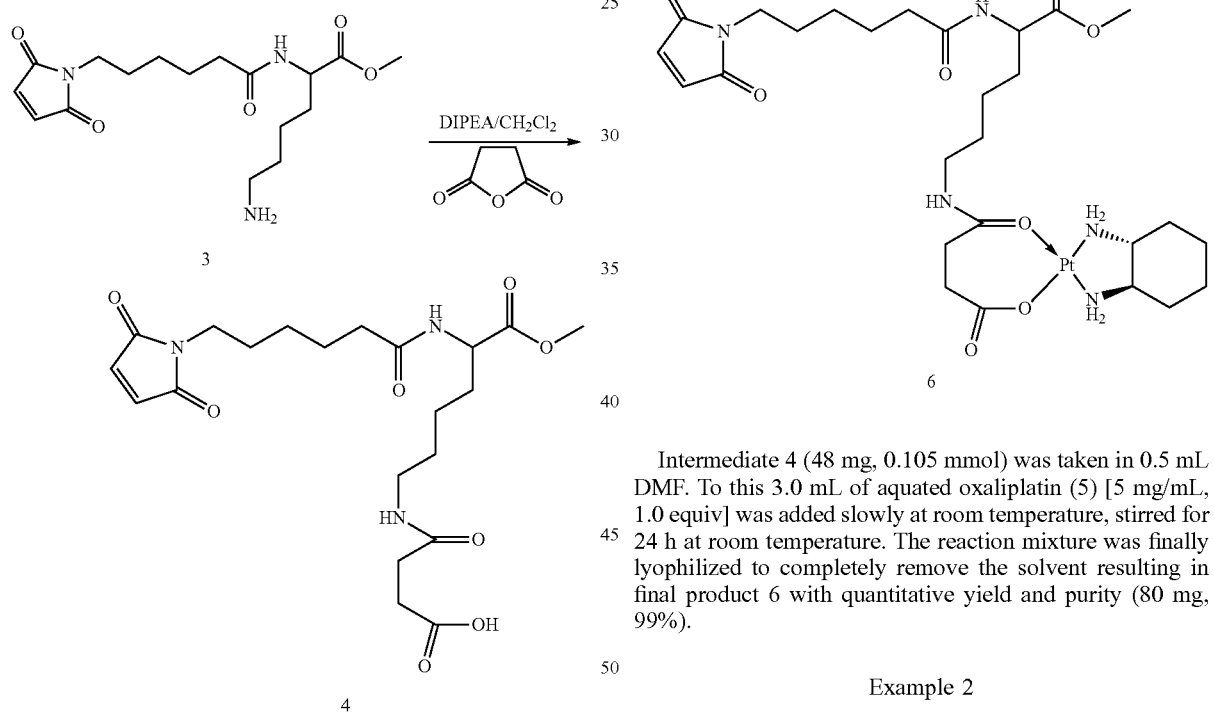

The crude starting material 3 was mixed in DMF at a 1:4 ratio, and CH₂Cl₂ (1:4 mL) at 0° C. under nitrogen atmosphere. The solution was basified with DIPEA (pH was checked), stirred for 30 minutes on ice. Succinic anhydride (250 mg, 2.5 mmol) was added to the reaction mixture, stirred for 12 h and checked by TLC. After completion, the reaction mixture was quenched with H₂O (10 mL) and twice with 0.1N HCl (25 mL each), extracted twice with CHCl₃ (15 mL each). The combined organic layer was dried over anhydrous Na₂SO₄, concentrated under reduced pressure and purified by silica gel chromatography to obtain acid intermediate 4 in with limited yield (90 mg, 20% yield).

$^1$H NMR (500 MHz, CDCl₃) δ: 6.72 (s, 2H), 6.45 (d, J=7.9 Hz, 1H), 6.35 (s, 1H), 4.62 (td, J=8.2, 4.6 Hz, 1H), 3.7 (s, 3H), 3.53 (dd, J=14.0, 6.9 Hz, 2H), 3.37-3.24 (m, 2H), 2.81-2.64 (m, 2H), 2.58-2.48 (m, 2H), 2.28 (t, J=7.4 Hz, 2H), 1.84 (td, J=12.6, 7.8 Hz, 2H), 1.76-1.50 (m, 4H), 1.47-1.19 (m, 6H). ESIMS m/z=454 [M+H]⁺ for C₂₁H₃₁N₃O₈.

Synthesis of linker Conjugated Platinum (II) complex (ligand-targeted Molecule, 6):

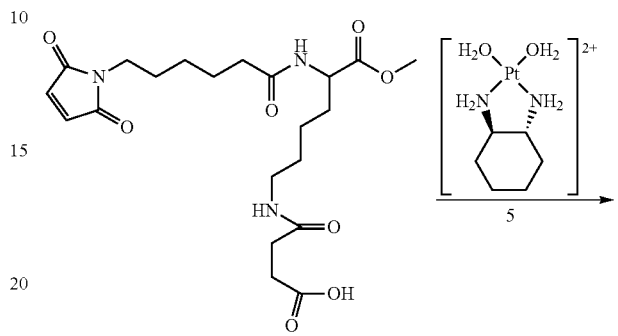

Intermediate 4 (48 mg, 0.105 mmol) was taken in 0.5 mL DMF. To this 3.0 mL of aquated oxaliplatin (5) [5 mg/mL, 1.0 equiv] was added slowly at room temperature, stirred for 24 h at room temperature. The reaction mixture was finally lyophilized to completely remove the solvent resulting in final product 6 with quantitative yield and purity (80 mg, 99%).

Example 2

Synthesis of a PEG-linker Conjugated Platinum (II) Derivative

Synthesis of a Maleimide-poly(ethylene)glycol with blocked lysine intermediate (9:

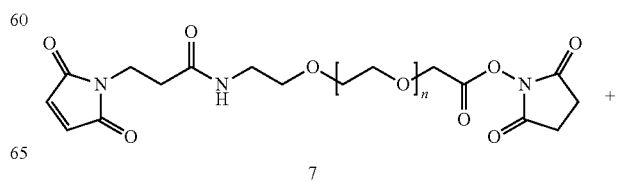

7

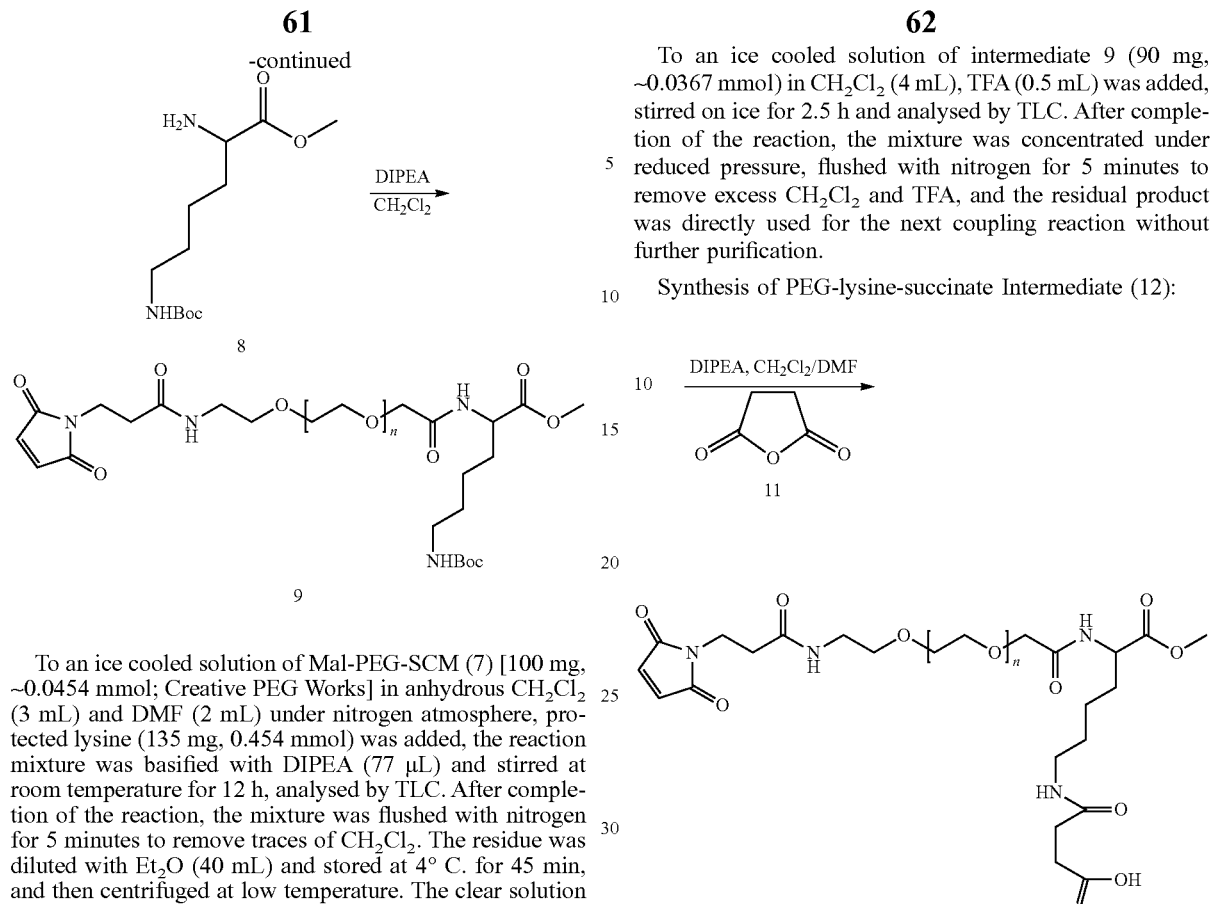

To an ice cooled solution of Mal-PEG-SCM (7) [100 mg, ~0.0454 mmol; Creative PEG Works] in anhydrous $CH_2Cl_2$ (3 mL) and DMF (2 mL) under nitrogen atmosphere, protected lysine (135 mg, 0.454 mmol) was added, the reaction mixture was basified with DIPEA (77 μL) and stirred at room temperature for 12 h, analysed by TLC. After completion of the reaction, the mixture was flushed with nitrogen for 5 minutes to remove traces of $CH_2Cl_2$. The residue was diluted with $Et_2O$ (40 mL) and stored at 4° C. for 45 min, and then centrifuged at low temperature. The clear solution was decanted, and the solid pellet was dissolved in a small volume of methanol and diluted with $Et_2O$ (40 mL), incubated at 4° C. for 45 minutes and centrifuged to get solid precipitate. The process was repeated twice to obtain pure coupling product 9 with a good yield (92 mg, purity ??HPLC not done)

Synthesis of Maleimide-pEG with activated lysine intermediate (10):

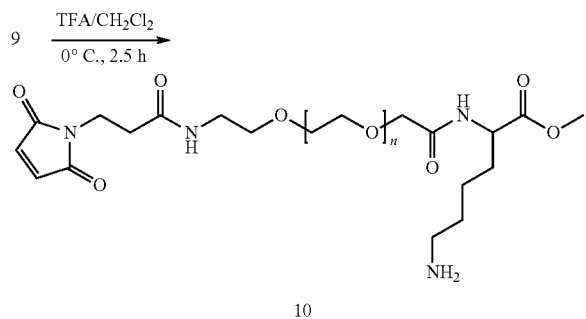

To an ice cooled solution of intermediate 9 (90 mg, ~0.0367 mmol) in $CH_2Cl_2$ (4 mL), TFA (0.5 mL) was added, stirred on ice for 2.5 h and analysed by TLC. After completion of the reaction, the mixture was concentrated under reduced pressure, flushed with nitrogen for 5 minutes to remove excess $CH_2Cl_2$ and TFA, and the residual product was directly used for the next coupling reaction without further purification.

Synthesis of PEG-lysine-succinate Intermediate (12):

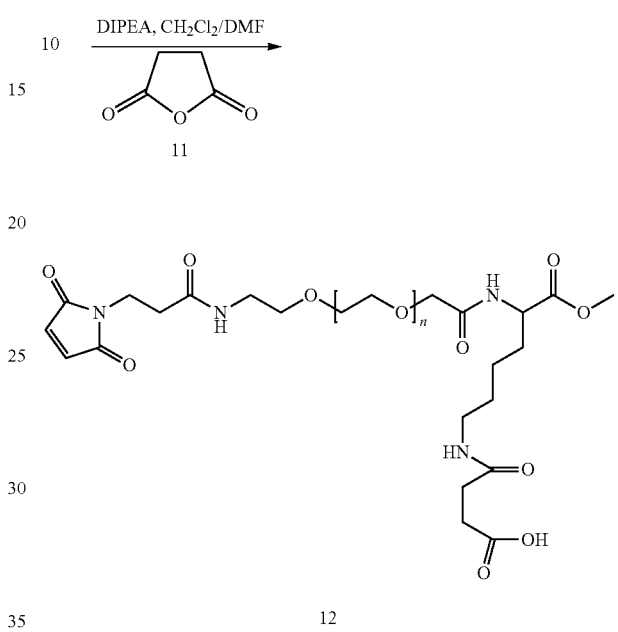

The crude starting material 10 was taken in 1:4 DMF and $CH_2Cl_2$ (1:4 mL) at 0° C. under nitrogen atmosphere. The solution was basified with DIPEA, and stirred for 30 minutes at the same temperature. Succinic anhydride 11 (200 mg, 2.0 mmol) followed by a pinch of DMAP was added to the reaction mixture and stirred for 12 h and was checked by TLC. After completion the reaction mixture was flushed with nitrogen over 10 minutes to remove $CH_2Cl_2$ and the residue was diluted with $Et_2O$ (40 mL), incubated at 4° C. for 45 min, and then centrifuged at low temperature. The clear solution was decanted and the solid residue was dissolved in methanol and diluted with $Et_2O$ (40 mL), further inubated at 4° C. for 45 minutes and centrifuged to get solid precipitate. This process was repeated twice to obtain crude coupling product which was further purified by HPLC to obtain our desired product 12 with a good yield.

Synthesis of PEG-linker Conjugated Platinum (II) Complex (ligand-targeted Molecule, 13):

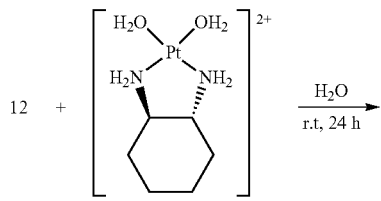

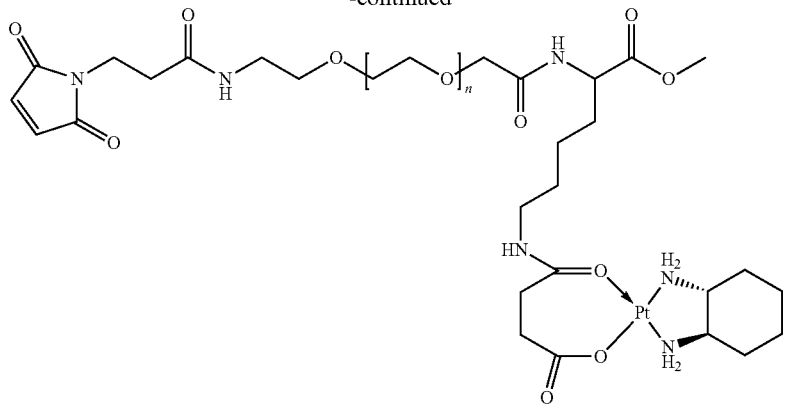

13

Acid intermediate 12 (80 mg, 0.032 mmol) was dissolved in 0.5 mL H$_2$O. To this solution aquated oxaliplatin (5 mg/mL, 1.0 equiv) was added slowly at room temperature and stirred for another 24 h. The reaction mixture was lyophilized to obtain platinum adduct 13 with good yield (80 mg).

targeting agent. All the conditions and methodologies employed are intended to be exemplary only and non-limiting. One of skill in the art is well aware of reagents and methods for conjugating molecules, e.g., linkers, drugs, and the like to antibodies.

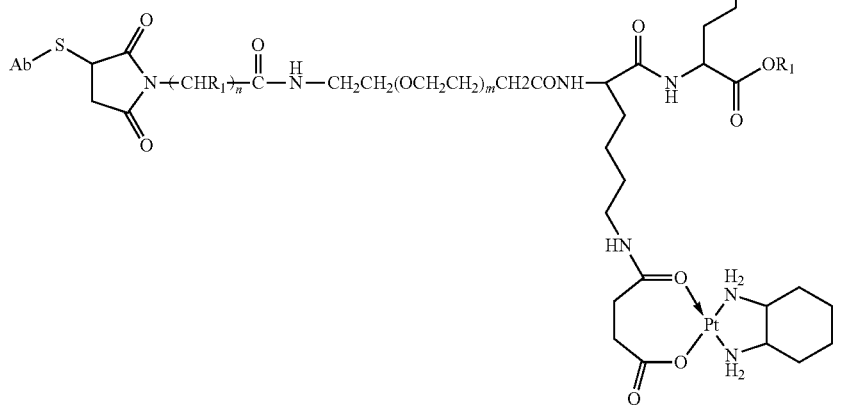

R$_1$ = H, alkyl, aryl group
n = 1-3
m - 2-100
Ab = Antibody

Example 3

Conjugation of Drug-linker Molecules to Antibodies

This example describes reaction conditions and methodologies for conjugating a drug-linker molecule of the invention (optionally including other groups, such as spacers, reactive functional groups and the like) to an antibody as a The conjugation method employed is based on introduction of free thiol groups to the antibody by reducing the inter-chain cysteines with reducing agents, followed by reaction of the drug-linker molecule with an active maleimide group. Towards this end, the antibody to be conjugated was buffer exchanged into PBS buffer pH 7.4 and concentrated to 8-10 mg/ml. The inter-chain cysteines were reduced by addition of DTT or 2-MEA to the antibody. The amount of reducing agent to be added was determined in preliminary experiments. In the optimization experiments, a titration of increasing amounts of reducing agent was added to the antibody. After incubation with the antibody for one hour at 37° C., the partially reduced antibody was purified and desalted of DTT or 2-MEA (Amicon Ultra, 30K MWCO). The number of thiol groups introduced was determined by reaction with dithionitro benzoic acid (DTNB). Reaction of thiol groups with DTNB results in a mixed disulfide and nitrothio benzoic acid (TNB) product which is spectrophotometrically detected at 412 nm. The concentration of protein in the samples was accurately determined by the absorbance at 280 nm.

Typically a thiolation level of 4-6 thiol groups per antibody is optimal for conjugation. For example, with one particular antibody this was achieved through adding a 5 fold molar excess of DTT followed by incubation at 37° C. for 1 hour. Antibody to be conjugated was therefore incubated with DTT at the desired molar ratio, then desalted into conjugation buffer (PBS, pH7.4, 10 mM ETDA). The thiolated material was maintained on ice whilst the number of thiols introduced was quantitated as described above.

To the mildly reduced antibody, the drug-linker molecule containing an active maleimide group was added at a 30-fold molar excess per thiol. The linker-drug conjugate was dissolved in 10% (v/v) DMSO in PBS (or PBS buffer alone). This stock solution of drug-linker was added to the thiolated antibody.

The conjugation reaction was carried out over night at 4° C. in PBS buffer with mixing. Next day, 3 ml PBS buffer was added to the reaction mix, then it was desalted and concentrated by diafiltration (Amicon Ultra, 30K MWCO) by centrifuging at 2000×g for 15 minutes. This step was repeated at least 4 times, and finally the conjugate was analysed for protein and platinum content by UV and atomic absorption spectroscopy.

Example 4

Binding of ADC on the Target Cell Surface Receptor

For testing EGFR receptor binding by the mAb-PEG-linker-Pt conjugate, 96-well microtiter Maxisorb plates (Nunc, PIERCE) were coated with 80-100 µl of 2 mg/L of EGFR-ECD (in PBS buffer) for overnight at 4° C. The wells were washed with PBST (PBS containing 0.1% Tween-20) and blocked with 2% Casein in PBS for 1-2 h at RT. The wells were further washed with PBST as above and serially diluted antibody drug conjugate (ADC) was added to the respective wells, and incubated for 2 h at room temperature. After a final wash with PBST as above, the goat anti-human IgG1-HRP antibody (1:10000 diluted) was added and incubated for 1 hr at room temperature. Wells were washed and the ABTS reagent was added. The colour development was stopped by adding 100 µl of 1% SDS to each well. Reading of the plate was performed at 415 nm with a microplate reader (BioRad).

Example 5

Analysis of PEG Content on the ADC

The PEG content in the ADC was analysed by ELISA and SDS-PAGE. For the ELISA, Maxisorp microtiter plate was coated with varying concentration of ADC and incubated over night at 4° C. The wells were washed with wash buffer (PBS, 0.1% Tween-20) and blocked with 2% Casein/PBST for 2 h at room temperature. After another wash as above, 70-100 µl of the mouse biotinylated anti-PEG monoclonal detection antibody (1: 500-1000 diluted) was added to the wells, incubated for 1 h at room temperature. Wells were washed again with PBST, 100 µl of streptavidin-HRP was added and incubated for 30-45 min. Finally, wells were washed with PBS and the ABTS reagent was added. The colour development was stopped by adding 100 µl of 1% SDS to each well, and plate was read at 415 nm.

The presence of PEG on the ADC was also qualitatively determined by running the samples on a 10% SDS-PAGE under reducing and non-reducing conditions.

Example 6

Analysis of the Cytotoxicity of the ADC

The cytotoxic potency of the anti-cancer platinum agents conjugated to the antibody of the invention was assayed using the well established MTT cell proliferation assay. This is a convenient method for quantitating cellular viability, and can accommodate large numbers of compounds.

For the MTT assay, the metastatic breast cancer cell line MDA-MB-231 and the colorectal cell line HT-29 were cultured in DMEM media containing 10% heat inactivated fetal calf serum (FCS), 2 mM L-glutamine, 50 IU/mL penicillin and 50 µg/mL streptomycin.

For testing the Cetuximab-PEG linker-Pt or the Cetuximab-hydrocarbon linker-Pt conjugates, cells were plated to 96-well microtiter plates (3000-5,000 cells/well). Serial dilutions (3-fold increments) of platinum drug (as a positive control) or test compounds were made, and 100 µl of compounds were added per well. The survival profile of the cells was measured with the MTT assay 96 hr after plating.

Example 7

Figure 12A:
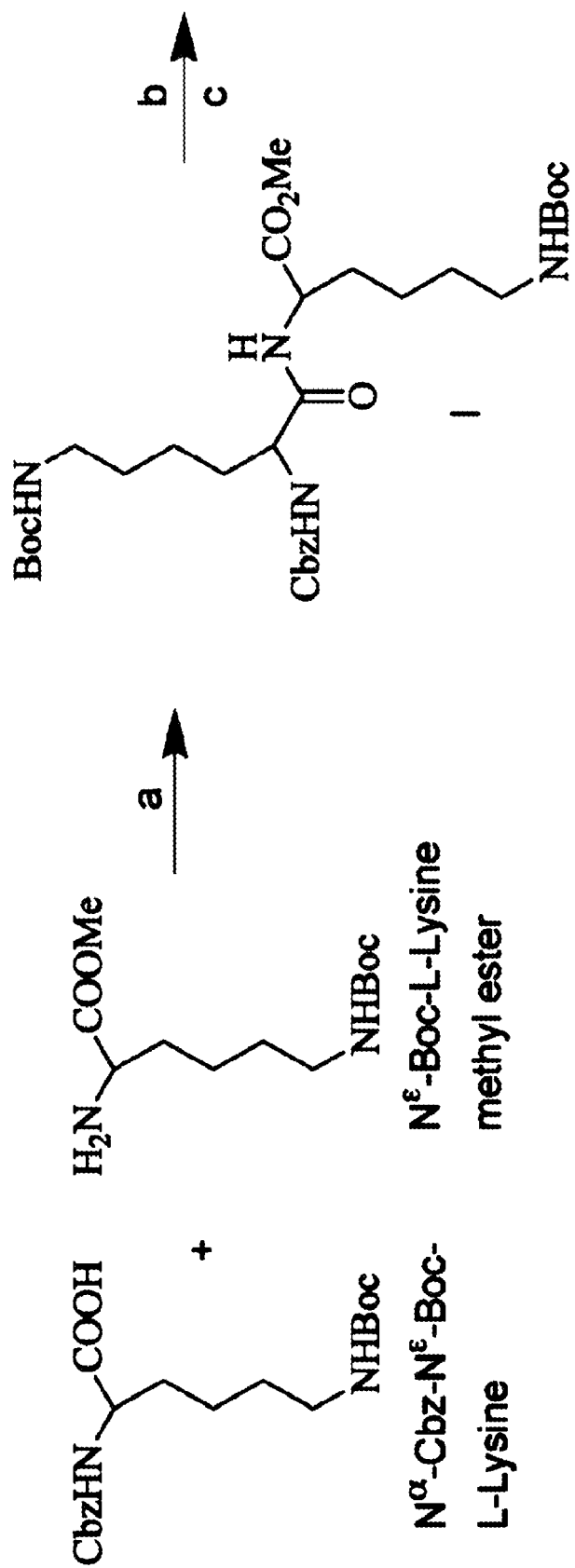
FIGS. 12A and 12B are synthesis scheme for the synthesis of tri-lysinated Pt(II) analogs conjugated to the anti-EGFR monoclonal antibody. Reagents and Conditions: a) HoBT, EDCI, Dry DCM, DIPEA, 12 h, rt; b) H2, Pd, Ethylacetate, 6 h, rt; c) HoBT, EDCI, Dry DCM, Na-Cbz-Ne-Boc-L-Lysine, d) H2, Pd, Ethylacetate, 6 h, rt; e) HoBT, EDCI, HOOC-PEG-Mal, Dry DCM, DIPEA, 12 h, rt; f) TFA, Dry DCM, 3 h, 0° C.; g) succinic anhydride, pyridine, Dry DCM, 12 h, rt; h) Cis-diamminedihydro platinum(II), DMF, H2O, 24 h, rt; i) Antibody-SH (EGFRmAb-SH).
Figure 12A:
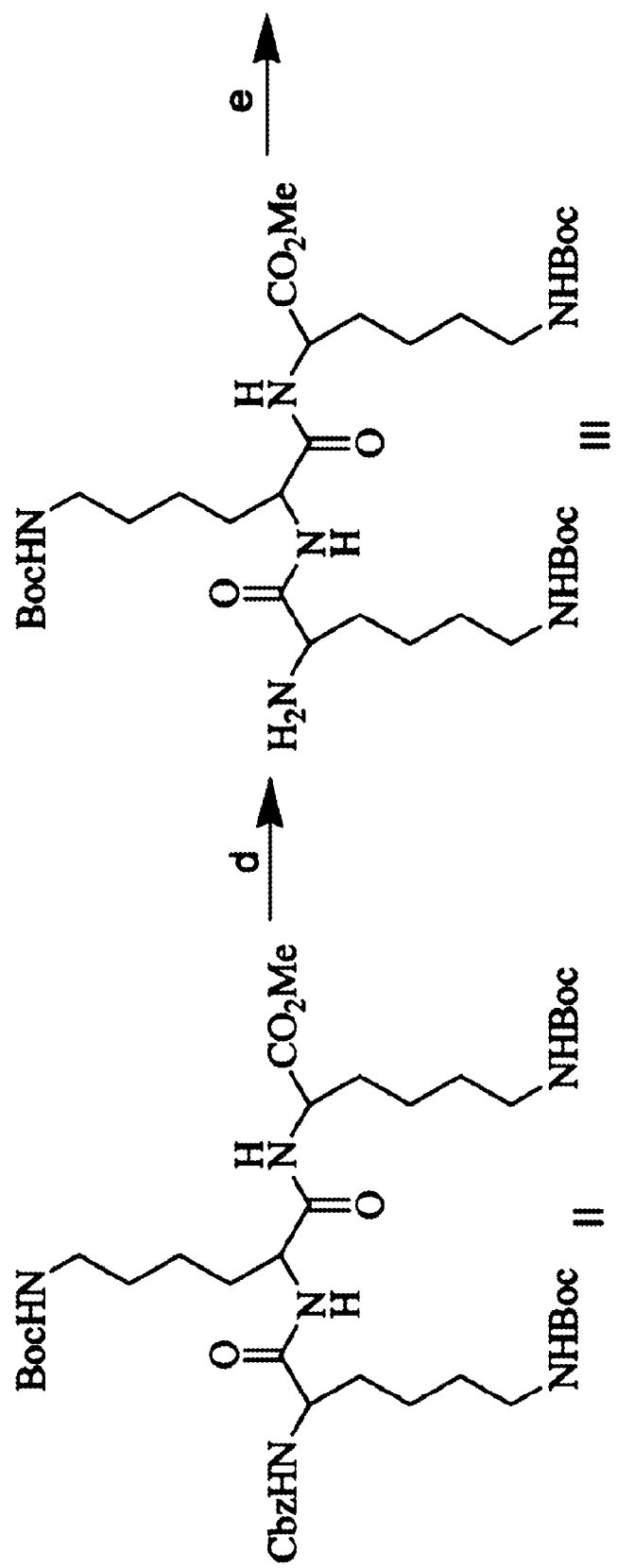
Figure 12A:
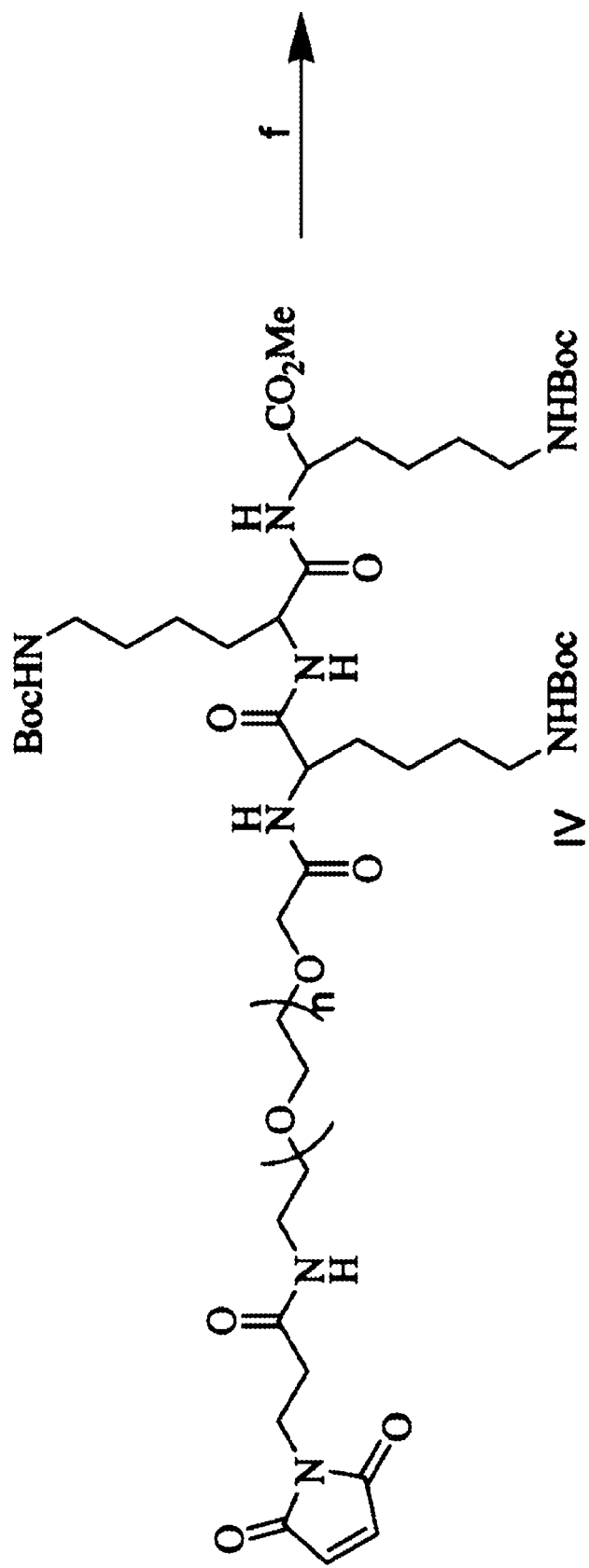
Figure 12A:
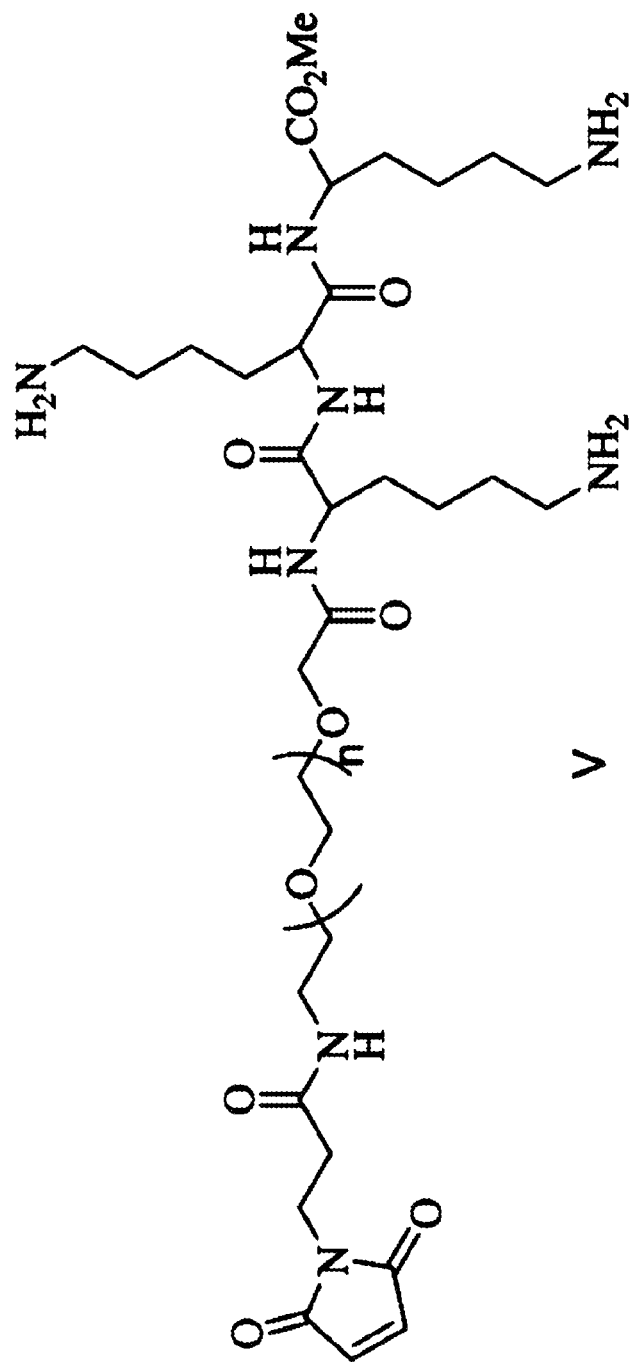
Figure 12B:
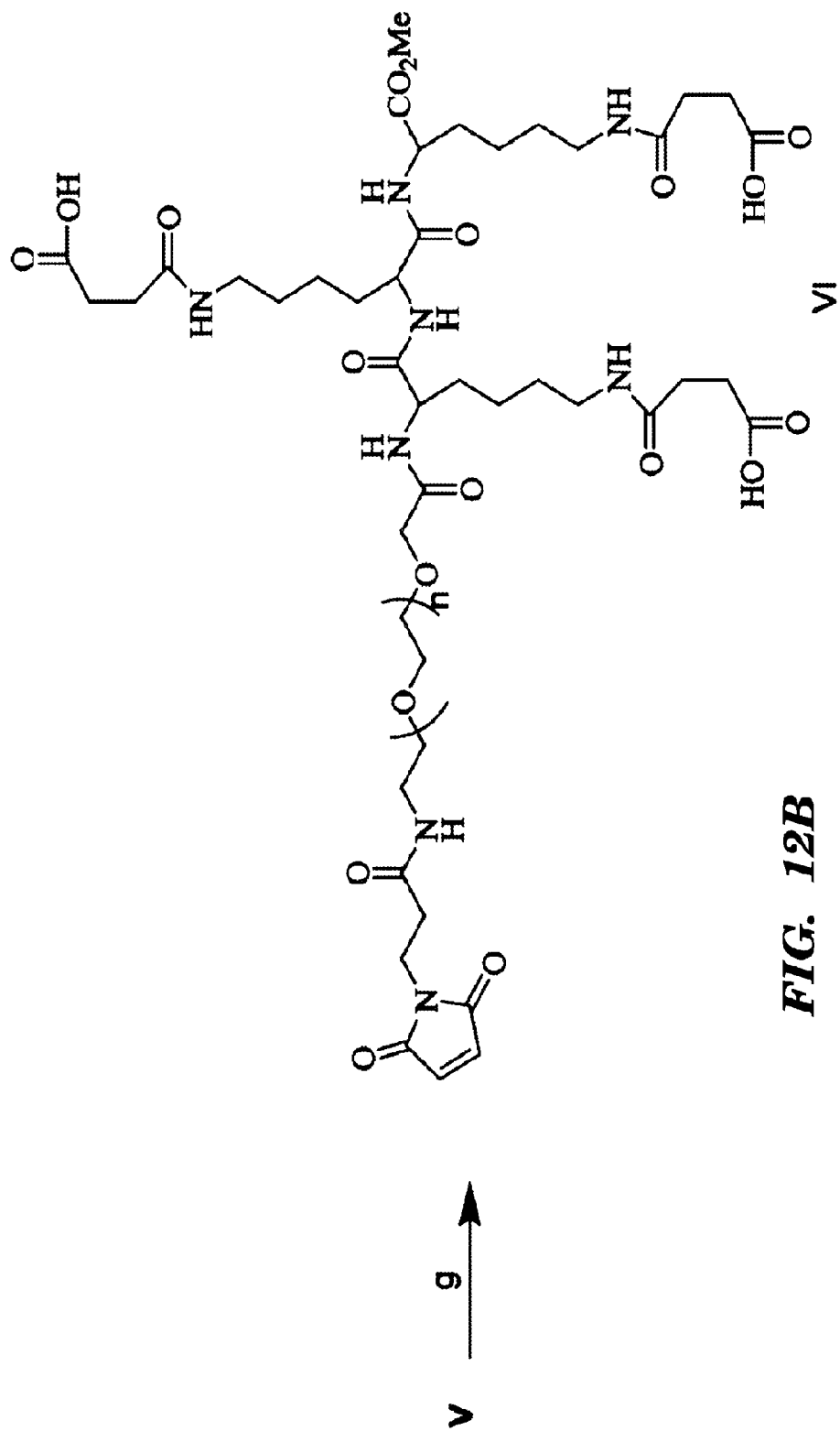
Figure 12B:
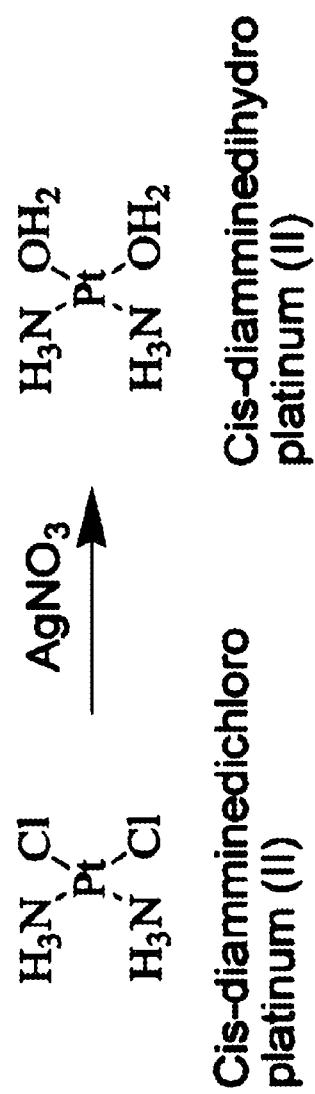
Figure 12B:
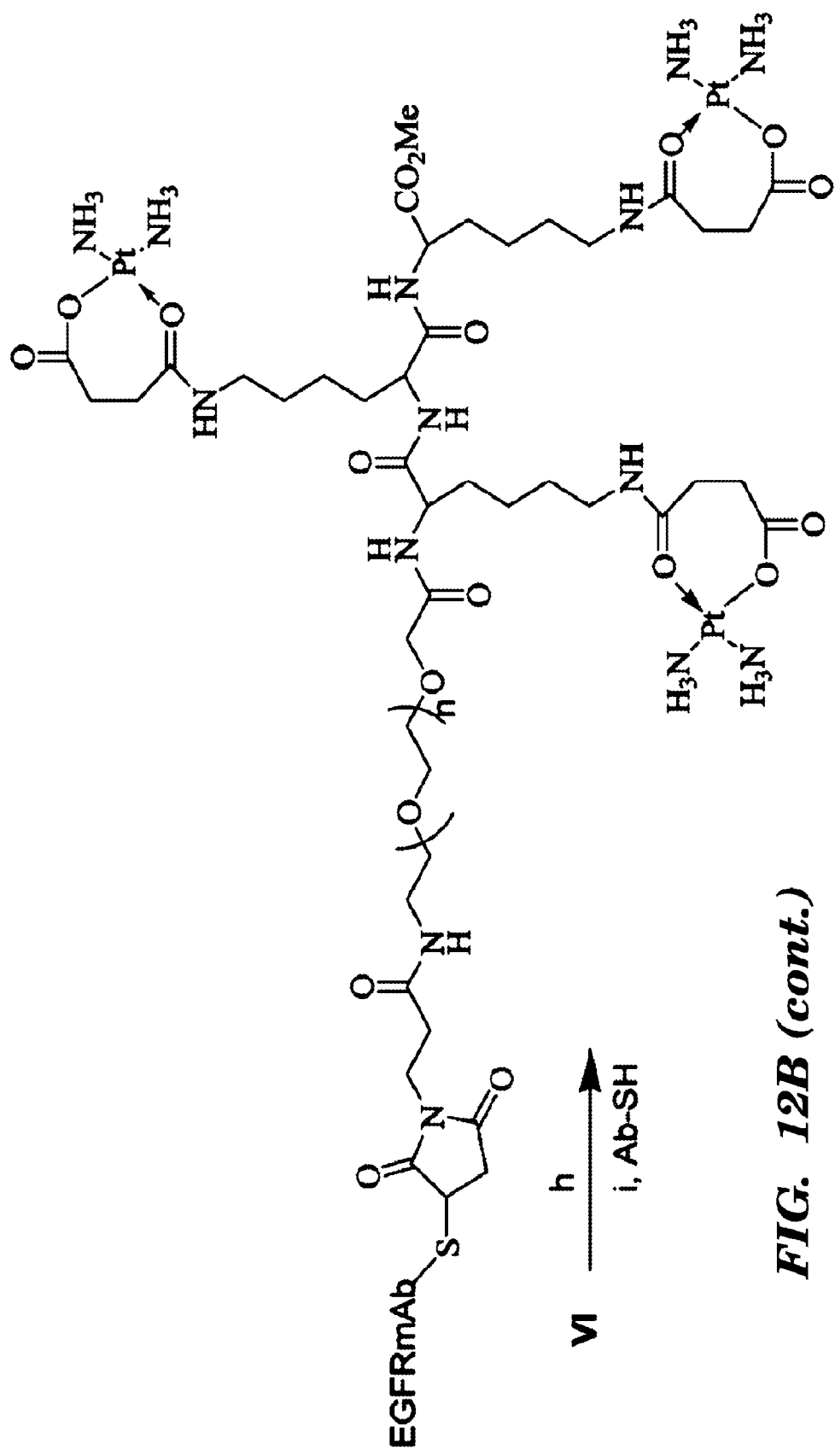

Synthesis of Tri-lysine Containing Ligand-Targeted Molecule Conjugated with Antibody Trilysine containing ligand-targeted molecule conjugated with antibody can be synthesized according to the method shown in FIGS. 12A and 12B. Shown is a schematic representation of the synthesis of a tri-lysinated Pt(II) analogs conjugated to the anti-EGFR monoclonal antibody. Reagents and Conditions: a) HoBT, EDCI, Dry DCM, DIPEA, 12 h, rt; b) H2, Pd, Ethylacetate, 6 h, rt; c) HoBT, EDCI, Dry DCM, Na-Cbz-Ne-Boc-L-Lysine, d) H2, Pd, Ethylacetate, 6 h, rt; e) HoBT, EDCI, HOOC-PEG-Mal, Dry DCM, DIPEA, 12 h, rt; f) TFA, Dry DCM, 3 h, 0° C.; g) succinic anhydride, pyridine, Dry DCM, 12 h, rt; h) Cis-diamminedihydro platinum(II), DMF, H2O, 24 h, rt; i) Antibody-SH (EGFRmAb-SH).

Example 8

Synthesis of Ligand-targeted Conjugates Using Pt (II) as Part of a Linker

Figure 13A:
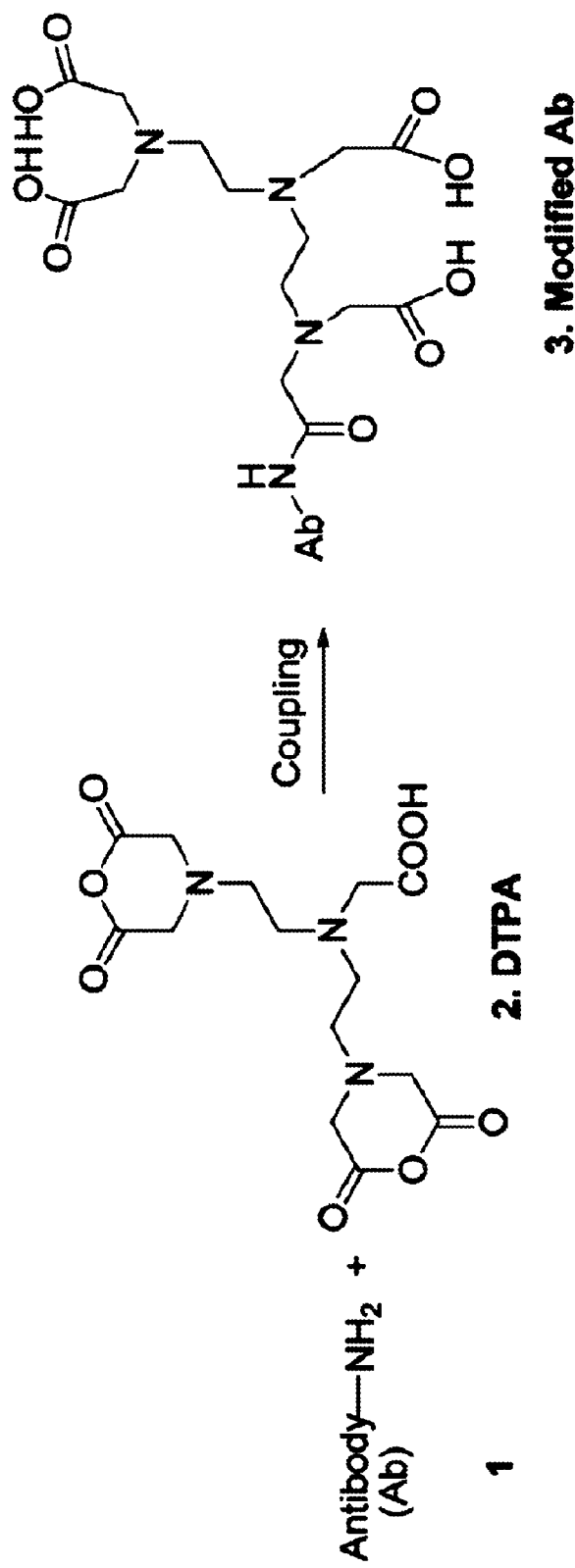
FIGS. 13A and 13B are schematic representation of the scheme for the synthesis of a ADC using Pt(II) coordination linker-drug complex.
Figure 13B:
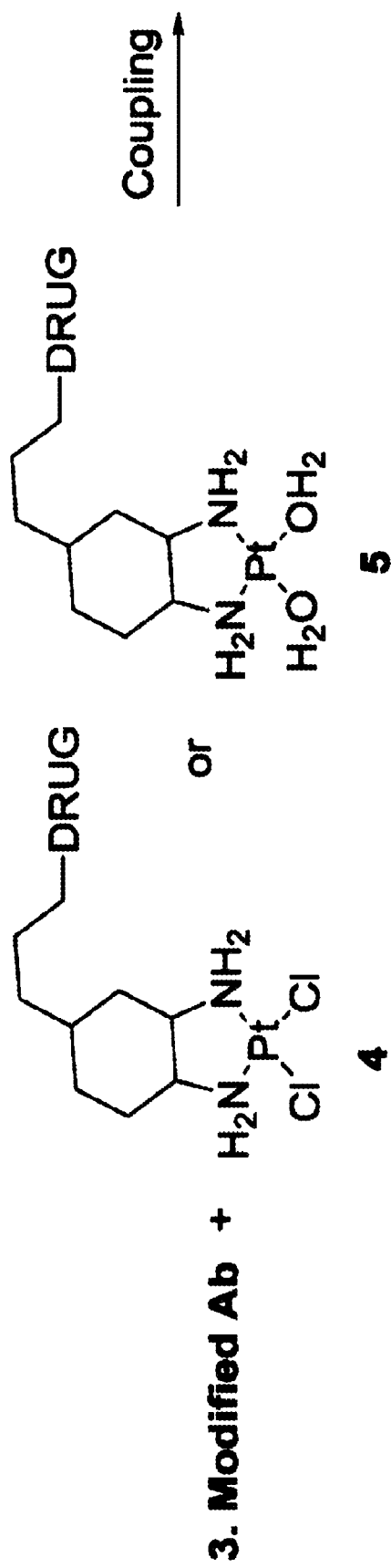
Figure 13B:
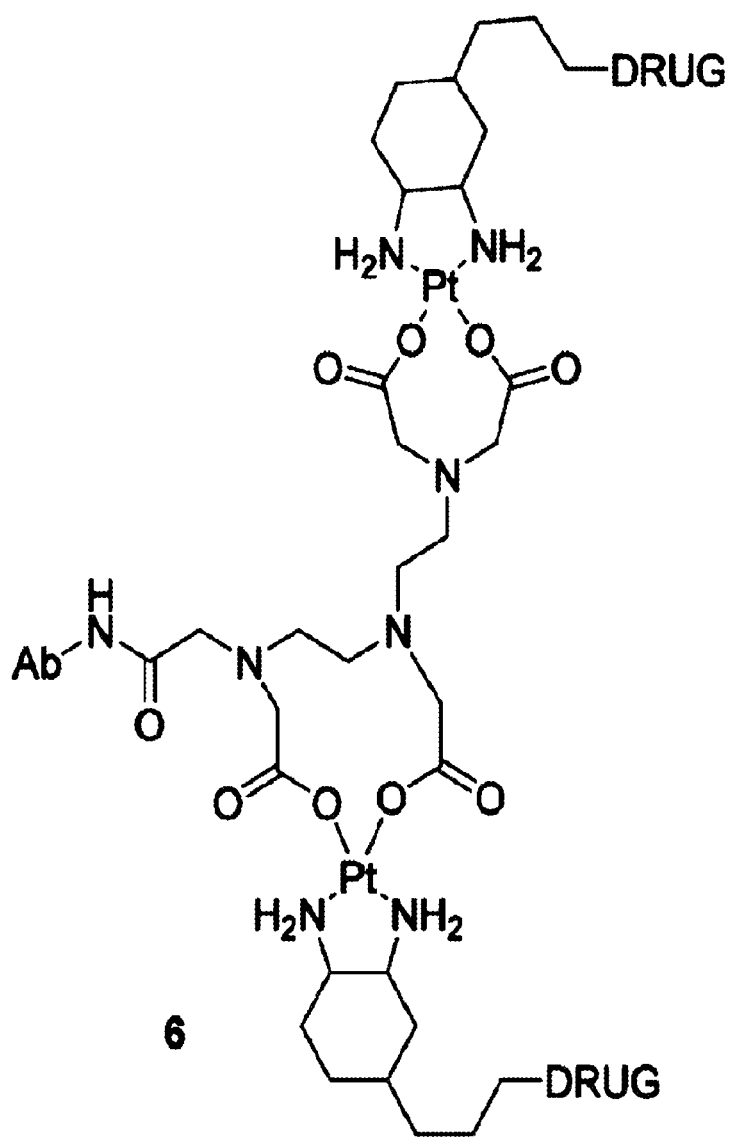
Figure 13B:
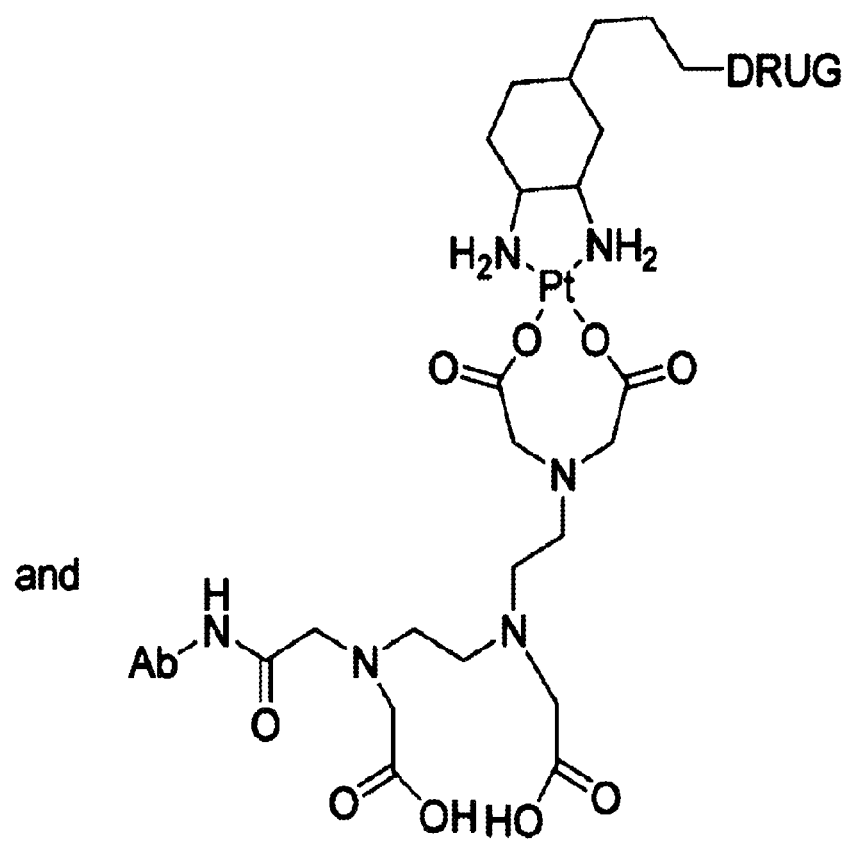

A general process for the synthesis of a ADC using Pt(II) coordination linker-drug complex is shown in FIGS. 13A and 13B. Step 1: Coupling of a metal chelator to the antibody by conjugating via the amine groups of lysine is carried out using the method outlined in FIG. 13A. Step 2: Conjugating a cytotoxic drug to the antibody-chelator complex through Pt(II) analogs is carried out according to the method outlined in FIG. 13B.

Example 9

Figure 14A:
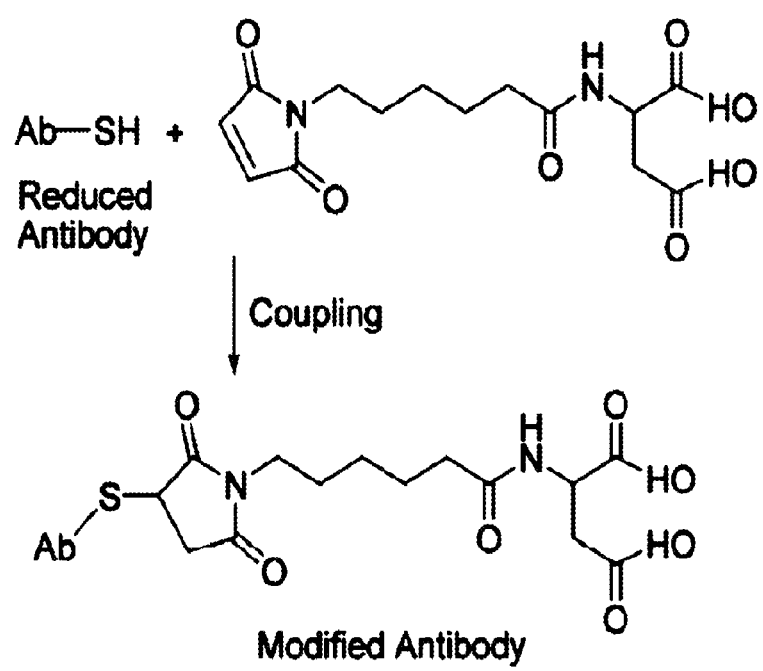
FIGS. 14A-14C are schematic representation of the scheme for the synthesis of an antibody conjugated to the cytotoxic drug 27-hydroxybullatacin using Pt(II) coordination linker (steps 1-3).
Figure 14B:
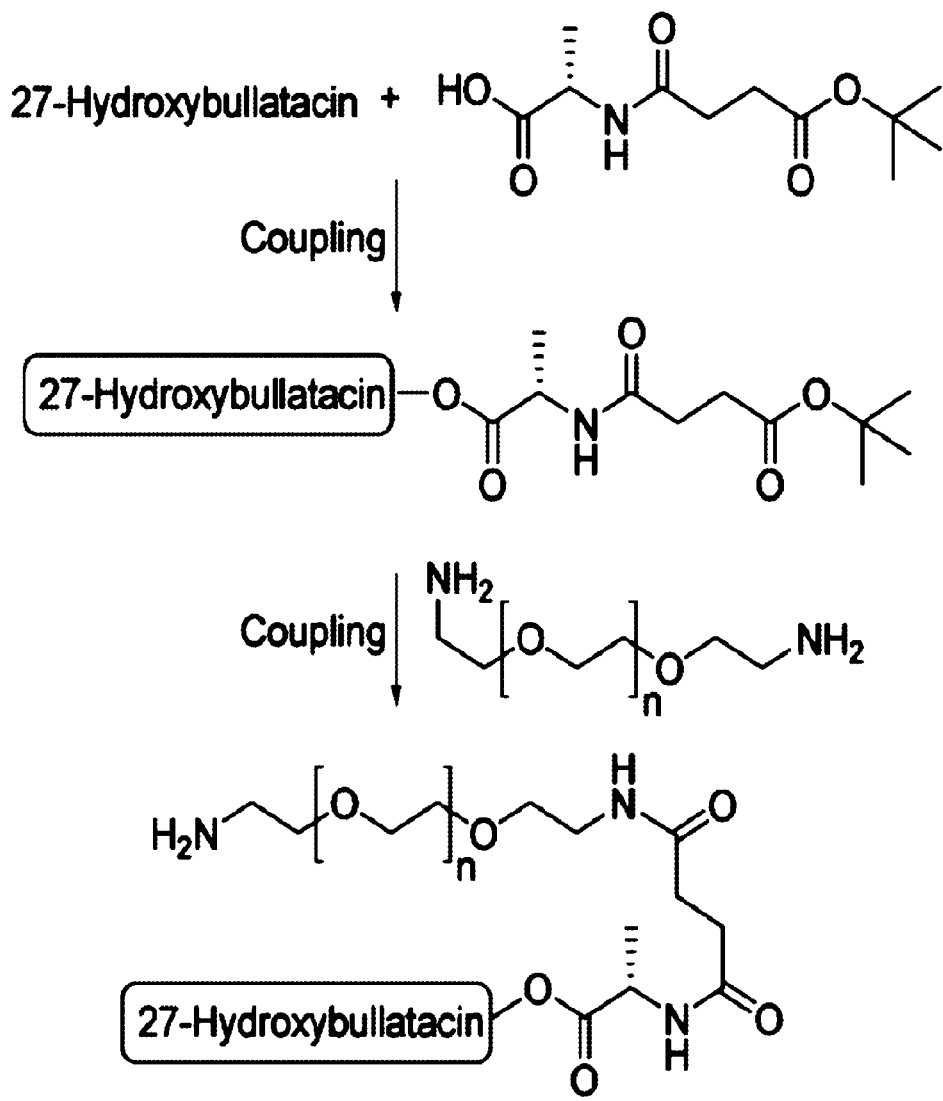
Figure 14B:
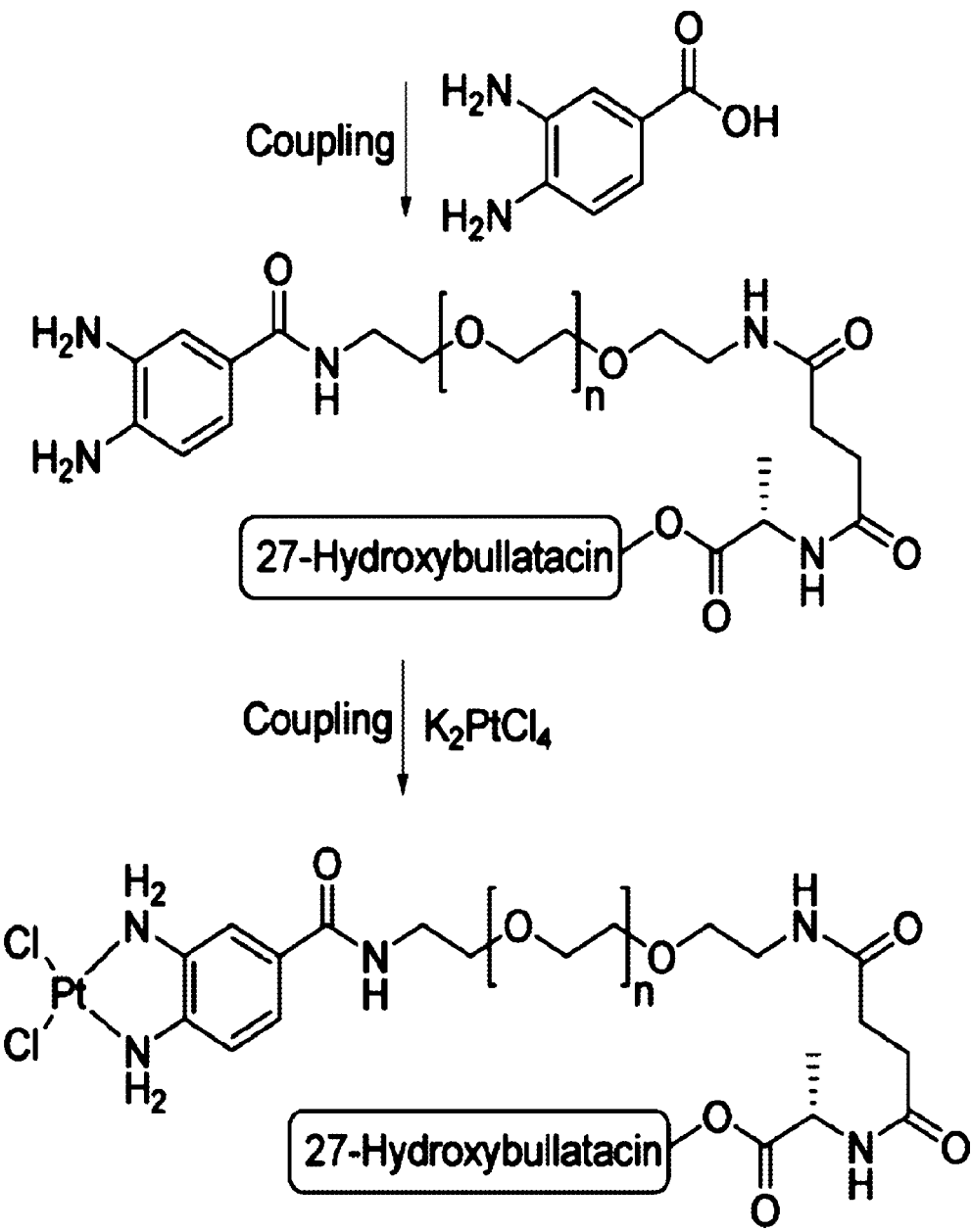
Figure 14C:
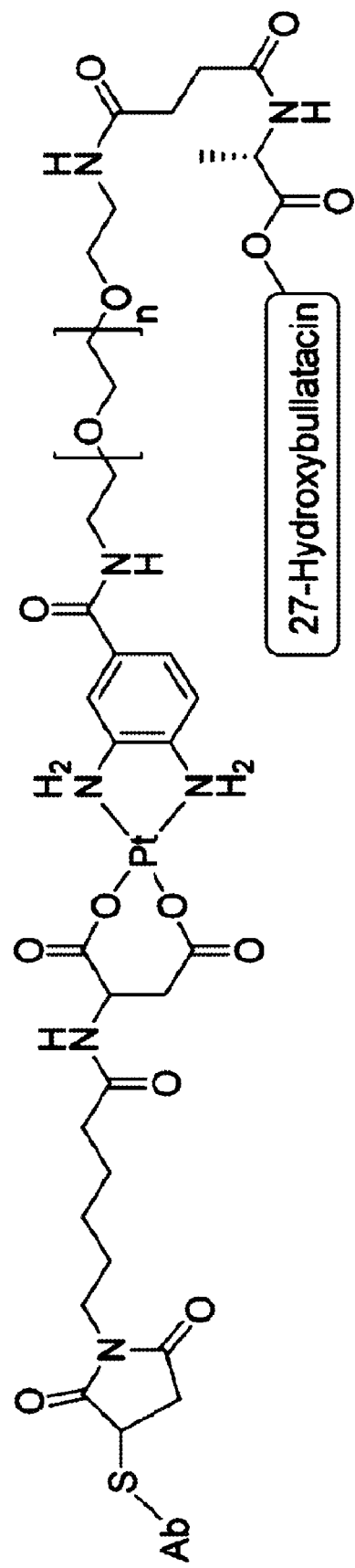

Synthesis of a ADC Using the Pt(II)-coordination Linker to Conjugate the Cytotoxic Drug 27 Hydroxybullatacin Synthesis of a ADC using the Pt(II)-coordination linker to conjugate the cytotoxic drug 27-Hydroxybullatacin can be carried out using the method outlined in FIGS. 14A-14C. FIGS. 14A-14C show a schematic representation of the synthesis of an antibody conjugated to the cytotoxic drug 27-hydroxybullatacin using Pt(II) coordination linker (steps 1-3). Step 1: Synthesis of modified antibody is according to the method outlined in FIG. 14A. Steps 2 and 3 of the synthesis can be carried out as outlined in FIGS. 14B and 14C respectively.

Example 10

Figure 15A:
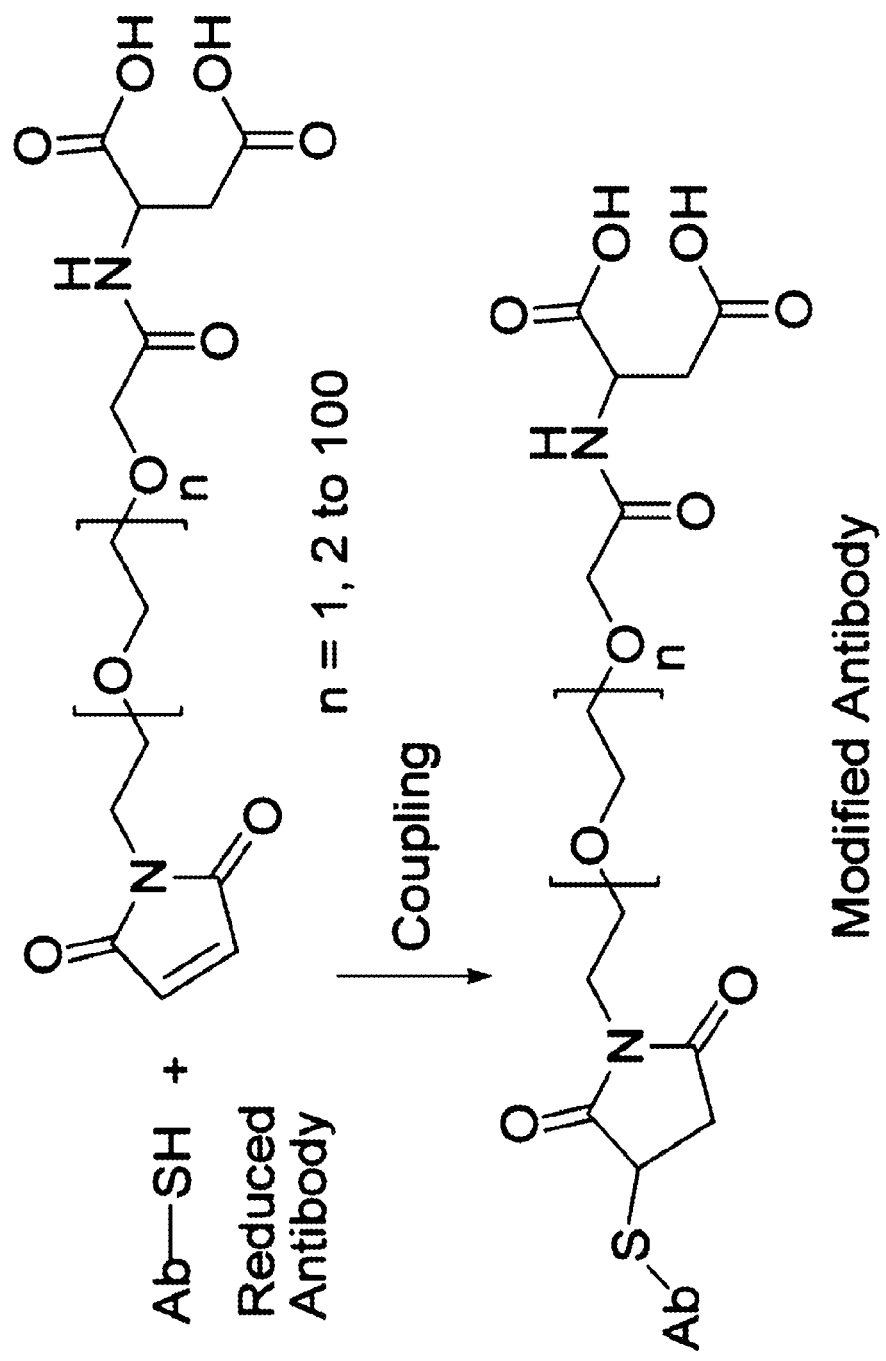
FIGS. 15A-15C are schematic representation of the scheme for the synthesis of an antibody conjugated to the cytotoxic drug meayamycin using Pt(II) coordination linker (steps 1-3).
Figure 15B:
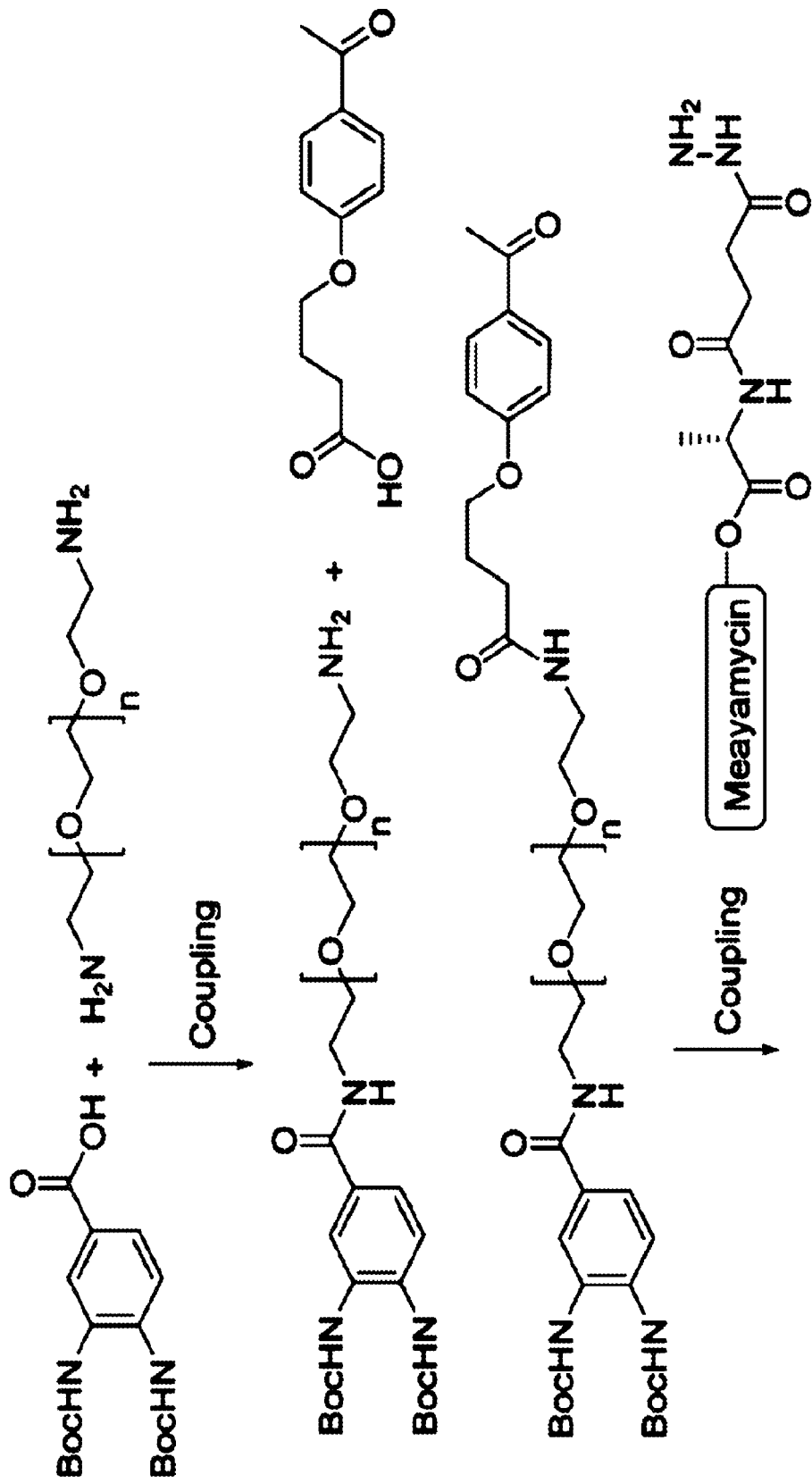
Figure 15B:
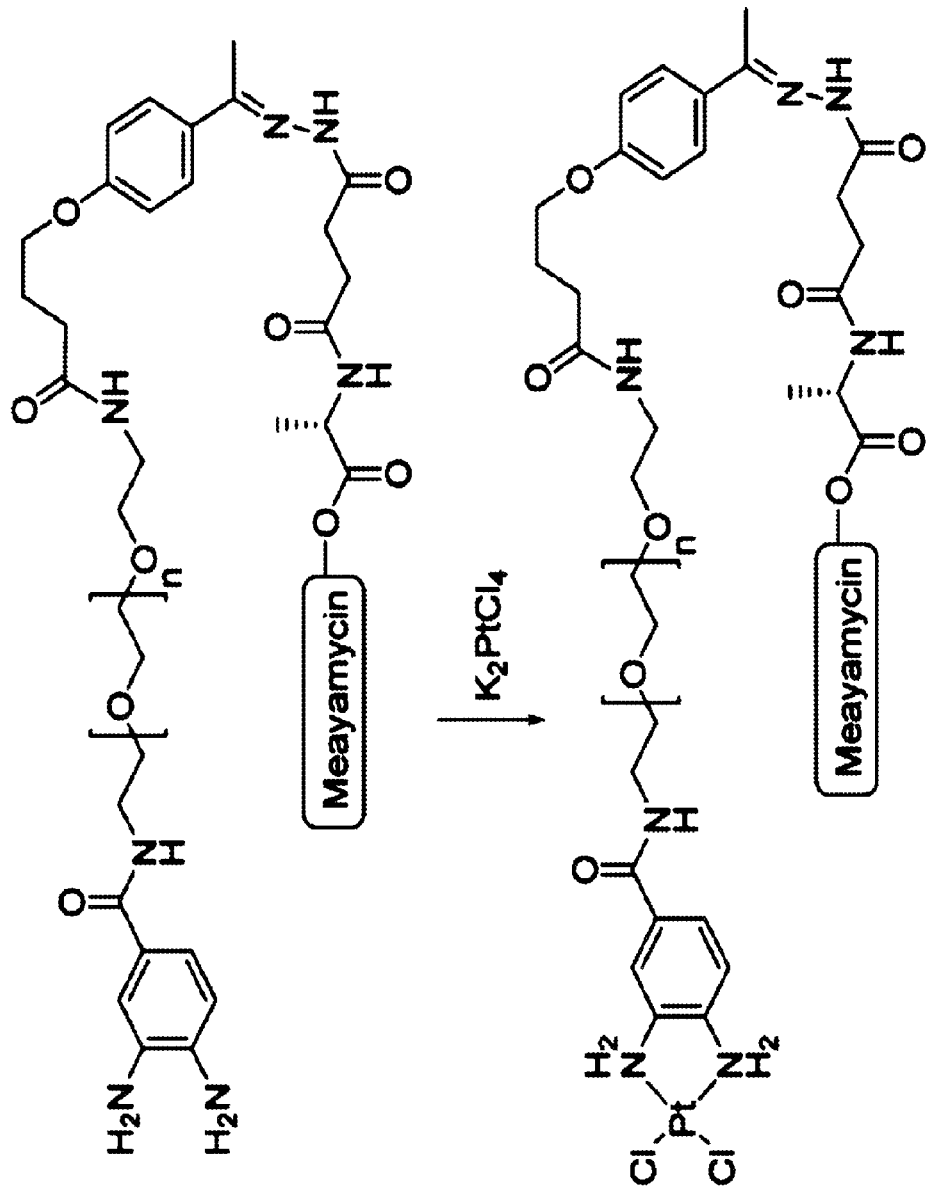
Figure 15C:
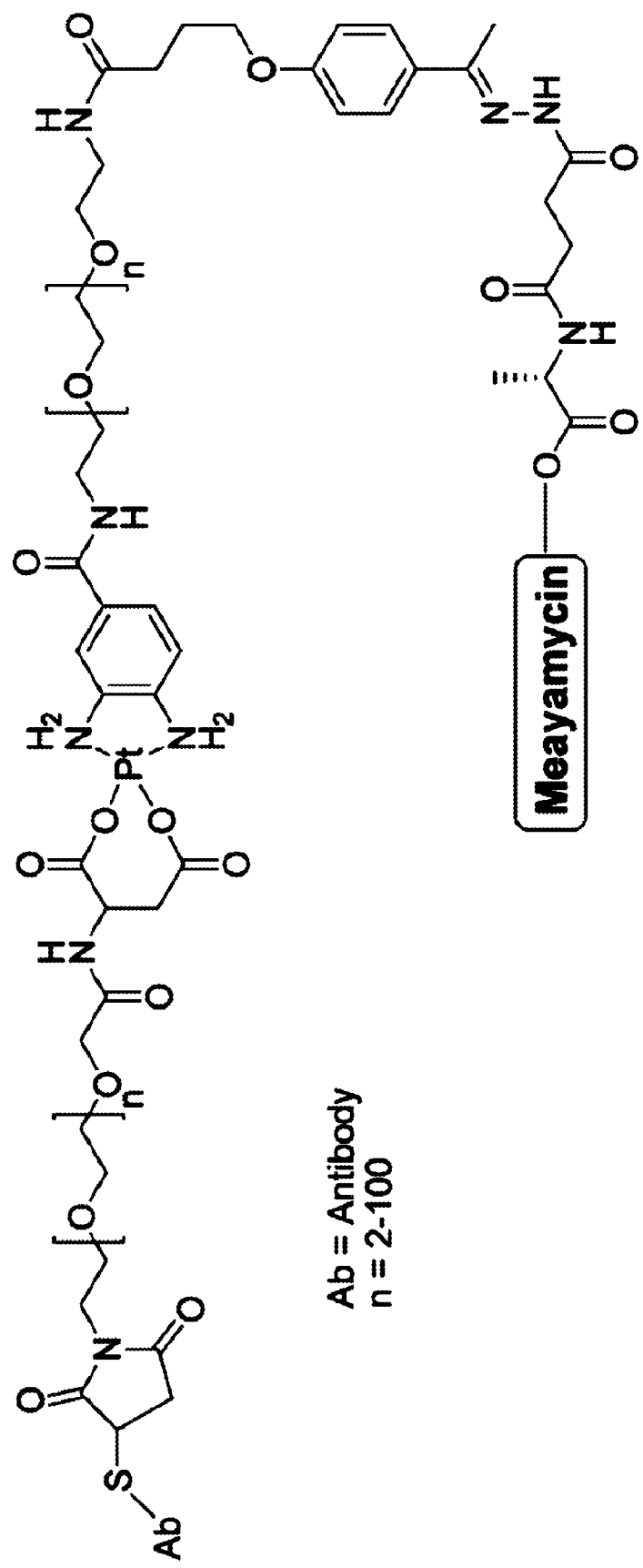
Figure 16A:
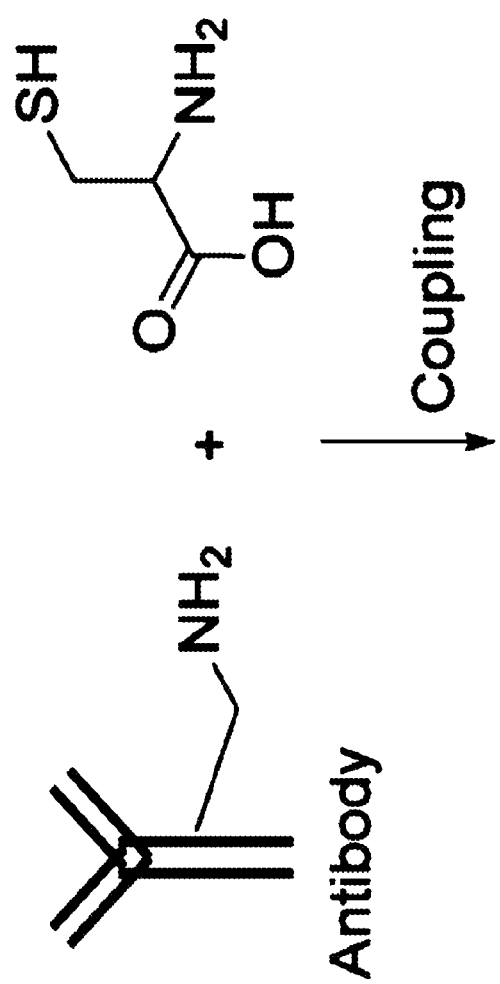
FIGS. 16A-16C are schematic representations of antibody-drug conjugates using a non-cleavable, platinum comprising linker.
Figure 16A:
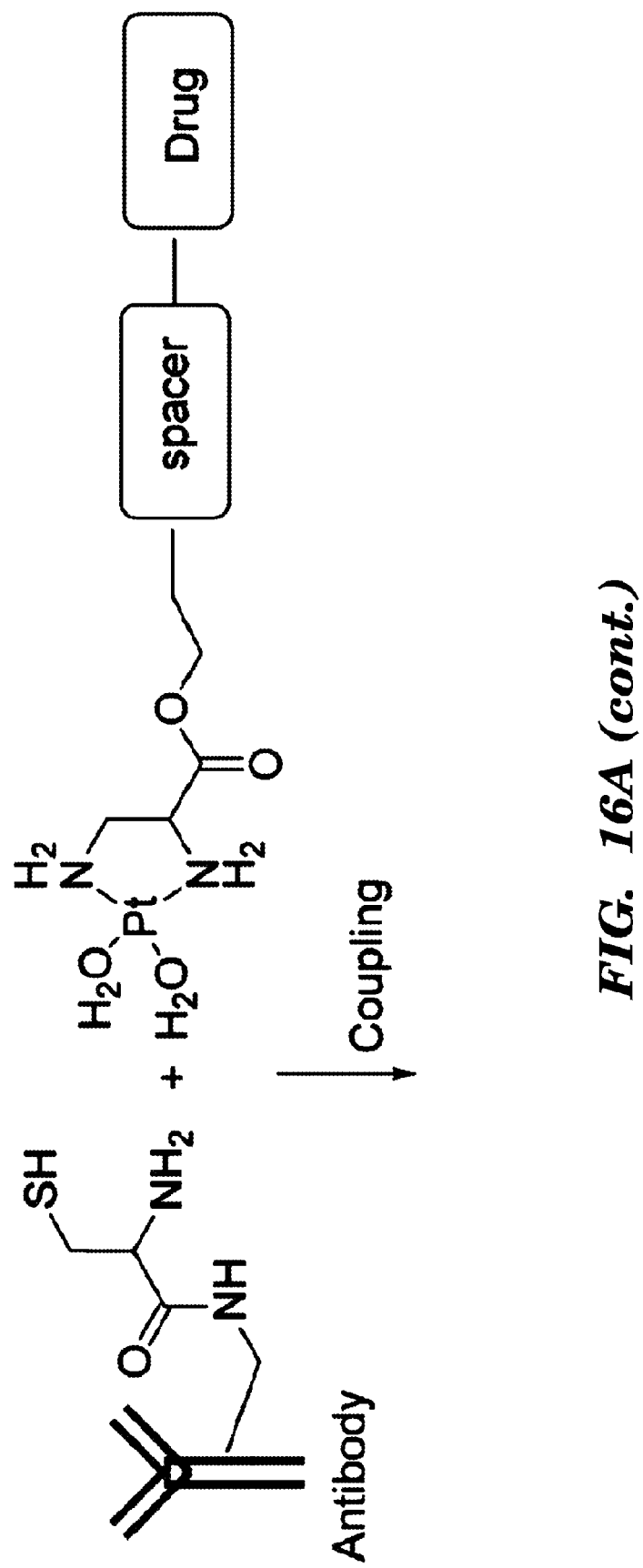
Figure 16A:
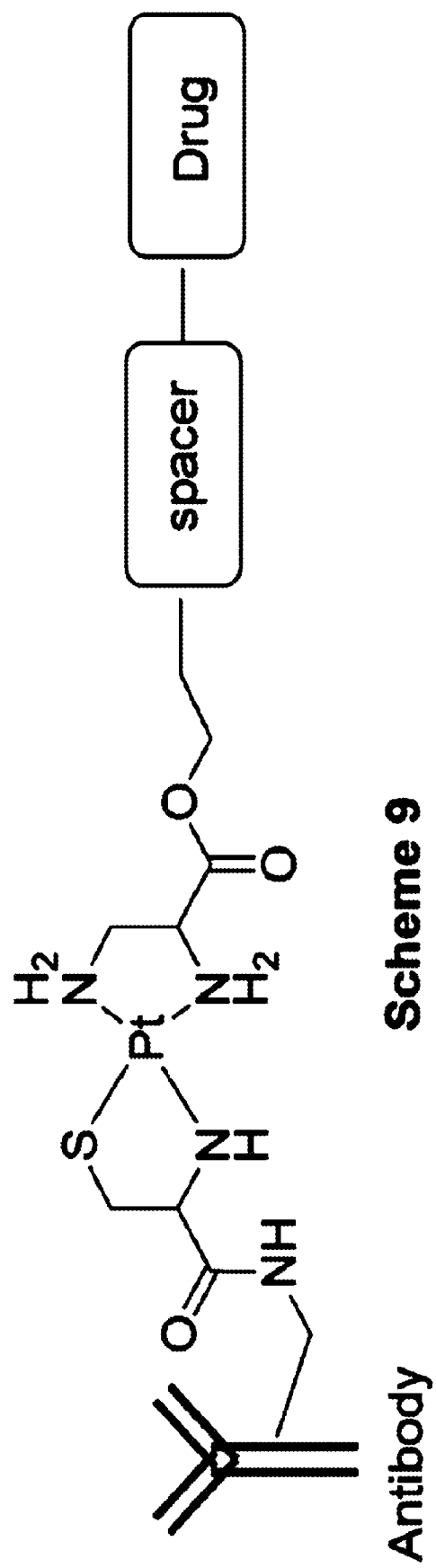
Figure 16B:
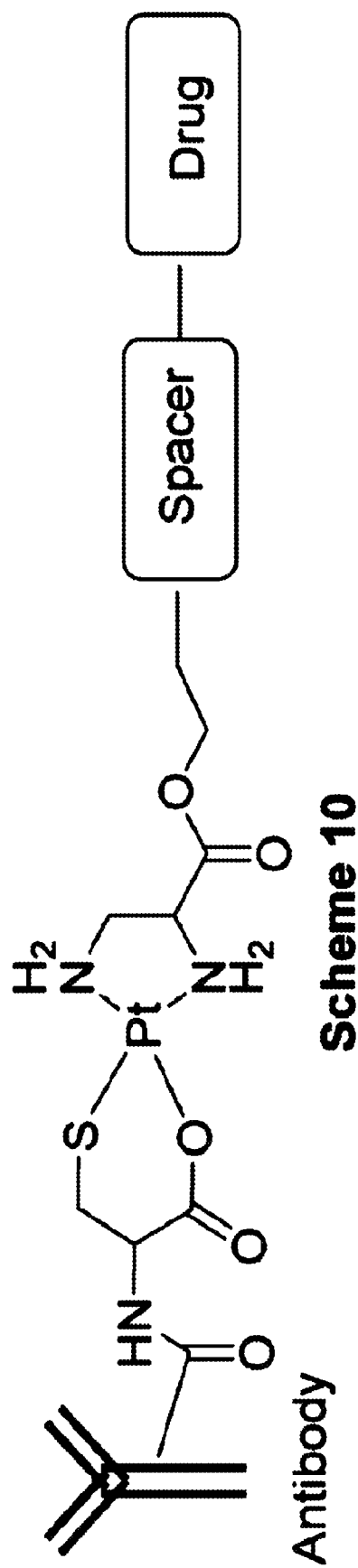
Figure 16C:
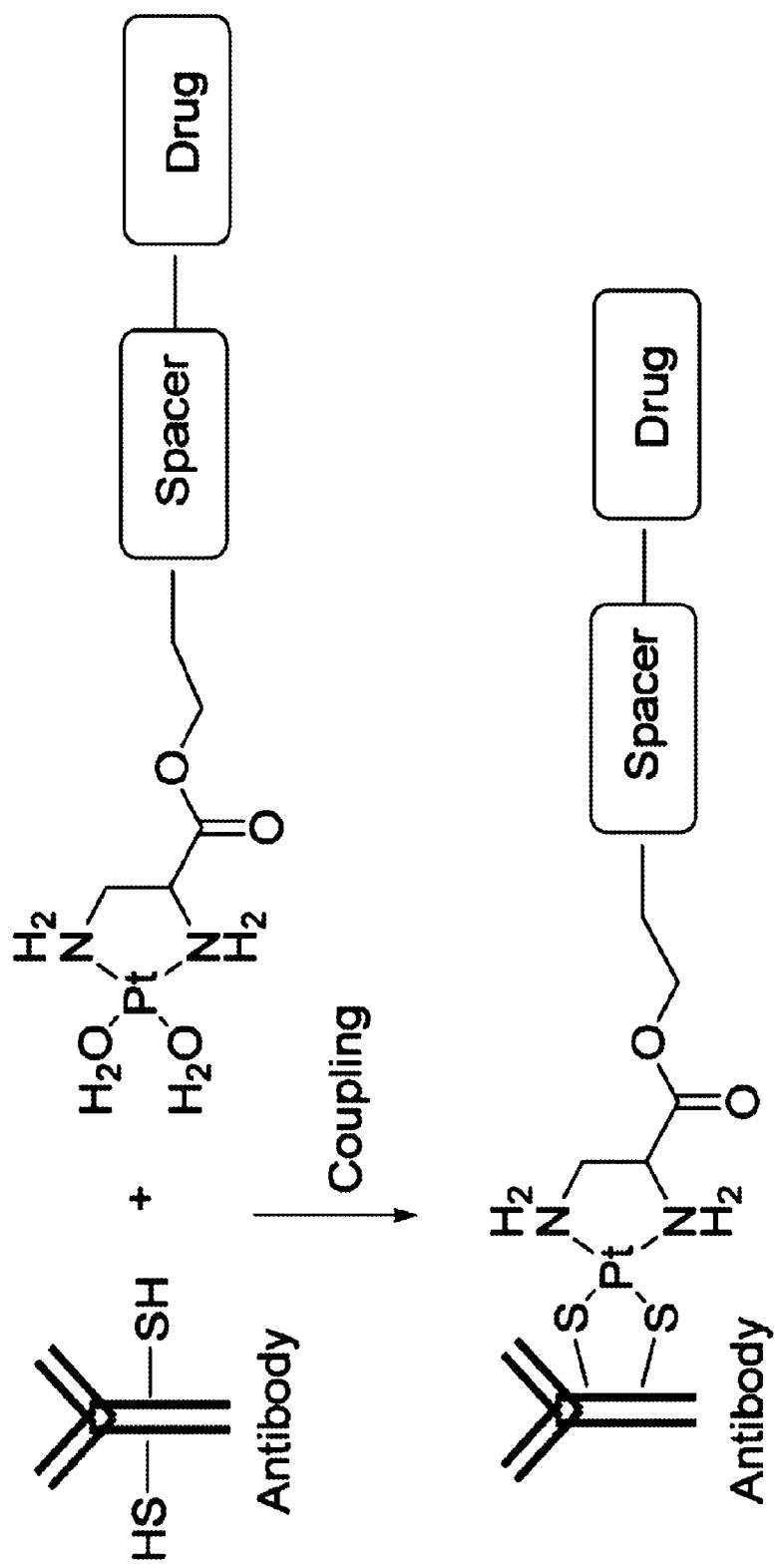
Figure 17:
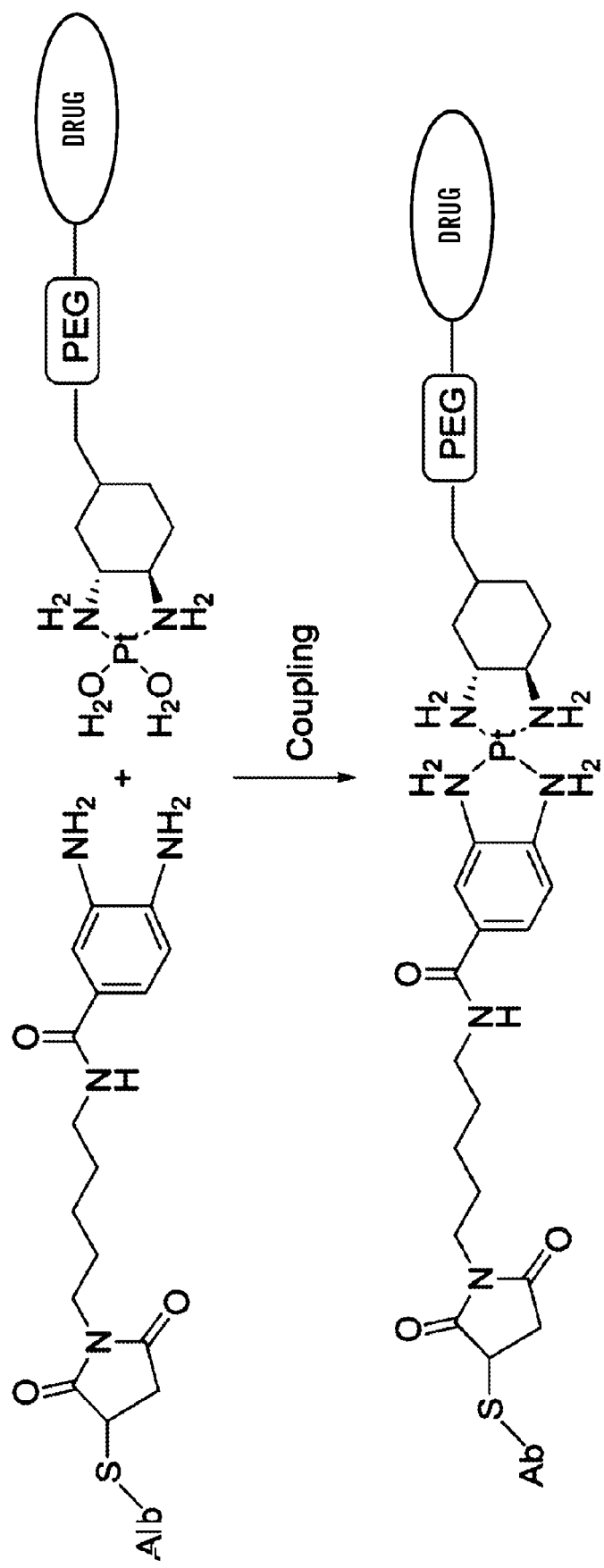
FIG. 17 is a schematic representation of an antibody-drug conjugate using a Pt(II) complex in the linker.
Figure 18:
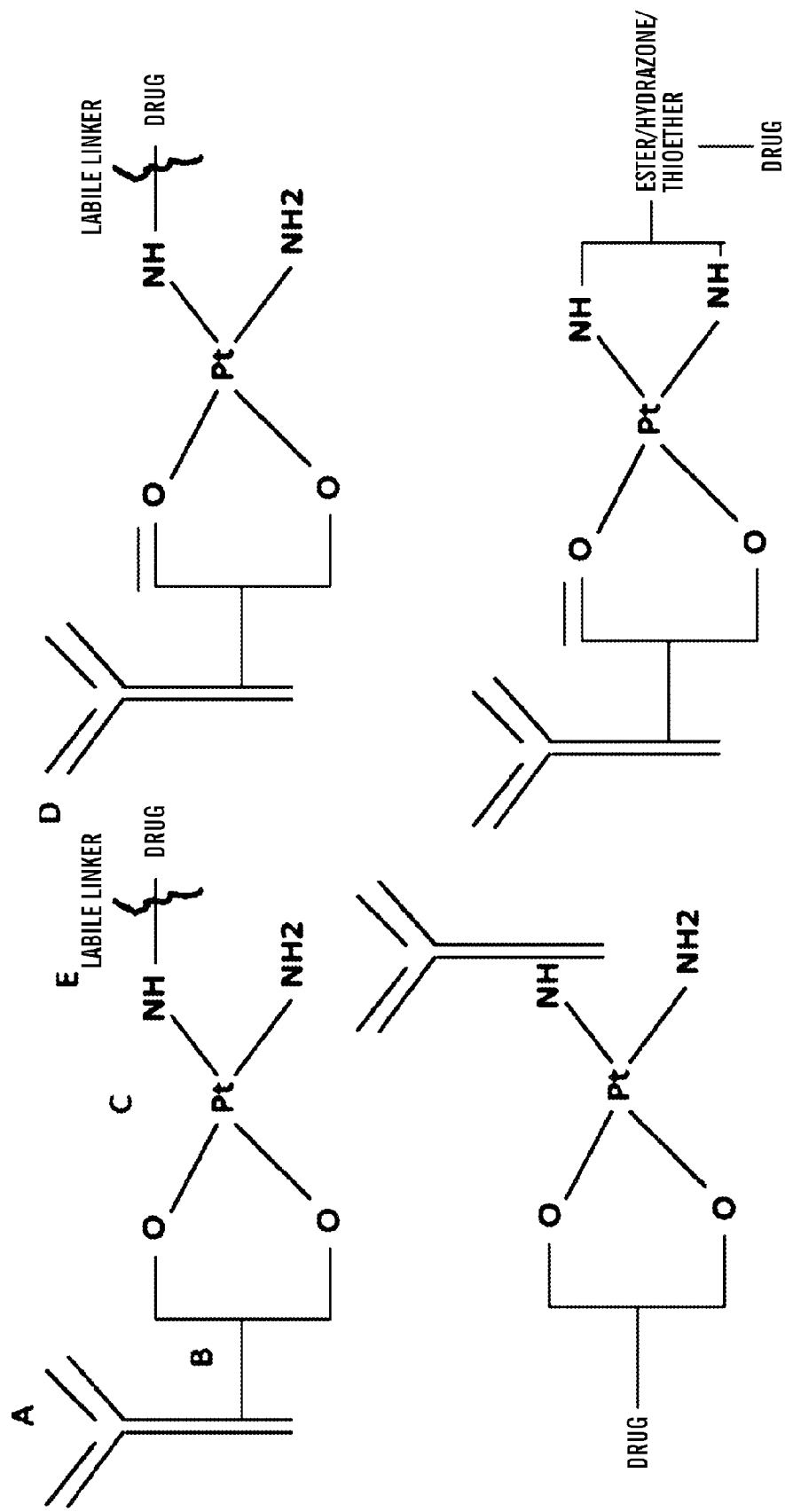
FIGS. 18-20 are schematic representations of ligand drug conjugates using a platinum complex comprising linker and antibody as the targeting moiety.
Figure 19:
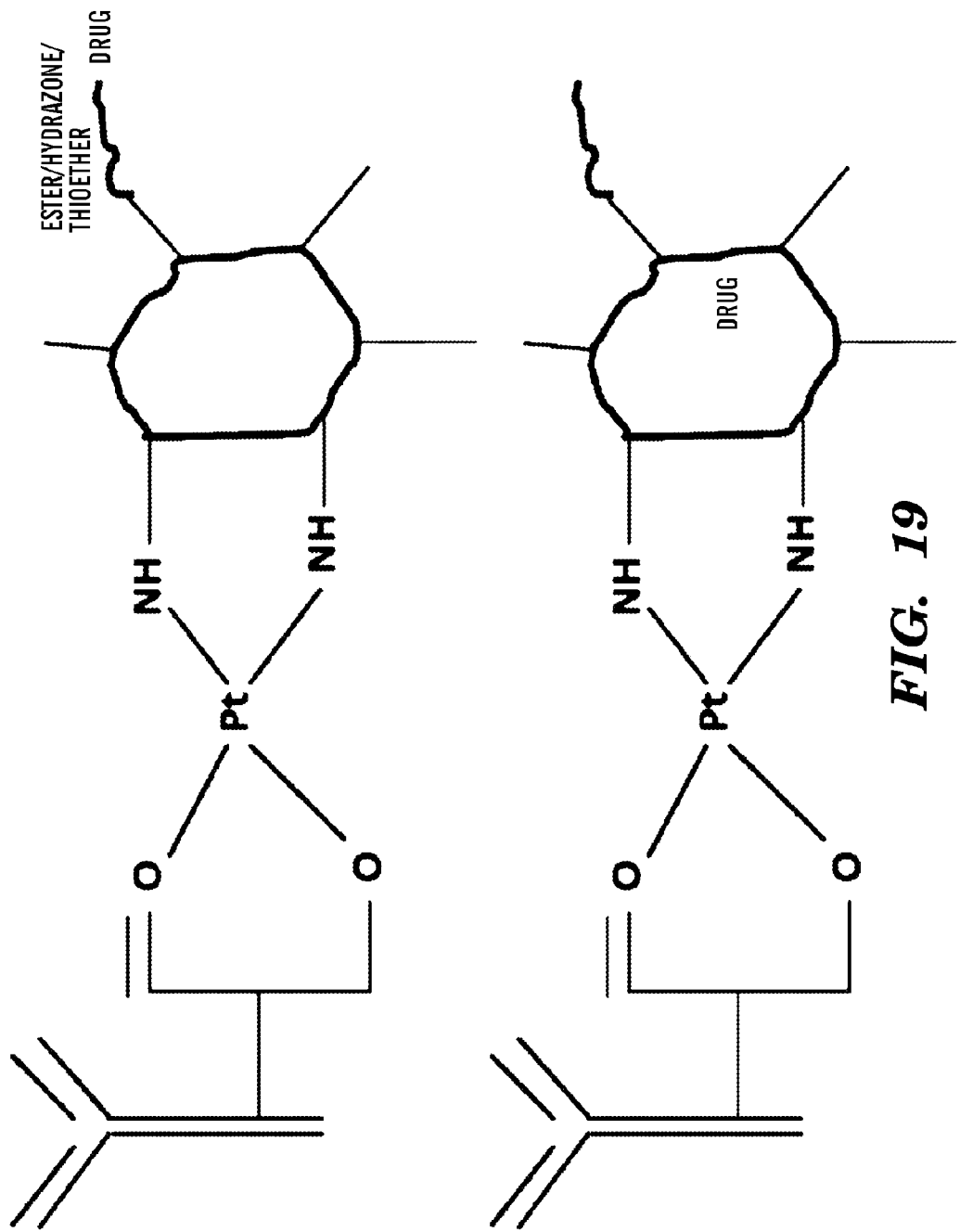
Figure 20:
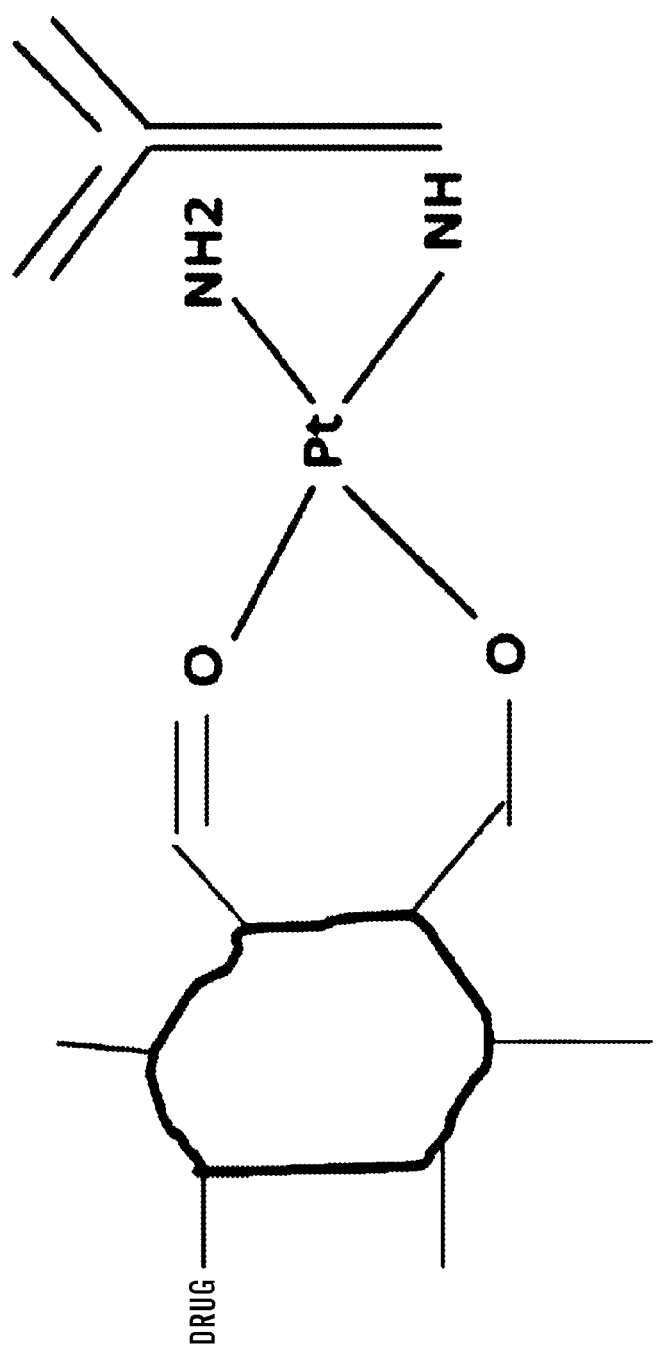

Synthesis of a ADC Using the Pt(II)-coordination Linker to Conjugate the Cytotoxic Drug Meayamycin Synthesis of a ADC using the Pt(II)-coordination linker to conjugate the cytotoxic drug meayamycin can be carried out using the method outlined in FIGS. 15A-15C. FIGS. 15A-15C show a schematic representation of the synthesis of an antibody conjugated to the cytotoxic meayamycin using Pt(II) coordination linker (steps 1-3).

All patents and other publications identified in the specification and examples are expressly incorporated herein by reference for all purposes. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

What is claimed is:

1. A ligand drug conjugate selected from the group consisting of:

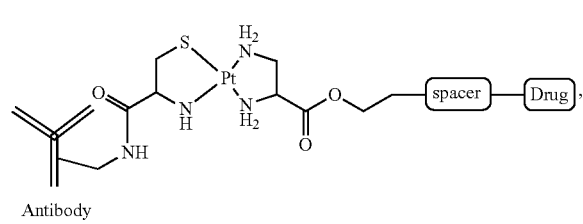

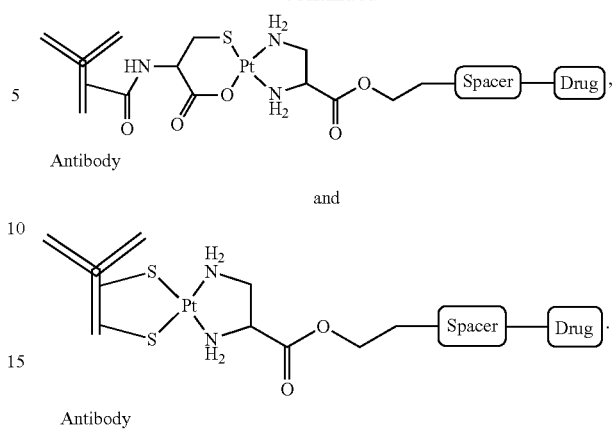

2. The conjugate of claim 1, wherein said ligand binds a protein, receptor, or cell marker on a surface of a cancer cell.

3. The conjugate of claim 1, wherein said first or second linker is a hydrocarbon, polyethylene glycol (PEG), an amino acid, a peptide, or a combination thereof, said hydrocarbon or PEG being substituted or unsubstituted.

4. The conjugate of claim 1, wherein the conjugate is:

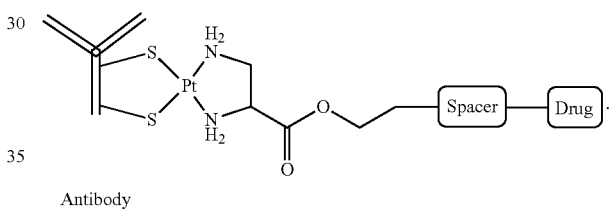

5. A method of treating a cancer in a subject in need thereof, the method comprising administering an effective amount of a conjugate of claim 1.

6. A ligand drug conjugate comprising a ligand connected to a ligand-targeted molecule, wherein said ligand-targeted molecule comprises a functional moiety, at least one first linker connected to said functional moiety, a coordination metal complex connected to said first linker, at least one second linker connected to said coordination metal complex, a drug connected to said second linker, and said ligand connected to said functional moiety, wherein the coordination metal complex is a platinum (II) complex selected from the group consisting of

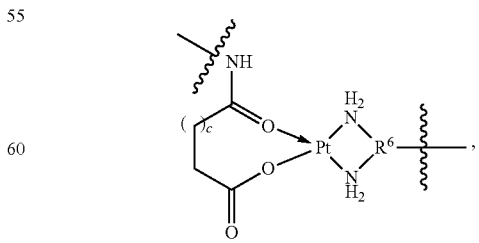

wherein c is 0,1,2,3,4, or 5 and $R^6$ is a cyclic or acyclic linker joining the two amino groups to first or the second linker

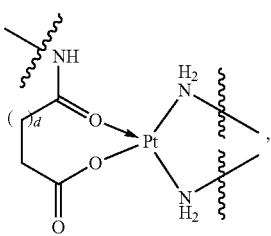

wherein d is 0, 1, 2, 3, 4, or 5 and the two amines are linked to different first or second linkers;

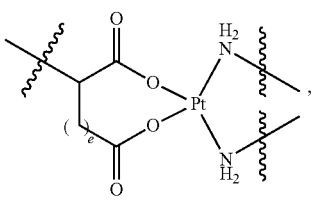

wherein e is 0, 1, 2, 3, 4, or 5, and the two amines are linked to different first or second linkers;

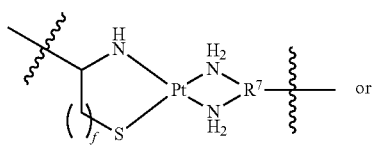

or

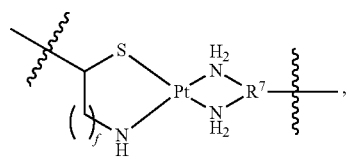

wherein f is 0, 1, 2, 3, 4, or 5 and $R^7$ is a cyclic or acyclic linker joining the two amino groups to the first or the second linker;

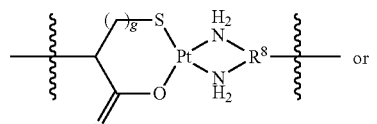

or

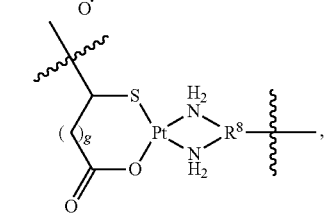

wherein g is 0, 1, 2, 3, 4, or 5 and $R^8$ is a cyclic or acyclic linker joining the two amino groups to the first or the second linker; or

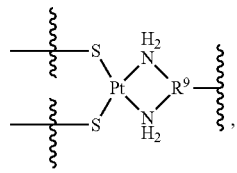

wherein $R^9$ is a cyclic or acyclic linker joining the two amino groups to the first or the second linker.

7. The conjugate of claim 6, wherein said platinum (II) complex is

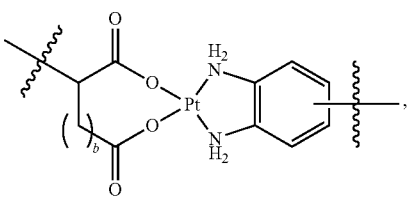

wherein b is 0, 1, 2, 3, 4, or 5;

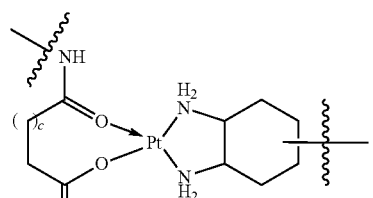

or

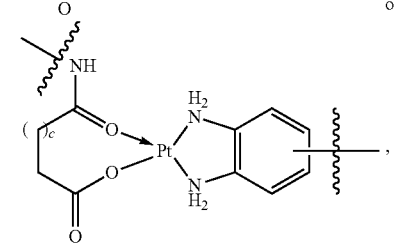

wherein c is 0, 1, 2, 3, 4, or 5;

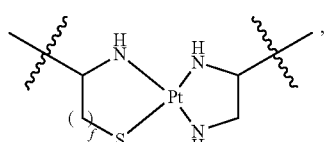

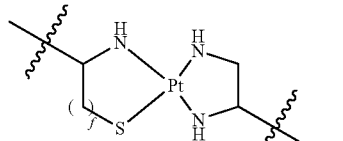

or

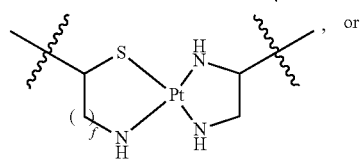

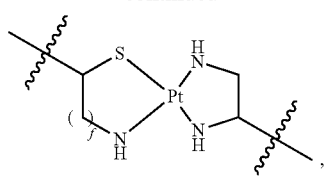
wherein f is 0, 1, 2, 3, 4, or 5; or
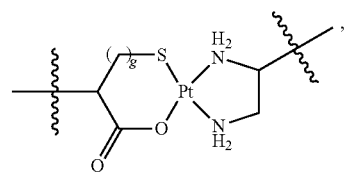
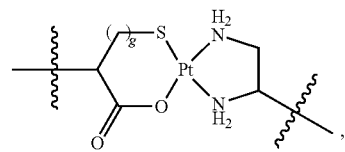
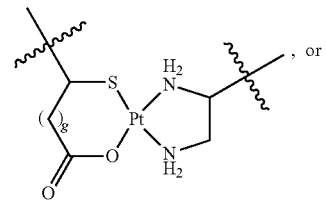, or
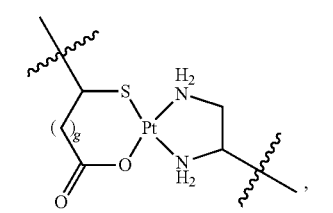
wherein g is 0, 1, 2, 3, 4, or 5.
8. The conjugate of claim 7, wherein said platinum (II) complex is
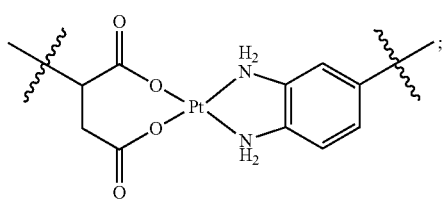
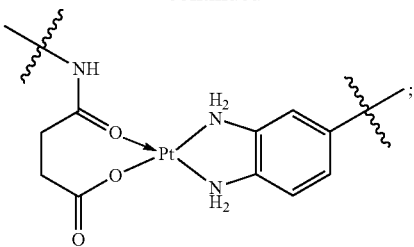
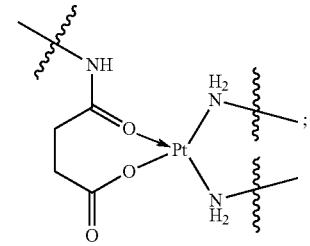
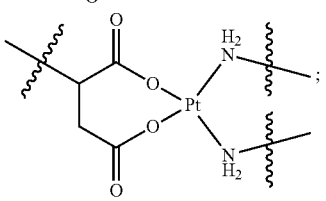
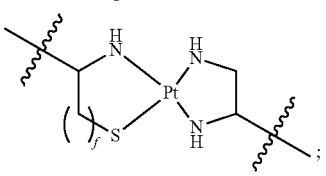
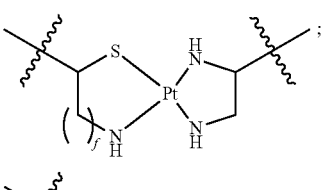
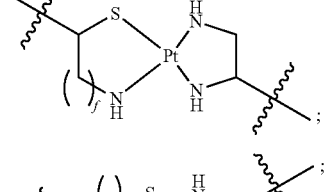
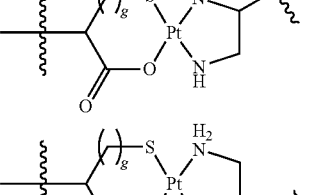
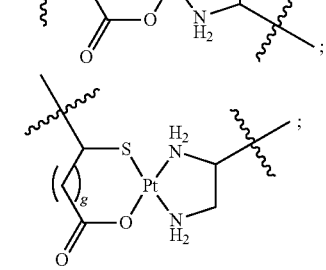

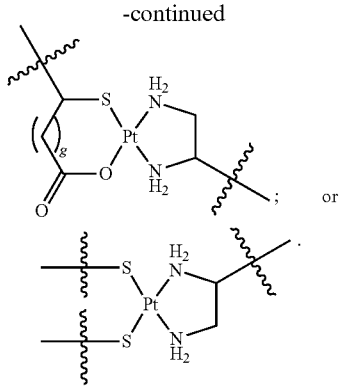

9. The conjugate of claim 6, wherein said ligand binds a protein, receptor, or cell marker on a surface of a cancer cell.

10. The conjugate of claim 6, wherein said first or second linker is a hydrocarbon, polyethylene glycol (PEG), an amino acid, a peptide, or a combination thereof, said hydrocarbon or PEG being substituted or unsubstituted.

11. A method of treating a cancer in a subject in need thereof, the method comprising administering an effective amount of a conjugate of claim 6.

* * * * *